(12) United States Patent
Dobler et al.

(10) Patent No.: US 8,372,885 B2
(45) Date of Patent: Feb. 12, 2013

(54) ORGANIC COMPOUNDS AND THEIR USES

(75) Inventors: Markus Rolf Dobler, Arlington, MA (US); Francois Lenoir, Waitham, MA (US); David Thomas Parker, Lexington, MA (US); Yunshan Peng, Cambridge, MA (US); Grazia Piizzi, Saint Louis (FR); Sompong Wattanasin, Waltham, MA (US)

(73) Assignee: Novartis AG, Basel (CH)

( * ) Notice: Subject to any disclaimer, the term of this patent is extended or adjusted under 35 U.S.C. 154(b) by 589 days.

(21) Appl. No.: 12/557,654

(22) Filed: Sep. 11, 2009

(65) Prior Publication Data

US 2010/0120872 A1 May 13, 2010

Related U.S. Application Data

(60) Provisional application No. 61/097,664, filed on Sep. 17, 2008.

(51) Int. Cl.
*A61K 31/19* (2006.01)
*C07C 229/00* (2006.01)
*C07C 259/04* (2006.01)

(52) U.S. Cl. .......... 514/575; 562/621; 562/433

(58) Field of Classification Search .......... 562/621, 562/433; 514/575
See application file for complete search history.

(56) References Cited

U.S. PATENT DOCUMENTS

| 2003/0236304 | A1 | 12/2003 | Jolidon et al. | |
| 2006/0154988 | A1* | 7/2006 | Andersen et al. | 514/575 |
| 2006/0160894 | A1 | 7/2006 | Fernandez Serrat et al. | |

FOREIGN PATENT DOCUMENTS

| GB | 1 577 345 | 10/1980 |
| WO | 2007/049729 | 5/2007 |

OTHER PUBLICATIONS

Munakata, et al, "Therapy for Urolithiasis[ . . . ]" Chem. and Pharm Bulletin, Pharm Soc. Japan v 28, No. 7 (1980) pp. 2045-2051.
Kundu, et al, "Identification of Novel a-Glucosidase Inhibitors by Screening Libraries Based on N- [C(Benzyloxy) Benzoyl] Alanine Derivatives" Curr. Topics in Med. Chem v 5 n7 (2002) pp. 545-550.
Kleinman, et al, "Striking Effect of Hydroxamic Acid Substitution on the Phosphodiesterase Type 4 (PDE4) and TNFa Inhibitory Activity of Two Series of Rolipram Analogues: Implications for a New Active Site Model of PDE4" J Med Chem (1998) pp. 266-270.
Kline, et al, "Potent, Novel in Vitro Inhibitors of the *Pseudomonas aeruginosa* Deacetylase LpxC" J Med Chem. v.45, n. 14 (2002) pp. 3112-3129.
Dan, et al, "Discovery of hydroxamic acid analogs as dual inhibitors of phosphodiesterase-1 and -5" Bioorg. and Med. Chem. Letters v 15 (2005) pp. 4085-4090.
Nair, et al, "Folate Analogues. 26. Syntheses and Antifolate Activity of 10-Substituted Derivatives of 5,8-Dideazafolic Acid and of the Poly-y-glutamyl Metabolites of N10-Propargyl-5,8-dideazafolic Acid (PDDF)" J. Med. Chem v 29, n7 (1986) pp. 1754-1760.
Kato, et al, "Heterocycles by Cycloaddition. Part 8.' Preparation of [I ] Benzopyrano[4,3-1A-pyrroles by Intramolecular Cycloaddition-Extrusion of Mesoionic Oxazolium-5-olates" J. Chem Soc, Perkins Trans 1, N2 (1989) pp. 361-363.

* cited by examiner

*Primary Examiner* — Shengjun Wang
(74) *Attorney, Agent, or Firm* — Mark W. Milstead

(57) ABSTRACT

The present application describes organic compounds of a general formula:

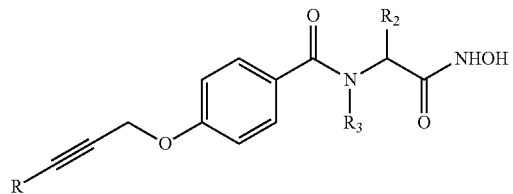

and salts, and isomers thereof, wherein R, $R_2$ and $R_3$ are defined in the specification. The compounds are useful for treating a gram-negative bacterial infection.

10 Claims, No Drawings

ORGANIC COMPOUNDS AND THEIR USES

This application claims benefit under 35 U.S.C. §119(e) of U.S. Provisional Application No. 61/097,664, filed Sep. 17, 2008, the contents of which are incorporated herein by reference in their entirety.

BACKGROUND

1. Field of the Invention

This invention pertains generally to treating bacterial infections. In certain aspects, the invention pertains to treating infections caused by gram-negative bacteria. More specifically, the invention described herein pertains to treating gram-negative infections by inhibiting activity of UDP-3-O—(R-3-hydroxydecanoyl)-N-acetylglucosamine deacetylase (LpxC). The present invention provides small molecule inhibitors of LpxC, pharmaceutical formulations containing such inhibitors, methods of treating patients with such pharmaceutical formulations, and methods of preparing such pharmaceutical formulations and inhibitors. The inhibitors can be used to treat Gram-negative infections of patients alone and in combination with other antibacterials.

2. Background of the Invention

Over the past several decades, the frequency of antimicrobial resistance and its association with serious infectious diseases have increased at alarming rates. The increasing prevalence of resistance among nosocomial pathogens is particularly disconcerting. Of the over 2 million nosocomial infections occurring each year in the United States, 50 to 60% are caused by antimicrobial-resistant strains of bacteria. Thus, high rate of resistance increases the morbidity, mortality, and costs associated with nosocomial infections. In the United States, nosocomial infections are thought to contribute to or cause more than 77,000 deaths per year and cost approximately $5 to $10 billion annually. Among Gram-positive organisms, the most important resistant pathogens are methicillin-(oxacillin-)resistant *Staphylococcus aureus*, β-lactam-resistant and multidrug-resistant pneumococci, and vancomycin-resistant enterococci. Important causes of Gram-negative resistance include extended-spectrum β-lactamases (ESBLs) in *Klebsiella pneumoniae*, *Escherichia coli*, and *Proteus mirabilis*, high-level third-generation cephalosporin (Amp C) β-lactamase resistance among *Enterobacter* species and *Citrobacter freundii*, and multi-drug-resistance genes observed in *Pseudomonas*, *Acinetobacter*, and *Stenotrophomonas*.

The problem of antibacterial resistance is compounded by the existence of bacterial strains resistant to multiple antibacterials. For example, *Pseudomonas aeruginosa* isolates resistant to fluoroquinolones are virtually all resistant to additional antibacterials.

Thus there is a need for new antibacterials, particularly antibacterials with novel mechanisms of action. Most of the antibacterial discovery effort in the pharmaceutical industry is aimed at development of drugs effective against gram-positive bacteria. However, there is also a need for new gram-negative antibacterials. Gram-negative bacteria are in general more resistant to a large number of antibacterials and chemotherapeutic agents than are gram-positive bacteria.

SUMMARY OF THE INVENTION

The present invention provides novel compounds, pharmaceutical formulations including the compounds, methods of inhibiting UDP-3-O—(R-3-hydroxydecanoyl)-N-acetylglucosamine deacetylase (LpxC), and methods of treating gram-negative bacterial infections.

In one aspect, the invention provides compounds of Formula I:

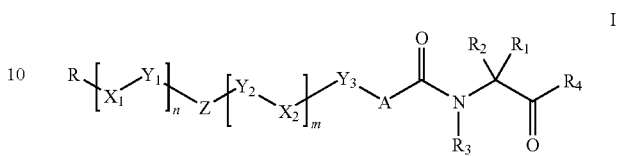

and salts thereof wherein

A represents a divalent cyclic radical selected from cycloalkylene, arylene, or heteroarylene, each of which is substituted with 0-4 residues independently selected from the group consisting of hydrogen, halogen, $C_1$-$C_6$alkyl, hydroxyl, $C_1$-$C_6$alkoxy, amino, mono- and di $C_1$-$C_6$alkyl amino, and 5-7 membered heterocycle;

R is hydrogen, halogen, hydroxyl, amino, or selected from the group consisting of $C_1$-$C_8$alkyl, $C_2$-$C_8$alkenyl, $C_2$-$C_8$alkynyl, $C_1$-$C_8$haloalkyl, $C_2$-$C_8$haloalkenyl, $C_2$-$C_8$haloalkynyl, $C_1$-$C_8$haloalkoxy, hydroxy$C_1$-$C_8$alkyl, cycloalkyl$C_0$-$C_4$alkyl, heterocycle$C_0$-$C_4$alkyl, cycloalkyl$C_0$-$C_4$alkoxy, heterocycle$C_0$-$C_4$alkyloxy, COOH, CONH$_2$, $C_1$-$C_8$alkanoyl, $C_1$-$C_8$alkoxycarbonyl, mono- and di- $C_1$-$C_8$alkylamino, each of which is substituted with 0-4 residues independently selected from the group consisting of hydrogen, halogen, $C_1$-$C_6$alkyl, hydroxyl, oxo, $C_1$-$C_6$alkoxy, amino, mono- and di $C_1$-$C_6$alkyl amino, and 5-7 membered heterocycle;

$R_1$ is hydrogen or $C_1$-$C_8$alkyl $R_2$ is selected from the group consisting of:
a) —$(CH_2)_r$C$(R_{2a}R_{2b})(CH_2)_s$OR$_5$;
b) —$(CH_2)_r$C$(R_{2a}R_{2b})(CH_2)_s$NR$_6$R$_7$;
c) —$(CH_2)_r$C$(R_{2a}R_{2b})(CH_2)_s$N$(R_6)$COR$_5$;
d) —$(CH_2)_r$C$(R_{2a}R_{2b})(CH_2)_s$N$(R_6)$CONR$_6$R$_7$;
e) —$(CH_2)_r$C$(R_{2a}R_{2b})(CH_2)_s$N$(R_6)$C(=NH)NR$_6$R$_7$;
f) —(CHR$_{2a}$R$_{2b}$);
g) —$(CH_2)_r$C$(R_{2a}R_{2b})$CN
h) —$(CH_2)_r$C$(R_{2a}R_{2b})$CO$_2$R$_5$
i) —$(CH_2)_r$C$(R_{2a}R_{2b})$CONR$_6$R$_7$; wherein each occurrence of $R_{2a}$, $R_{2b}$, $R_5$, $R_6$, and $R_7$ are independently selected at each occurrence from the group consisting of
a) hydrogen;
b) substituted or unsubstituted $C_1$-$C_6$alkyl;
c) substituted or unsubstituted $C_1$-$C_6$haloalkyl
d) substituted or unsubstituted aryl$C_0$-$C_4$alkyl;
e) substituted or unsubstituted $C_3$-$C_7$cycloalkyl$C_0$-$C_4$alkyl
f) substituted or unsubstituted heterocyclyl$C_0$-$C_4$alkyl; and
g) substituted or unsubstituted heteroaryl$C_0$-$C_4$alkyl; or geminal $R_6$ and $R_7$, taken in combination with the N atom to which they are attached, form a substituted or unsubstituted heterocyclic ring, having 3 to 8 ring atoms and 1-3 ring heteroatoms independently selected from the group consisting of N, O or S; or $R_{2a}$ and $R_{2b}$, taken in combination with the C atom to which they are attached, form a substituted or unsubstituted saturated ring having 3 to 8 ring atoms and 0-2 ring heteroatoms independently selected from the group consisting of N, O or S;

$R_3$ is hydrogen or $C_1$-$C_3$alkyl; or $R_3$ and $R_2$ taken in combination with the intervening atoms form a substituted or unsubstituted heterocyclic ring having from 3 to 8 ring atoms and 0, 1, or 2 additional ring heteroatoms independently selected from N, O or S;

$R_4$ is selected from OH, $NH_2$, and NHOH;

$X_1$ and $X_2$ are independently selected from the group consisting of O, $S(O)_q$, and $NR_8$;

$R_8$ is hydrogen, $C_1$-$C_8$alkyl, $C_3$-$C_8$cycloalkyl$C_0$-$C_4$alkyl, or $C_1$-$C_8$alkanoyl;

$Y_1$ and $Y_2$ are independently selected from $C_1$-$C_6$alkylene groups which are unsubstituted or substituted one or more times with $R_6$;

$Y_3$ is a bond or selected from $C_1$-$C_6$alkylene groups which are unsubstituted or substituted one or more times with $R_6$;

Z is absent, ethenylene (e.g., —$CR_9$=$CR_9$—) or ethynylene (e.g., —C≡C—);

$R_9$ is independently selected at each occurrence from the group consisting of hydrogen and $C_1$-$C_4$alkyl;

m and n are independently selected from the group consisting of 0, 1 and 2 wherein m+n is 1 or 2;

q is 0, 1, or 2; and r and s are independently selected from the group consisting of 0, 1, 2, 3, and 4.

In one aspect, the invention provides a method of inhibiting a deacetylase enzyme in gram-negative bacteria, thereby affecting bacterial growth, comprising administering to a patient in need of such inhibition a compound of formula I.

In another aspect, the invention provides a method of inhibiting LpxC, thereby modulating the virulence of a bacterial infection, comprising administering to a patient in need of such inhibition a compound of formula I.

In another aspect, the invention provides a method for treating a subject with a gram-negative bacterial infection comprising administering to the subject in need thereof an antibacterially effective amount of a compound of formula I with a pharmaceutically acceptable carrier. In certain embodiments, the subject is a mammal and in some other embodiments, the subject is a human.

In another aspect, the invention provides a method of administering an inhibitory amount of a compound of formula I to fermentative or non-fermentative gram-negative bacteria. In certain embodiment of the method of administering an inhibitory amount of a compound of formula I to fermentative or non-fermentative gram-negative bacteria, the gram-negative bacteria are selected from the group consisting of *Pseudomonas aeruginosa* and other *Pseudomonas* species, *Stenotrophomonas maltophila*, *Burkholderia cepacia* and other *Burkholderia* species, *Alcaligenes xylosoxidans*, species of *Acinetobacter, Enterobacteriaceae, Haemophilus, Moraxella, Bacteroids, Fransicella, Shigella, Proteus, Vibrio, Salmonella, Bordetella, Helicobactor, Legionella, Citrobactor, Serratia, Campylobactor, Yersinia* and *Neisseria*.

In another embodiment, the invention provides a method of administering an inhibitory amount of a compound of formula I to gram-negative bacteria, such as Enterobacteriaceae which is selected from the group consisting of organisms such as *Serratia, Proteus, Klebsiella, Enterobacter, Citrobacter, Salmonella, Providencia, Morganella, Cedecea,* and *Edwardsiella* species and *Escherichia coli*.

Another embodiment of the invention provides a pharmaceutical composition comprising an effective amount of a compound of Formula I with a pharmaceutically acceptable carrier thereof.

Pharmaceutical formulations according to the present invention are provided which include any of the compounds described above in combination with a pharmaceutically acceptable carrier.

Another embodiment of the invention provides a method of co-administering the compound of formula I with other therapeutic agents that are selected for their particular usefulness against the condition that is being treated.

For example, the compound of formula I is useful in combination with other anti-bacterial agents to treat a broader spectrum of bacterial infections. The compound of formula I augments the sensitivity of gram-negative bacteria to existing classes of antibacterials. Combinations of the presently disclosed compounds with other anti-bacterial agents are within the scope of the invention. Such anti-bacterial agents include, but are not limited to, Ampicillin, Piperacillin, Penicillin G, Ticarcillin, Imipenem, Meropenem, Azithromycin, erythromycin, Aztreonam, Cefepime, Cefotaxime, Ceftriaxone, Cefatazidime, Ciprofloxacin, Levofloxacin, Clindamycin, Doxycycline, Gentamycin, Amikacin, Tobramycin, Tetracycline, Tegacyclin, Rifampicin, and Polymyxin.

Other aspects of the invention are discussed infra.

DETAILED DESCRIPTION OF THE INVENTION

The present invention provides novel compounds, methods for inhibiting LpxC in gram-negative bacteria, and novel methods for treating bacterial infections. The compounds provided herein can be formulated into pharmaceutical formulations and medicaments that are useful in the methods of the invention. The invention also provides for the use of the compounds in preparing medicaments and pharmaceutical formulations, for use of the compounds in inhibiting LpxC, and for use of the compounds in treating bacterial infections in a subject.

The following abbreviations and definitions are used throughout this application:

"LpxC" is an abbreviation that stands for UDP-3-O—(R-3-hydroxydecan-oyl)-N-acetylglucosamine deacetylase.

This invention is directed to compounds of Formula I and subformulae thereof, and intermediates thereto, as well as pharmaceutical compositions containing the compounds for use in treatment of bacterial infections. This invention is also directed to the compounds of the invention or compositions thereof as LpxC inhibitors. The compounds are particularly useful in interfering with the life cycle of gram-negative bacteria and in treating or preventing a gram-negative bacterial infection or physiological conditions associated therewith. The present invention is also directed to methods of combination therapy for treating or preventing an gram-negative bacterial infection in patients using the compounds of the invention or pharmaceutical compositions, or kits thereof in combination with at least one other therapeutic agent.

Certain compounds of the instant invention include those compounds or salts thereof of Formula I in which in is 1 and n is 0. In other compounds of Formula I, $X_2$ is O or S. In certain other compounds of Formula I, in is 1, n is 0, $X_2$ is O or S; $Y_2$ is $C_1$-$C_3$alkylene; and $Y_3$ is a bond. In still other compounds of Formula I, in is 1, n is 0, $X_2$ is O or S; $Y_2$ is $C_1$-$C_3$alkylene; $Y_3$ is a bond; and Z is ethynylene.

In certain other embodiments, compounds of Formula I include those in which m is 1, n is 0, $X_2$ is O or S; $Y_2$ is $C_1$-$C_3$alkylene; $Y_3$ is a bond; Z is ethynylene; and R is selected from the group consisting of $C_1$-$C_6$alkyl, $C_2$-$C_4$alkenyl, $C_1$-$C_6$haloalkyl, hydroxy$C_1$-$C_6$alkyl, cycloalkyl$C_0$-$C_4$alkyl, and heterocycle$C_0$-$C_4$alkyl, each of which is substituted with 0-4 residues independently selected from the group consisting of hydrogen, halogen, $C_1$-$C_6$alkyl, hydroxyl, $C_1$-$C_6$alkoxy, amino, mono- and di $C_1$-$C_6$alkyl amino, and 5-7 membered heterocycle;

Certain other compounds of Formula I include those in which A is a cyclohexylene, phenylene or pyridylene each of which is unsubstituted or substituted with 1 or 2 residues independently selected from halogen, methyl, hydroxy, amino or methoxy. Certain other compounds of Formula I include those in which A is phenylene which is unsubstituted or substituted with fluoro, chloro, or methyl.

Still other compounds of Formula I include those in which Z is ethynylene, m is 1, n is 0, and R is selected from the group consisting of $C_1$-$C_6$alkyl, $C_2$-$C_6$alkenyl, $C_1$-$C_5$haloalkyl, $C_2$-$C_6$haloalkenyl, $C_1$-$C_6$alkoxy, $C_1$-$C_6$haloalkoxy, hydroxy$C_1$-$C_6$alkyl, cycloalkyl$C_0$-$C_2$alkyl, heterocycle$C_0$-$C_2$alkyl, COOH, CONH$_2$, $C_1$-$C_6$alkanoyl, $C_1$-$C_6$alkoxycarbonyl, mono-and di- $C_1$-$C_6$alkylamino.

Certain other compounds of Formula I include those in which $R_4$ is hydroxy.

Certain other compounds of Formula I include those in which $R_9$ is independently selected from hydrogen or methyl. In yet other compounds of Formula I, each occurrence of $R_9$ is hydrogen.

Certain other compounds of Formula I include those in which $R_1$ is hydrogen or $C_1$-$C_4$alkyl $R_2$ is selected from the group consisting of:
  a) —$(CH_2)_rC(R_{2a}R_{2b})(CH_2)_sOR_5$;
  b) —$(CH_2)_rC(R_{2a}R_{2b})(CH_2)_sNR_6R_7$;
  c) —$CHR_{2a}R_{2b}$;
each occurrence of $R_{2a}$, $R_{2b}$, $R_5$, $R_6$, and $R_7$ are independently selected at each occurrence from the group consisting of
  a) hydrogen;
  b) substituted or unsubstituted $C_1$-$C_6$alkyl;
  c) substituted or unsubstituted $C_1$-$C_6$haloalkyl;
  d) substituted or unsubstituted $C_3$-$C_7$cycloalkyl$C_0$-$C_4$alkyl; and
  e) substituted or unsubstituted heterocyclyl$C_0$-$C_4$alkyl; or
  geminal $R_6$ and $R_7$, taken in combination with the N atom to which they are attached, form a substituted or unsubstituted heterocyclic ring, having 3 to 8 ring atoms and 1-3 ring heteroatoms independently selected from the group consisting of N, O or S; or
  $R_{2a}$ and $R_{2b}$, taken in combination with the C atom to which they are attached, form a substituted or unsubstituted saturated ring having 3 to 8 ring atoms and 0-2 ring heteroatoms independently selected from the group consisting of N, O or S;
r is 0 or 1; and
s is 0.

Certain other compounds of Formula I include those compounds or salts thereof represented by Formula II:

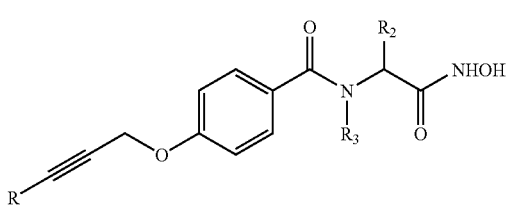

II and tautomers, salts, and isomers thereof, wherein
R is $C_1$-$C_6$alkyl or $C_3$-$C_6$cycloalkyl;
$R_2$ is $CR_{2a}R_{2b}OR_5$ or $CR_{2a}R_{2b}NR_6R_7$;
$R_{2a}$ is hydrogen, $C_1$-$C_4$alkyl, $C_1$-$C_4$haloalkyl, or $C_3$-$C_6$cycloalkyl;
$R_{2b}$ is hydrogen or $C_1$-$C_4$alkyl;

$R_3$ and $R_5$ are independently selected from hydrogen or $C_1$-$C_4$alkyl; and
$R_6$ and $R_7$ are independently selected from the group consisting of hydrogen, $C_1$-$C_4$alkyl, and $C_1$-$C_4$alkanoyl.

In certain aspects, compounds of Formula II include those in which R is methyl, ethyl, cyclopropyl, cyclobutyl, or cyclopentyl.

In certain aspects, compounds of Formula II include those in which $R_2$ is $CH_2OH$, $CH_2NH_2$, $CHMeNH_2$, $CMe_2NH_2$, $CH(CF_3)NH_2$, $CH(cyclopropyl)NH_2$, $CH_2NHMe$, $CHMeNHMe$, $CMe_2NHMe$, $CH(CF_3)NHMe$, $CH(cyclopropyl)NHMe$, $CH_2NHEt$, $CHMeNHEt$, $CMe_2NHEt$, $CH(CF_3)NHEt$, $CH(cyclopropyl)NHEt$, $CH_2NH(cyclopropyl)$, $CHMeNH(cyclopropyl)$, $CMe_2NH(cyclopropyl)$, $CH(CF_3)NH(cyclopropyl)$, and $CH(cyclopropyl)NH(cyclopropyl)$.

In certain aspects, compounds of Formula II include those in which $R_3$ is hydrogen.

In certain aspects, compounds of Formula I or II include those in which R is methyl, ethyl, cyclopropyl, cyclobutyl, or cyclopentyl;
$R_2$ is $CH_2OH$, $CH_2NH_2$, $CHMeNH_2$, $CMC_2NH_2$, $CH(CF_3)NH_2$, $CH(cyclopropyl)NH_2$, $CH_2NHMe$, $CHMeNHMe$, $CMe_2NHMe$, $CH(CF_3)NHMe$, $CH(cyclopropyl)NHMe$, $CH_2NHEt$, $CHMeNHEt$, $CMe_2NHEt$, $CH(CF_3)NHEt$, $CH(cyclopropyl)NHEt$, $CH_2NH(cyclopropyl)$, $CHMeNH(cyclopropyl)$, $CMe_2NH(cyclopropyl)$, $CH(CF_3)NH(cyclopropyl)$, and $CH(cyclopropyl)NH(cyclopropyl)$; and
$R_3$ is hydrogen.

In certain aspects, compounds of Formula I or II include those compounds or salts thereof in which
$R_1$ is hydrogen, deuterium, or $C_{1-4}$alkyl; and
$R_2$ is $CH_2OH$, $CH_2NH_2$, $CHMeNH_2$, $CMe_2NH_2$, $CH(CF_3)NH_2$, $CH(cyclopropyl)NH_2$, $CH_2NHMe$, $CHMeNHMe$, $CMe_2NHMe$, $CH(CF_3)NHMe$, $CH(cyclopropyl)NHMe$, $CH_2NBEt$, $CHMeNHEt$, $CMe_2NHEt$, $CH(CF_3)NHEt$, $CH(cyclopropyl)NHEt$, $CH_2NH(cyclopropyl)$, $CHMeNH(cyclopropyl)$, $CMe_2NH(cyclopropyl)$, $CH(CF_3)NH(cyclopropyl)$, and $CH(cyclopropyl)NH(cyclopropyl)$.

In still other aspects, compounds of Formula I or II include those compounds or salts thereof in which
$R_1$ is hydrogen or deuterium; and
$R_2$ is $CHMeNH_2$, $CMe_2NH_2$, $CH(CF_3)NH_2$, $CH(cyclopropyl)NH_2$, $CH_2NHMe$, $CHMeNHMe$, or $CMe_2NHMe$.

In certain other compounds of Formula I, the ring hydrogen atoms of A residue are selected from $^1H$, $^2H$, and $^3H$ and combinations thereof. In certain compounds of Formula I the ring hydrogen atoms of the A ring are at least about 50% $^2H$, or at least about 75%, 90%, 95%, or 99% $^2H$.

In certain other compounds of Formula II, the hydrogen atoms of the methylene interposed between the oxygen and R—C≡C— (e.g., the $Y_2$ group of Formula I when $Y_2$ is $C_1$-alkylene) are selected from $^1H$, $^2H$, and $^3H$ and combinations thereof. In certain compounds the methylene hydrogen atoms are at least about 50% $^2H$, or at least about 75%, 90%, 95%, or 99% $^2H$. In certain other compounds of Formula II, the methine hydgrogen a to the hydroxamic acid is selected from $^1H$, $^2H$, and $^3H$. In certain compounds the methine hydrogen is at least about 50% $^2H$, or at least about 75%, 90%, 95%, or 99% $^2H$ atoms.

In certain other aspects, the invention provides compounds of Table A or Table B infra.

In another aspect, the invention provides a method of inhibiting a deacetylase enzyme in a gram-negative bacterium, the method comprising the step of contacting the gram-negative bacteria with a compound of the invention, e.g., a compound of Formula I or salt thereof.

In still another aspect, the invention provides a method for treating a subject with a gram-negative bacterial infection, the method comprising the step of administering to the subject in need thereof an antibacterially effective amount of a compound of the invention, e.g., a compound of Formula I or salt thereof with a pharmaceutically acceptable carrier.

As used herein, the term "subject" refers to an animal. In certain aspects, the animal is a mammal. A subject also refers to for example, primates (e.g., humans), cows, sheep, goats, horses, dogs, cats, rabbits, rats, mice, fish, birds and the like. In certain embodiments, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a", "an", "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The term "antibacterial agent" refers to agents synthesized or modified in the laboratory that have either bactericidal or bacteriostatic activity. An "active" agent in this context will inhibit the growth of *P. aeruginosa* and/or other gram-negative bacteria. The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the bacteria in the population are reduced or the population even eliminated. If an enzyme activity assay is used to screen for inhibitors, one can make modifications in uptake/efflux, solubility, half-life, etc. to compounds in order to correlate enzyme inhibition with growth inhibition. The activity of antibacterial agents is not necessarily limited to bacteria but may also encompass activity against parasites, virus, and fungi.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. Furthermore, the expression "$C_x$-$C_y$-alkyl", wherein x is 1-5 and y is 2-10 indicates a particular a group (straight- or branched-chain) of a particular range of carbons. For example, the expression $C_1$-$C_4$-alkyl includes, but is not limited to, methyl, ethyl, propyl, butyl, isopropyl, telt-butyl, isobutyl and sec-butyl. Moreover, the term $C_3$-$C_6$-cycloalkyl includes, but is not limited to, cyclopropyl, cyclopentyl, and cyclohexyl. As discussed below, these alkyl groups, as well as cycloalkyl groups, may be further substituted. "$C_0$-$C_n$alkyl" refers to a single covalent bond ($C_0$) or an alkyl group having from 1 to n carbon atoms; for example "$C_0$-$C_4$alkyl" refers to a single covalent bond or a $C_1$-$C_4$alkyl group; "$C_0$-$C_8$alkyl" refers to a single covalent bond or a $C_1$-$C_8$alkyl group. In some instances, a substituent of an alkyl group is specifically indicated. For example, "$C_1$-$C_4$hydroxyalkyl" refers to a $C_1$-$C_4$alkyl group that has at least one hydroxy substituent.

"Alkylene" refers to a divalent alkyl group, as defined above. $C_0$-$C_4$alkylene is a single covalent bond or an alkylene group having from 1 to 4 carbon atoms; and $C_0$-$C_6$alkylene is a single covalent bond or an alkylene group having from 1 to 6 carbon atoms.

A "cycloalkyl" is a group that comprises one or more saturated and/or partially saturated rings in which all ring members are carbon, such as cyclopropyl, cyclobutyl, cyclopentyl, cyclohexyl, cycloheptyl, cyclooctyl, adamantyl, decahydro-naphthalenyl, octahydro-indenyl, and partially saturated variants of the foregoing, such as cyclohexenyl. Cycloalkyl groups do not comprise an aromatic ring or a heterocyclic ring. Certain cycloalkyl groups are $C_3$-$C_8$cycloalkyl, in which the group contains a single ring with from 3 to 8 ring members. A "($C_3$-$C_8$cycloalkyl)$C_0$-$C_4$alkyl" is a $C_3$-$C_8$cycloalkyl group covalent bond or a $C_1$-$C_4$alkylene group.

Moreover, alkyl (e.g., methyl, ethyl, propyl, butyl, pentyl, hexyl, etc.) include both "unsubstituted alkyl" and "substituted alkyl", the latter of which refers to alkyl moieties having substituents replacing a hydrogen on one or more carbons of the hydrocarbon backbone, which allow the molecule to perform its intended function.

The term "substituted" is intended to describe moieties having substituents replacing a hydrogen on one or more atoms, e.g. C, O or N, of a molecule. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, morpholino, phenol, benzyl, phenyl, piperazine, cyclopentane, cyclohexane, pyridine, 5H-tetrazole, triazole, piperidine, or an aromatic or heteroaromatic moiety.

Further examples of substituents of the invention include moieties selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$, alkenyl (preferably $C_2$-$C_6$), alkynyl (preferably $C_2$-$C_6$), heterocyclic, carbocyclic, aryl (e.g, phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, (CR'R")$_{0-3}$NR'R" (e.g., —NH$_2$), (CR'R")$_{0-3}$CN (e.g., —CN), —NO$_2$, halogen (e.g., —F, —Cl, —Br, or —I), (CR'R")$_{0-3}$C(halogen)$_3$ (e.g., —CF$_3$), (CR'R")$_{0-3}$CH(halogen)$_2$, (CR'R")$_{0-3}$CH$_2$(halogen), (CR'R")$_{0-3}$CONR'R", (CR'R")$_{0-3}$(CNH)NR'R", (CR'R")$_{0-3}$S(O)$_{1-2}$NR'R", (CR'R")$_{0-3}$CHO, (CR'R")$_{0-3}$O(CR'R")$_{0-3}$H, (CR'R")$_{0-3}$S(O)$_{0-3}$R' (e.g., —SO$_3$H, —OSO$_3$H), (CR'R")$_{0-3}$O(CR'R")$_{0-3}$H (e.g., —CH$_2$OCH$_3$ and —OCH$_3$), (CR'R")$_{0-3}$S(CR'R")$_{0-3}$H (e.g., —SH and —SCH$_3$), (CR'R")$_{03}$OH (e.g., —OH), (CR'R")$_{0-3}$COR', (CR'R")$_{0-3}$(substituted or unsubstituted phenyl), (CR'R")$_{0-3}$(C$_3$-C$_8$ cycloalkyl), (CR'R")$_{0-3}$CO$_2$R' (e.g., —CO$_2$H), or (CR'R")$_{0-3}$OR' group, or the side chain of any naturally occurring amino acid; wherein R' and R" are each independently hydrogen, a C$_1$-C$_5$ alkyl, C$_2$-C$_5$ alkenyl, C$_2$-C$_5$ alkynyl, or aryl group. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, oxime, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. In certain embodiments, a carbonyl moiety (C=O) may be further derivatized with an oxime moiety, e.g., an aldehyde moiety may be derivatized as its oxime (—C=N—OH) analog. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (i.e., benzyl)).

The term "alkenyl" includes unsaturated aliphatic groups analogous in length and possible substitution to the alkyls described above, but which contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups that include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., C$_2$-C$_6$ for straight chain, C$_3$-C$_6$ for branched chain). Likewise, cycloalkenyl groups may have from 3-8 carbon atoms in their ring structure, and more preferably have 5 or 6 carbons in the ring structure. The term C$_2$-C$_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, acylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., C$_2$-C$_6$ for straight chain, C$_3$-C$_6$ for branched chain). The term C$_2$-C$_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "amine" or "amino" should be understood as being broadly applied to both a molecule, or a moiety or functional group, as generally understood in the art, and may be primary, secondary, or tertiary. The term "amine" or "amino" includes compounds where a nitrogen atom is covalently bonded to at least one carbon, hydrogen or heteroatom. The terms include, for example, but are not limited to, "alkylamino," "arylamino," "diarylamino," "alkylarylamino," "alkylaminoaryl," "arylaminoalkyl,""alkaminoalkyl," "amide," "amido," and "aminocarbonyl." The term "alkyl amino" comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "aryl" includes groups, including 5- and 6-membered single-ring aromatic groups that may include from zero to four heteroatoms, for example, phenyl, pyrrole, furan, thiophene, thiazole, isothiaozole, imidazole, triazole, tetrazole, pyrazole, oxazole, isoxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, anthryl, phenanthryl, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics." The aromatic ring can be substituted at one or more ring positions with such substituents as described above, as for example, alkyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

Certain aryl groups recited herein are $C_6$-$C_{10}$aryl$C_0$-$C_8$alkyl groups (i.e., groups in which a 6- to 10-membered carbocyclic group comprising at least one aromatic ring is linked via a single covalent bond or a $C_1$-$C_8$alkylene group). Such groups include, for example, phenyl and indanyl, as well as groups in which either of the foregoing is linked via $C_1$-$C_8$alkylene, preferably via $C_1$-$C_4$alkylene. Phenyl groups linked via a single covalent bond or $C_1$-$C_6$alkylene group are designated phenyl$C_0$-$C_6$alkyl (e.g., benzyl, 1-phenyl-ethyl, 1-phenyl-propyl and 2-phenyl-ethyl).

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, niazolyl, azetidinyl, 1,4-dioxanyl, hexahydroazepinyl, piperazinyl, piperidinyl, pyridin-2-onyl, pyrrolidinyl, morpholinyl, thiomoipholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropynolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof Attachment of a heterocyclyl substituent can occur via a carbon atom or via a heteroatom.

A "heterocycle$C_0$-$C_8$alkyl" is a heterocyclic group linked via a single covalent bond or $C_1$-$C_8$alkylene group. A (4- to 7-membered heterocycle)$C_0$-$C_8$alkyl is a heterocyclic group (e.g., monocyclic or bicyclic) having from 4 to 7 ring members linked via a single covalent bond or an alkylene group having from 1 to 8 carbon atoms. A "(6-membered heteroaryl)$C_0$-$C_6$alkyl" refers to a heteroaryl group linked via a direct bond or $C_1$-$C_6$alkyl group.

The term "acyl" includes compounds and moieties which contain the acyl radical ($CH_3CO$—) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarAamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups and may include cyclic groups such as cyclopentoxy. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "carbonyl" or "carboxy" includes compounds and moieties which contain a carbon connected with a double bond to an oxygen atom, and tautomeric forms thereof Examples of moieties that contain a carbonyl include aldehydes, ketones, carboxylic acids, amides, esters, anhydrides, etc. The term "carboxy moiety" or "carbonyl moiety" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl moiety. For example, the term includes moieties such as, for example, aminocarbonyl moieties, (wherein a nitrogen atom is bound to the carbon of the carbonyl group, e.g., an amide), aminocarbonyloxy moieties, wherein an oxygen and a nitrogen atom are both bond to the carbon of the carbonyl group (e.g., also referred to as a "carbamate"). Furthermore, aminocarbonylamino groups (e.g., ureas) are also include as well as other combinations of carbonyl groups bound to heteroatoms (e.g., nitrogen, oxygen, sulfur, etc. as well as carbon atoms). Furthermore, the heteroatom can be further substituted with one or more alkyl, alkenyl, alkynyl, aryl, aralkyl, acyl, etc. moieties.

The term "thiocarbonyl" or "thiocarboxy" includes compounds and moieties which contain a carbon connected with a double bond to a sulfur atom. The term "thiocarbonyl moiety" includes moieties that are analogous to carbonyl moieties. For example, "thiocarbonyl" moieties include aminothiocarbonyl, wherein an amino group is bound to the carbon atom of the thiocarbonyl group, furthermore other thiocarbonyl moieties include, oxythiocarbonyls (oxygen bound to the carbon atom), aminothiocarbonylamino groups, etc.

The term "ether" includes compounds or moieties that contain an oxygen bonded to two different carbon atoms or heteroatoms. For example, the term includes "alkoxyalkyl" which refers to an alkyl, alkenyl, or alkynyl group covalently bonded to an oxygen atom that is covalently bonded to another alkyl group.

The term "ester" includes compounds and moieties that contain a carbon or a heteroatom bound to an oxygen atom that is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "hydroxy" or "hydroxyl" includes groups with an —OH or —O⁻. The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" include moieties with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

Additionally, the phrase "any combination thereof" implies that any number of the listed functional groups and molecules may be combined to create a larger molecular architecture. For example, the terms "phenyl," "carbonyl" (or "=O"), "—O—," "—OH," and $C_{1-6}$ (i.e., —$CH_3$ and —$CH_2CH_2CH_2$—) can be combined to form a 3-methoxy-4-propoxybenzoic acid substituent. It is to be understood that when combining functional groups and molecules to create a larger molecular architecture, hydrogens can be removed or added, as required to satisfy the valence of each atom.

It is to be understood that all of the compounds of the invention described above will further include bonds between adjacent atoms and/or hydrogens as required to satisfy the valence of each atom. That is, bonds and/or hydrogen atoms are added to provide the following number of total bonds to each of the following types of atoms: carbon: four bonds; nitrogen: three bonds; oxygen: two bonds; and sulfur: two bonds.

Groups that are "optionally substituted" are unsubstituted or are substituted by other than hydrogen at one or more available positions, typically 1, 2, 3, 4 or 5 positions, by one or more suitable groups (which may be the same or different). Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substitutents).

It will be noted that the structures of some of the compounds of this invention include asymmetric carbon atoms. It is to be understood accordingly that the isomers arising from such asymmetry (e.g., all enantiomers, stereoisomers, rotamers, tautomers, diastereomers, or racemates) are included within the scope of this invention. Such isomers can be obtained in substantially pure form by classical separation techniques and by stereochemically controlled synthesis. Furthermore, the structures and other compounds and moieties discussed in this application also include all tautomers thereof. Compounds described herein may be obtained through art recognized synthesis strategies.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis- (Z)- or trans- (E)-form.

Accordingly, as used herein a compound of the present invention can be in the form of one of the possible isomers, rotamers, atropisomers, tautomers or mixtures thereof for example, as substantially pure geometric (cis or trans) isomers, diastereomers, optical isomers (antipodes), racemates or mixtures thereof Any resulting mixtures of isomers can be separated on the basis of the physicochemical differences of the constituents, into the pure or substantially pure geometric or optical isomers, diastereomers, racemates, for example, by chromatography and/or fractional crystallization. Any resulting racemates of final products or intermediates can be resolved into the optical antipodes by known methods, e.g., by separation of the diastereomeric salts thereof obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Compounds of the present invention are either obtained in the free form, as a salt thereof, or as prodrug derivatives thereof.

It will also be noted that the substituents of some of the compounds of this invention include isomeric cyclic structures. It is to be understood accordingly that constitutional isomers of particular substituents are included within the scope of this invention, unless indicated otherwise. For example, the term "tetrazole" includes tetrazole, 2H-tetrazole, 3H-tetrazole, 4H-tetrazole and 5H-tetrazole. Compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the α-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non- superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Calm- lngold- Prelog R- S system.

When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids, e.g., acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

The subject invention also includes isotopically-labeled LpxC inhibitors, that are structurally identical to those disclosed above, but for the fact that one or more atoms are replaced by an atom having an atomic mass or mass number different from the atomic mass or mass number usually found in nature. Examples of isotopes suitable for inclusion in the compounds of the invention comprises isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Compounds of the present invention, prodrugs thereof, and pharmaceutically acceptable salts of said compounds and of said prodrugs that contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Isotopically labeled compounds of this invention and prodrugs thereof can generally be prepared by carrying out known or referenced procedures and by substituting a readily available isotopically labeled reagent for a non-isotopically labeled reagent.

The present invention provides novel compounds, pharmaceutical formulations including the compounds, methods of inhibiting UDP-3-O—(R-3-hydroxydecanoyl)-N-acetylglucosamine deacetylase (LpxC), and methods of treating gram-negative bacterial infections.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. For example, deuterium substitution at non-exchangeable hydrocarbon bonds (e.g., C—H) may retard epimerization and/or metabolic oxidation in vivo.

Isotopically-labeled compounds of the invention, i.e. compounds of formula (I), can generally be prepared by conventional techniques known to those skilled in the art or by processes analogous to those described in the accompanying Examples and Preparations Sections using an appropriate isotopically-labeled reagent in place of the non-labeled reagent previously.

The compounds of the invention can be used for treating conditions caused by the bacterial production of endotoxin and, in particular, by gram-negative bacteria and bacteria that use LpxC in the biosynthesis of lipopolysaccharide (LPS) or endotoxin.

The compounds of the invention also are useful in the treatment of patients suffering from or susceptible to pneumonia, sepsis, cystic fibrosis, or urinary track infections. The compounds of the invention also are useful in the conditions that are caused or exacerbated by the bacterial production of lipid A and LPS or endotoxin, such as sepsis, septic shock, systemic inflammation, localized inflammation, chronic obstructive pulmonary disease (COPD) and acute exacerbations of chronic bronchitis (AECB). For these conditions, treatment includes the administration of a compound of the invention, or a combination of compounds of the invention, optionally with a second agent wherein the second agent is a second antibacterial agent or a second non-antibacterial agent.

For sepsis, septic shock, systemic inflammation, localized inflammation, chronic obstructive pulmonary disease (COPD) and acute exacerbations of chronic bronchitis (AECB), preferred second non-antibacterial agents include antiendotoxins including endotoxin receptor-binding antibodies, endotoxin-binding antibodies, antiCD14-binding protein antibodies antilipopolysaccharide-binding protein antibodies and tyrosine kinase inhibitors.

In treatment of serious or chronic respiratory tract infections, the compounds of the present invention may also be used with second non-antibacterial agents administered via inhalation. Preferred non-antibacterial agents used in this treatment include anti-inflammatory steroids, non-steroidal anti-inflammatory agents, bronchodilators, mucolytics, anti-asthma therapeutics and lung fluid surfactants. In particular, the non-antibacterial agent may be selected from a group consisting of albuterol, salbuterol, budesonide, beclomethasone, dexamethasone, nedocromil, beclomethasone, fluticasone, flunisolide, triamcinolone, ibuprofin, rofecoxib, naproxen, celecoxib, nedocromil, ipratropium, metaproterenol, pirbuterol, salneterol, bronchiodilators, mucolytics, calfactant, beractant, poractant alfa, surfaxin and pulmozyme (also called domase alfa).

The compounds of the invention can be used, alone or in combination with a second antibacterial agent for the treatment of a serious or chronic respiratory tract infection including serious lung and nosocomial infections such as those caused by *Enterobacter aerogenes, Enterobacter cloacae, Escherichia coli, Klebsiella pneumoniae, Klebsiella oxytoca, Proteus mirabilis, Serratia marcescens, Stenotrophomonas maltophilia, Pseudomonas aeruginosa, Burkholderia cepacia, Acinetobacter baumanii, Alcaligenes xylosoxidans, Flavobacterium meningosepticum, Providencia stuartii* and *Citrobacter freundi*, community lung infections such as those caused by *Haemophilus Influenzae, Legionella* species, *Moraxella catarrhalis, Enterobacter* species, *Acinetobacter* species, *Klebsiella* species, and *Proteus* species, and infections caused by other bacterial species such as *Neisseria* species, *Shigella* species, *Salmonella* species, *Helicobacter pylori, Vibrionaceae* and *Bordetella* species as well as the infections is caused by a *Brucella* species, *Francisella tularensis* and/or *Yersinia Pestis*.

A compound of the present invention may also be used in combination with other agents, e.g., an additional antibiotic agents that is or is not of the formula I, for treatment of a bacterial infection in a subject.

By the term "combination", is meant either a fixed combination in one dosage unit form, or a kit of parts for the combined administration where a compound of the present invention and a combination partner may be administered independently at the same time or separately within time intervals that especially allow that the combination partners show a cooperative, e.g., synergistic, effect, or any combination thereof.

When used for treating Gram-negative bacteria, the compounds of the present invention can be used to sensitize gram-negative bacteria to the effects of a second agent.

When the compounds of the present invention are used in combination with a second antibacterial agent, non-limiting examples of antibacterial agents may be selected from the following groups:

(1) Macrolides or ketolides such as erythromycin, azithromycin, clarithromycin and telithromycin;
(2) Beta-lactams including penicillin such as penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cephalosporin such as cepalothin, cephapirin, cephradine, cephaloridine, cefazolin, cefamandole, cefuroxime, cephalexin, cefprozil, cefaclor, loracarbef, cefoxitin, cefmetazole, cefotaxime, ceftizoxime, ceftriaxone, cefoperazone, ceftazidime, cefixime, cefpodoxime, ceftibuten, cefdinir, cefpirome, cefepime, and carbapenems such as carbapenem, imipenem, meropenem and PZ-601;
(3) Monobactams such as aztreonam;
(4) Quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin and pazufloxacin;
(5) Antibacterial sulfonamides and antibacterial sulphanilamides, including para-aminobenzoic acid, sulfadiazine, sulfisoxazole, sulfamethoxazole and sulfathalidine;
(6) Aminoglycosides such as streptomycin, neomycin, kanamycin, paromycin, gentamicin, tobramycin, amikacin, netilmicin, spectinomycin, sisomicin, dibekalin and isepamicin;
(7) Tetracyclines such as tetracycline, chlortetracycline, demeclocycline, minocycline, oxytetracycline, methacycline, doxycycline, tegacycline;
(8) Rifamycins such as rifampicin (also called rifampin), rifapentine, rifabutin, bezoxazinorifamycin and rifaximin;
(9) Lincosamides such as lincomycin and clindamycin;
(10) Glycopeptides such as vancomycin and teicoplanin;
(11) Streptogramins such as quinupristin and daflopristin;
(12) Oxazolidinones such as linezolid;
(13) Polymyxin, colistin and colymycin;
(14) Trimethoprim and bacitracin.
(15) Efflux pump inhibitors.

The second antibacterial agent may be administered in combination with the compounds of the present inventions wherein the second antibacterial agent is administered prior to, simultaneously, or after the compound or compounds of the present invention. When simultaneous administration of a compound of the invention with a second agent is desired and the route of administration is the same, then a compound of the invention may be formulated with a second agent into the same dosage form. An example of a dosage form containing a compound of the invention and a second agent is a tablet or a capsule.

When used for treating a serious or chronic respiratory tract infections, the compounds of the invention may be used alone or in combination with a second antibacterial agent administered via inhalation. In the case of inhalation, a preferred second antibacterial agent is selected from a group consisting of tobramycin, gentamicin, aztreonam, ciprofloxacin, polymyxin, colistin, colymycin, azithromycin and clarithromycin.

The language "effective amount" of the compound is that amount necessary or sufficient to treat or prevent an bacterial infection and/or a disease or condition described herein. In an example, an effective amount of the LPXC inhibitor is the amount sufficient to treat bacterial infection in a subject. In another example, an effective amount of the LPXC inhibitor is an amount sufficient to treat a bacterial infection, such as, but not limited to *Pseudomonas aeruginosa* and the like in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a bacterial infection. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

Compounds of the invention may be used in the treatment of states, disorders or diseases as described herein, or for the manufacture of pharmaceutical compositions for use in the treatment of these diseases. Methods of use of compounds of the present invention in the treatment of these diseases, or pharmaceutical preparations having compounds of the present invention for the treatment of these diseases.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, inhalation, topical, transdermal, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraanerial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats a bacterial infection.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

Synthetic Procedure

Compounds of the present invention are prepared from commonly available compounds using procedures known to those skilled in the art, including any one or more of the following conditions without limitation:

Within the scope of this text, only a readily removable group that is not a constituent of the particular desired end product of the compounds of the present invention is designated a "protecting group," unless the context indicates otherwise. The protection of functional groups by such protecting groups, the protecting groups themselves, and their cleavage reactions are described for example in standard reference works, such as e.g., Science of Synthesis: Houben-Weyl Methods of Molecular Transformation. Georg Thieme Verlag, Stuttgart, Germany. 2005. 41627 pp. (URL: http://www.science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide and Derivate" (*Chemistry of Carbohydrates: Monosaccharides and Derivatives*), Georg Thieme Verlag, Stuttgart 1974. A characteristic of protecting groups is that they can be removed readily (i.e., without the occurrence of undesired secondary reactions) for example by solvolysis, reduction, photolysis or alternatively under physiological conditions (e.g., by enzymatic cleavage).

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethyl hexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g., by treating the compounds with an acid or a suitable anion exchange reagent. Internal salts of compounds of the present invention containing acid and basic salt-forming groups, e.g., a free carboxy group and a free amino group, may be formed, e.g., by the neutralization of salts, such as acid addition salts, to the isoelectric point, e.g., with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallization and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

Intermediates and final products can be worked up and/or purified according to standard methods, e.g., using chromatographic methods, distribution methods, (re-) crystallization, and the like.

General Process Conditions

The following applies in general to all processes mentioned throughout this disclosure.

The process steps to synthesize the compounds of the invention can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g., in the $H^+$ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described in Science of Synthesis: Houben-Weyl Methods of Molecular Transformation. Georg Thieme Verlag, Stuttgart, Germany. 2005.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyriolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

The present invention also relates to pro-drugs of a compound of the present invention that are converted in vivo to the compounds of the present invention as described herein. Any reference to a compound of the present invention is therefore to be understood as referring also to the corresponding pro-drugs of the compound of the present invention, as appropriate and expedient.

In accordance with the foregoing the present invention provides in a yet further aspect:

A pharmaceutical combination comprising a) a first agent which is a compound of the invention, e.g. a compound of formula I or any subformulae thereof, and b) a co-agent, e.g. a second drug agent as defined above.

A method as defined above comprising co-administration, e.g. concomitantly or in sequence, of a therapeutically effective amount of a compound of the invention, e.g. a compound of formula I or any subformulae thereof and a co-agent, e.g. a second drug agent as defined above.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time. Fixed combinations are also within the scope of the present invention. The administration of a pharmaceutical combination of the invention results in a beneficial effect, e.g. a synergistic therapeutic effect, compared to a monotherapy applying only one of its pharmaceutically active ingredients.

Each component of a combination according to this invention may be administered separately, together, or in any combination thereof.

The compound of the invention and any additional agent may be formulated in separate dosage forms. Alternatively, to decrease the number of dosage forms administered to a patient, the compound of the invention and any additional agent may be formulated together in any combination. For example, the compound of the invention inhibitor may be formulated in one dosage form and the additional agent may be formulated together in another dosage form. Any separate dosage forms may be administered at the same time or different times.

Alternatively, a composition of this invention comprises an additional agent as described herein. Each component may be present in individual compositions, combination compositions, or in a single composition.

Exemplification of the Invention

The invention is further illustrated by the following examples, which should not be construed as further limiting. The assays used throughout the Examples are accepted. Demonstration of efficacy in these assays is predictive of efficacy in subjects.

GENERAL SYNTHESIS METHODS

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

LIST OF ABBREVIATIONS

Ac acetyl
ACN Acetonitrile
AcOEt/EtOAc Ethyl acetate
AcOH acetic acid
aq aqueous
Ar aryl
Bn benzyl
Bu butyl (nBu=n-butyl, tBu=tert-butyl)
CDI Carbonyldiimidazole
$CH_3CN$ Acetonitrile
DBU 1,8-Diazabicyclo[5.4.0]-undec-7-ene
$Boc_2O$ di-tert-butyl dicarbonate
DCE 1,2-Dichloroethane
DCM Dichloromethane
DiBAl-H Diisobutylaluminum Hydride
DIPEA N-Ethyldiisopropylamine
DMAP Dimethylaminopyridine
DMF N,N'-Dimethylformamide
DMSO Dimethylsulfoxide
EI Electrospray ionisation
$Et_2O$ Diethyl ether
$Et_3N$ Triethylamine
Ether Diethyl ether
EtOAc Ethylacetate
EtOH Ethanol
FC Flash Chromatography
h hour(s)
HATU O-(7-Azabenzotriazole-1-yl)-N,N,N'N'-tetramethyluronium hexafluorophosphate
HBTU O-(Benzotriazol-1-yl)-N,N,N',N'-tetramethyluronium hexafluorophosphate
HCl Hydrochloric acid
HMPA Hexamethylphosphoramide
HOBt 1-Hydroxybenzotriazole
HPLC High Performance Liquid Chromatography
$H_2O$ Water
L liter(s)
LC-MS Liquid Chromatography Mass Spectrometry
LiHMDS Lithium bis(trimethylsilyl)amide
$MgSO_4$ Magnesium Sulfate
Me methyl
MeI Iodomethane
MeOH Methanol
mg milligram
min minute(s)
mL milliliter
MS Mass Spectrometry
$NaHCO_3$ Sodium Bicarbonate
$Na_2SO_4$ Sodium Sulfate
$NH_2OH$ hydroxylamine
Pd/C palladium on charcoal
$Pd(OH)_2$ palladium hydroxide
PG protecting group
Ph phenyl
$Ph_3P$ triphenyl phosphine
Prep Preparative
Rf ratio of fronts
RP reverse phase
Rt Retention time
rt Room temperature
$SiO_2$ Silica gel
$SOCl_2$ Thionyl Chloride
TBAF Tetrabutylammonium fluoride
TEA Triethylamine
TFA Trifluoroacetic acid
THF Tetrahydrofuran
TLC Thin Layer Chromatography
HPLC Methods:
Method A:
HPLC Instrument: Gilson
Column: Waters SunFire™ Prep. C18 OBD™, 5 µm, 30×100 mm.
Solvent: $CH_3CN$ (0.1% TFA); $H_2O$ (0.1% TFA)
Gradient: 0-12 min.: 20-35% $CH_3CN$; 40 mL/min.
Method B:
HPLC Instrument: Gilson
Column: Waters XTerra® Prep MS C18 OBD™, 5 µm, 30×100 mm.
Solvent: $CH_3CN$ (3% n-propanol); $H_2O$ (3% n-propanol)
Gradient: 0-15 min.: 10-90% $CH_3CN$; 20 mL/min.
LC-MS Methods:
Method 1:
LC-MS method with Broad range (5-95%) gradient with acid mobile phase (0.1% Formic Acid).
Electrospray mass spectra (+) and (−), DAD-UV chromatogram 200-400 nm, scan range 120-1500 Da.
Gradient: 5-95% MeCN in 2 min (2 mL/min), 2tt.L injection.
Column: Inertsil C8-3, 3.0cm×33 mm×3.0 µm, 40° C.
Method 2:
LC-MS method with Broad range (5-95%) gradient with neutral mobile phase (5 mM NH4+HCOO—).
Electrospray mass spectra (+) and (−), DAD-UV chromatogram 200-400 nm, scan range 120-1500 Da.

Gradient: 5-95% MeCN in 2 min (2 mL/min), 2 µL injection. Column: Inertsil C8-3, 3cm×33 mm×3.0 µm, 40° C.

Method 3:
GENERAL LC-MS method with acid mobile phase (0.1% Formic Acid) and fast gradient. Electrospray mass spectra (+) and (−), DAD-UV chromatogram 200-400 nm, scan range 120-1500 Da. Gradient: 20-80% McCN in 2 min (2 mL/min), 2 µL injection. Column: Inertsil ODS3, 3 cm×33 mm×3.0 µm, 40° C., Method 4:
LC-MS method for POLAR compounds with acid mobile phase (0.1% Formic Acid) and slow (0-100%) gradient. Electrospray mass spectra (+) and (−), DAD-UV chromatogram 200-400 nm, scan range 120-1500 Da. Gradient: 0-100% MeCN in 2 min (2 mL/min), 2 µL injection. Column: Inertsil ODS3, 3 cm×33 mm×3.0 µm, 40° C.

Method 5:
LC-MS method for POLAR compounds with neutral mobile phase (5mM NH4+HCOO—) and slow (0-100%) gradient. Electrospray mass spectra (+) and (−), DAD-UV chromatogram 200-400 nm, scan range 120-1500 Da. Gradient: 0-100% MeCN in 2 min (2 mL/min), 2 µL injection. Column: Inertsil ODS-3, 3 cm×33 mm×3.0 µm, 40° C.

EXAMPLE 1

N-(1-(1-aminocyclopropyl)-2-(hydroxyamino)-2-oxoethyl)-4-(but-2-ynyloxy)benzamide
(Compound 1)

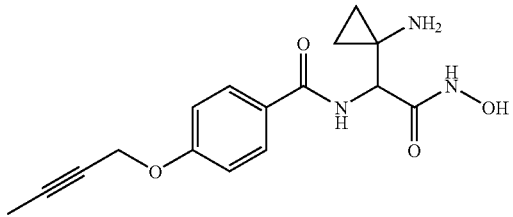

Step 1-A:

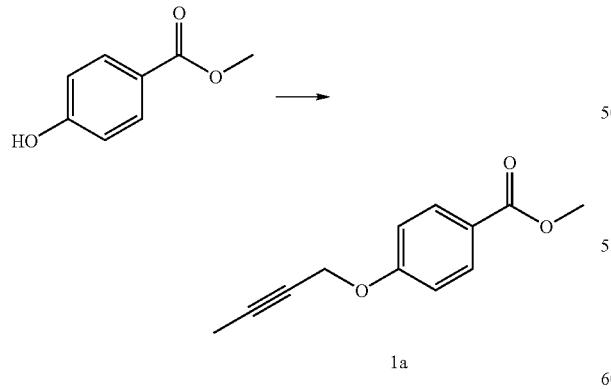

A mineral oil dispersion of sodium hydride (60% by weight, 0.17 g, 7.23 mmol) is added to a solution of methyl-4-hydroxy benzoate (1.0 g, 6.57 mmol) in dimethyl formamide (20 mL) at 0° C. The mixture is stirred for 1 hour after which 1-bromo-2-butyne (0.96 g, 7.23 mmol) is added. The reaction mixture is gradually warmed to room temperature and stirred for overnight. The reaction is quenched with a saturated solution of ammonium chloride and extracted with ethyl acetate. The combined organic layers are washed with brine. The organic layer is dried over MgSO$_4$, filtered and concentrated in vacuo. The residue is chromatographed on silica gel (gradient: EtOAc/hexane; 0:1 to 1:1) to afford 1a (0.79 g). Found m/z ES+=205.

Step 1-B:

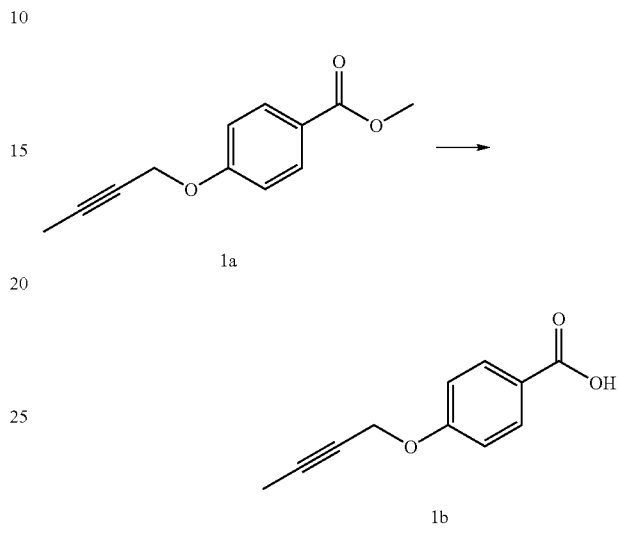

A solution of potassium hydroxide in aqueous 70% methanol (1N, 19 mL) is added to a solution of 1a (0.79g, 3.87 mmol) in THF (20 mL). The reaction is stirred at room temperature for 24 hours. The solvent is then removed under vacuum and then diluted with ethyl acetate (200 mL) then acidify to pH 2 with a 1N solution of HCl (25 mL). The combined organic layers are washed with brine. The organic layer is dried over MgSO$_4$, filtered and concentrated in vacuo to afford 1b (0.71 g). Found m/z ES−=189.

Step 1-C:

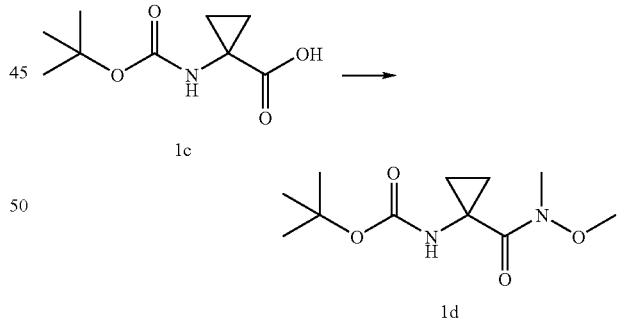

To a solution of 1c (5.0 g, 25.0 mmol) in methylene chloride (40 mL) and DMF (10 mL) is added sequentially HATU (10.5 g, 27.5 mmol) and diisopropylethyl amine (12.0 mL, 75.0 mmol). The reaction is stirred at room temperature for 1 hour after which N,O-dimethyl hydroxylamine HCl salt (2.80 g, 28.0 mmol) is added. The reaction is stirred at room temperature for 24 hours. The reaction is then diluted with ethyl acetate (200 mL) then washed with 10% citric acid, saturated solution of sodium bicarbonate and brine. The organic layer is dried over MgSO$_4$, filtered and concentrated in vacuo. The residue is chromatographed on silica gel (gradient: EtOAc/hexane; 0:1 to 1:1) to afford 1d (5.24 g). Found m/z ES+=245.

Step 1-D:

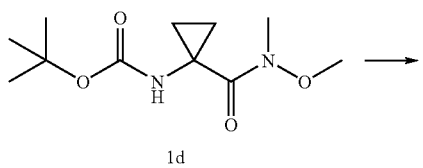

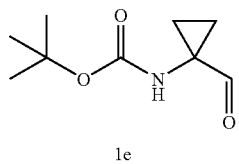

To a solution of 1d (1.39 g, 5.73 mmol) in methylene chloride (20 mL) is cooled to −78° C. and is added dropwise a 1M solution of DiBAl-H in methylene chloride. The reaction is stirred at −78° C. for 3 hours and then quenched with 1N solution of Rochelle salt (25 mL). The aqueous phase is then extracted with methylene chloride. The combined organic layers are dried over MgSO$_4$, filtered and concentrated in vacuo. The residue is chromatographed on silica gel (gradient: EtOAc/hexane; 0:1 to 1:1) to afford 1e (0.57 g). Found m/z ES+=186.

Step 1-E:

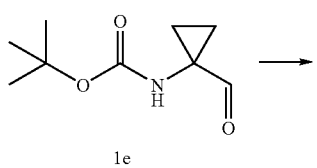

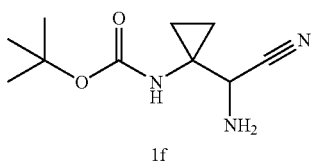

To a solution of compound 1e in water (20 mL) and methanol (16 mL) is added potassium cyanide (401 mg, 6.15 mmol) and ammonium chloride (329 mg, 6.15 mmol). The reaction is then heated up to 45° C. for 12 hours. The reaction is then quenched by addition of a saturated solution of sodium bicarbonate. The aqueous phase is then extracted with ethyl acetate. The combined organic layers are dried over Na$_2$SO$_4$, filtered and concentrated in vacuo to afford 1f (0.20 g). Found m/z ES+=212.

Step 1-F:

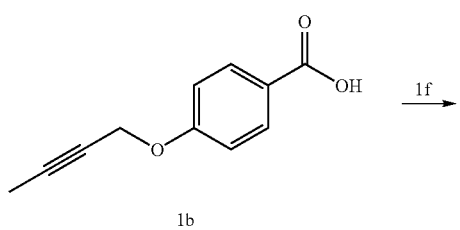

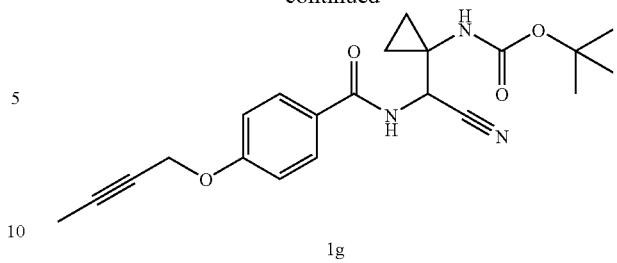

To a solution of 1b (250 mg, 1.31 mmol) in methylene chloride (10 mL) and DMF (10 mL) is sequentially added HATU (500 mg, 1.31 mmol) and diisopropylethyl amine (0.68 mL, 3.93 mmol). The reaction is stirred at room temperature for 1 hour and then if (200 mg, 1.0 mmol) is added to the reaction. The reaction is stirred at room temperature for 24 hours. The reaction is diluted with ethyl acetate (100 mL) and washed with 10% citric acid, saturated solution of sodium bicarbonate and brine. The organic layer is dried over MgSO$_4$, filtered and concentrated in vacuo. The residue is chromatographed on silica gel (gradient: EtOAc/hexane; 0:1 to 1:1) to afford 1g (125 mg). Found m/z ES+=384.

Step 1-G:

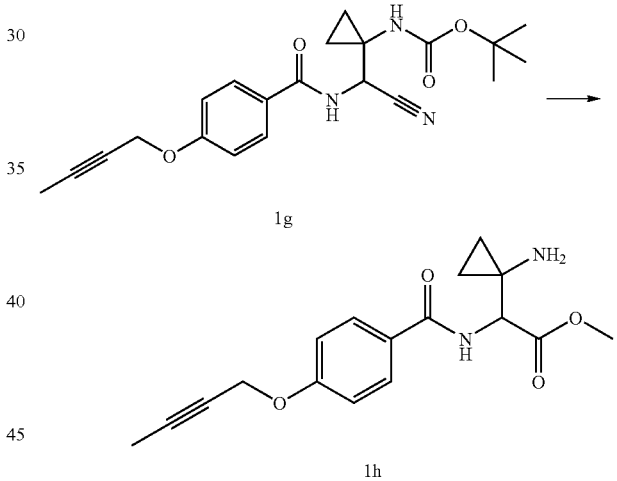

To a solution of 1g (24 mg, 0.0625 mmol) in CH$_2$Cl$_2$ (2 mL) is added a saturated solution of HCl in dry MeOH (2 mL). The reaction is stirred overnight. The reaction is then and concentrated in vacuo to afford 1h (20 mg). Found m/z ES+=317.

Step 1-H:

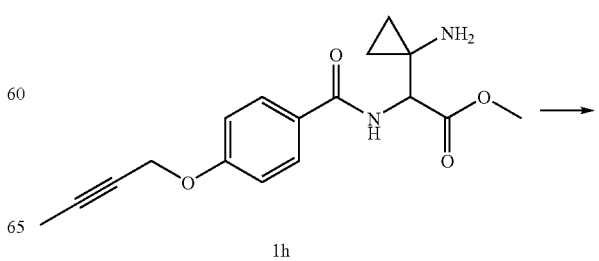

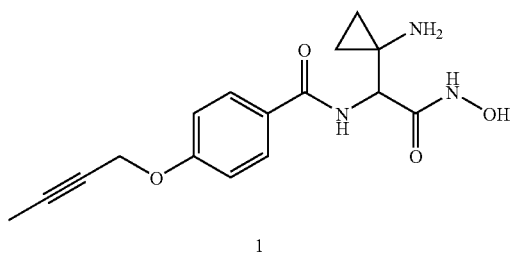

1

To a solution of 1h (20 mg, 0.079 mmol) in methanol (2 mL) and acetonitrile (2 mL) is added a 50% aqueous solution of hydroxylamine (2 mL). After stirring overnight, the crude reaction mixture is directly purified by reverse phase chromatography (Method A) Lyophilization of the product affords title compound 1 (10 mg). LC-MS method 4, Rt=0.90 min.; Found m/z ES+=318 and ES−=316. $^1$H NMR (400 MHz, DMSO-d$_6$, TFA salt): δ=9.16 (s, 1H), 8.46 (d, 1H), 7.88 (d, 2H), 7.07 (d, 2H), 4.83 (s, 2H), 4.29 (d, 1H), 1.84 (s, 3H), 1.25 (m, 1H), 1.03 (m, 1H), 0.92-0.82 (m, 5H).

EXAMPLE 2

N-(3-amino-1-(hydroxyamino)-3-methyl-1-oxobutan-2-yl)-4-(but-2-ynyloxy)benzamide
(Compound 2)

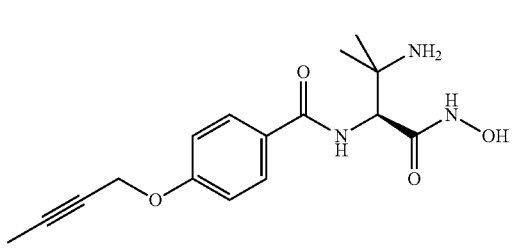

2

Step 2-A:

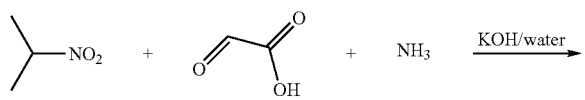

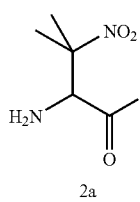

2a

Compound 2a is synthesized according to the procedure described in *J. Chem. Soc. Perkin. Trans.* 1, 1999, 2659-2660.

Step 2-B:

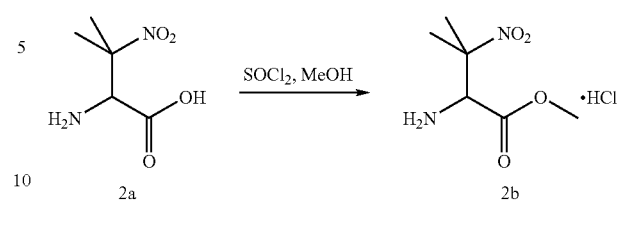

Thionyl chloride (11.0 g, 92.4 mmol) is slowly added to a mixture of 2a (3.00 g, 18.5 mmol) in MeOH (50 mL), and the solution is stirred for 8 days at 70° C. to 75° C. Additional MeOH (5 mL) and SOCl$_2$ (1.0 g) is added to the reaction mixture daily. The volatiles are removed under reduced pressure to afford 3.90 g solid as product 2b.

Step 2-C:

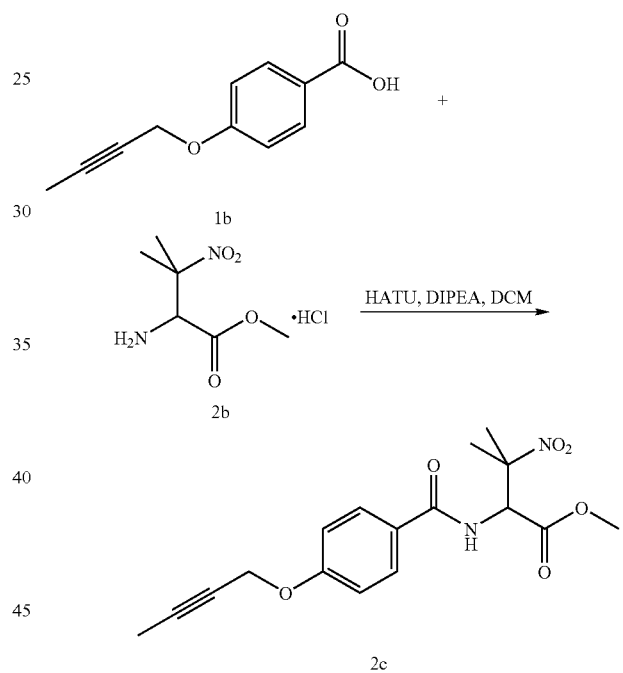

A mixture of 1b (400 mg, 2.11 mmol), 2b (692 mg, 3.26 mmol), HATU (1.20 g, 3.16 mmol) and DIPEA (876 mg, 6.77 mmol) is heated in dichloromethane (20 mL) at 60° C. for 1 day. Volatiles are removed and the residue purified using silica-gel chromatograpy to afford 560 mg product 2c. Found m/z ES+=349, ES−=347.

Step 2-D:

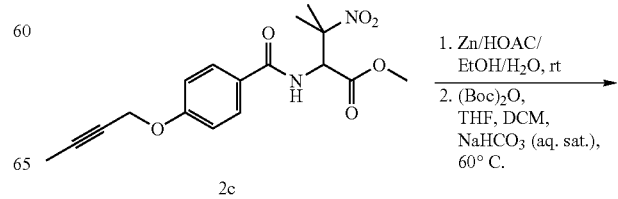

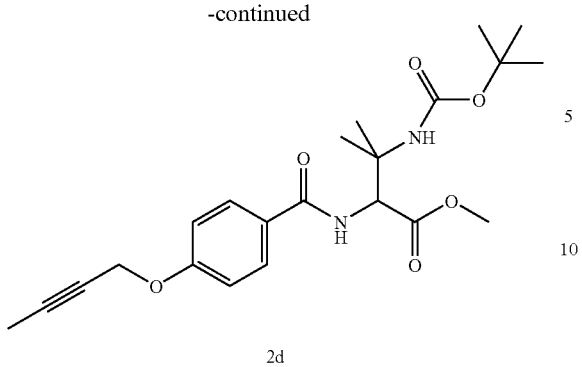

2d

Acetic acid (5.86 g, 9.77 mmol) is added to a mixture of 2c (690 mg, 1.98 mmol), EtOH (25 mL), water (1 mL) and zinc powder(2.82 g, 43.4 mmol). The reaction mixture is stirred at room temperature for 40 min. The solid is removed by filtration and then washed with EtOH. Volatiles are removed from the combined eluents under reduced pressure. THF (10 mL), DCM (10 mL), NaHCO₃ (saturated aq. solution, 15 mL) and (Boc)₂O (950 mg, 4.36 mmol) are added to the evaporation residue and the mixture is stirred at 60° C. for 7 h. The reaction mixture is extracted three times with DCM. The combined DCM layers are dried over Na₂SO₄ and then concentrated. The residue is purified by silica gel chromatography (10% to 30% EtOAc/heptane) to afford 605 mg of 2d. Found m/z ES+=419.

Step 2-E:

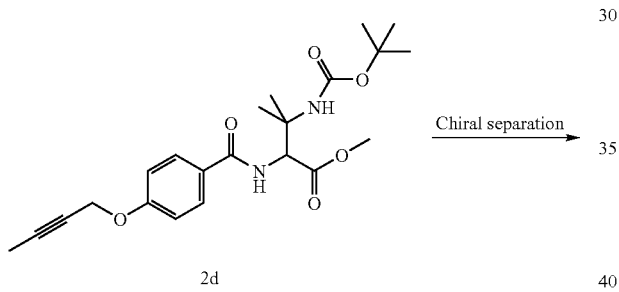

2d → Chiral separation 2e.1 (Enantiomer I)

2e.2 (Enantiomer II)

Chiral separation (Column: ChiralPak AS-H 21 mm×250 mm; 80% Heptane, 20% IPA; 14 mL/min.; 22 min. run) of 2d affords two pure enantiomers 2e.1 (first peak on chiral column) and 2e.2 (second peak on chiral column).

Step 2-F:

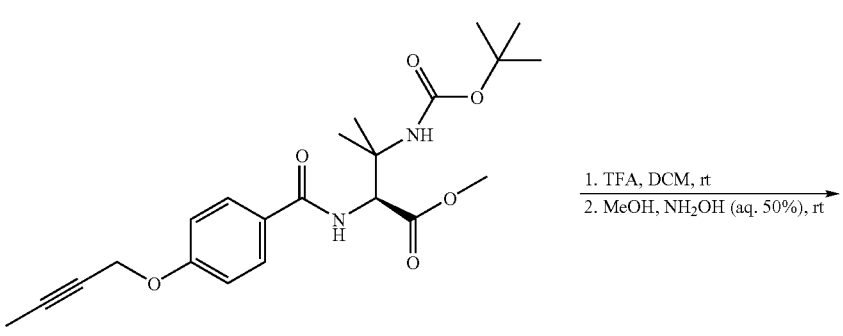

2e.2

1. TFA, DCM, rt
2. MeOH, NH₂OH (aq. 50%), rt

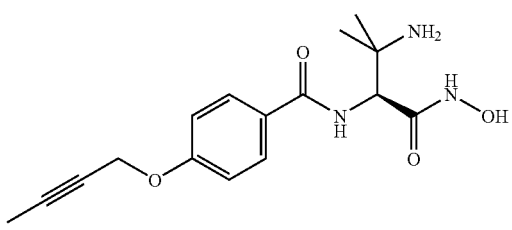

2

Trifluoroacetic acid (2 mL) is added to a solution of 2e.2 (440 mg, 1.05 mmol) in DCM (10 mL) and the reaction mixture is stirred at rt for half an hour. Volatiles are removed under reduced pressure. After adding MeOH (5 mL) and NH$_2$OH (aq. 50%, 3 mL) to the residue, the mixture is stirred overnight at room temperature. The reaction mixture purified by HPLC (HPLC Method A) and the isolated fractions containing 2 is dried by lypholization to afford 391 mg as a TFA salt. Found m/z ES+=320 and ES−=318.

Step 2-G

To a solution of the TFA salt of 2 (153 mg) in ACN/H$_2$O (3:1, 15 mL) is added HCl (1.0 M, aq., 530 uL, 1.5 eq.) and the mixture is subjected to freeze-dry lypholization. Repeat the process again except using 50 uL of HCl (1.0 M, aq.) to give white solid as HCl salt of 2. LC-MS method 1, Rt=0.58 min.; Found m/z ES+=320 and ES−=318. $^1$H NMR (400 MHz, DMSO-d$_6$, HCl salt) δ=11.2 (s, 1H), 9.21 (s, 1H), 8.33 (d, 1H), 8.04 (bs, 3H), 7.06 (d, 2H), 4.83 (q, 2H), 4.68 (d, 1H), 1.83 (t, 3H), 1.33 (s, 3H), 1.29 (s, 3H)

EXAMPLE 3

N-(3-amino-1-(hydroxyamino)-3-methyl-1-oxobutan-2-yl)-4-(but-2-ynyloxy)benzamide (Compound 3)

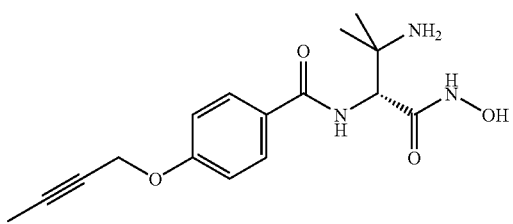

Compound 3, e.g., the other enantiomer of Compound 2, is prepared using the same procedure used to prepare compound 2 from enantiomerically pure starting material 2e.1 prepared in Step 2-E. LC-MS method 1, Rt=0.59 min.; Found m/z ES+=320 and ES−=318. $^1$H NMR (400 MHz, DMSO-d$_6$, HCl salt) δ=11.2 (s, 1H), 9.20 (bs, 1H), 8.39 (bs, 1H), 8.11 (bs, 3H), 7.96 (d, 2H), 7.05 (d, 2H), 4.83 (q, 2H), 4.68 (d, 1H), 1.83 (t, 3H), 1.34 (s, 3H), 1.30 (s, 3H).

EXAMPLE 4

N-(3-amino-1-(hydroxyamino)-3-methyl-1-oxobutan-2-yl)-4-(4,4-dimethylpent-2-ynyloxy)benzamide (Compound 4)

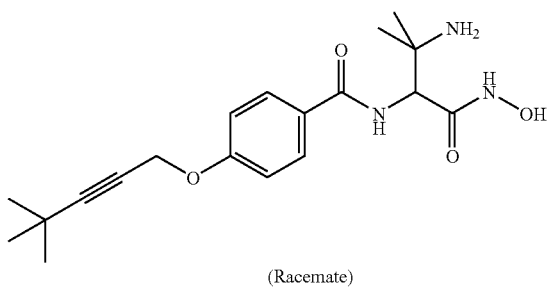
(Racemate)

Step 4-A:

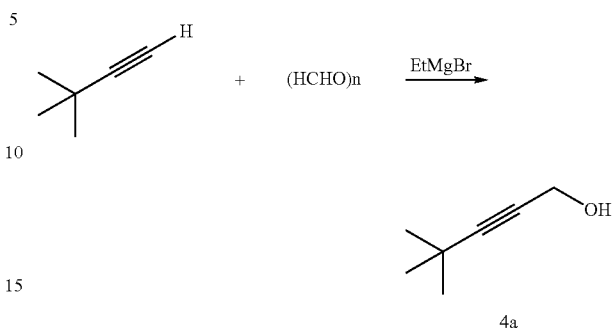

To a solution of 3,3-dimethyl-but-1-yne (1.50 g, 18.3 mmol) in THF (10 mL) is added ethylmagnesium bromide (7.32 mL, 3 M in Et$_2$O, 22.0 mmol) at −78° C., and the mixture is stirred at −78° C. for half hour. Paraformaldehyde (1.02 g) is added to the reaction mixture after which the mixture is stirred at rt for 2 days. Water is added to quench the reaction and the reaction mixture is extracted with DCM three times. The combined DCM layers are dried over Na$_2$SO$_4$, concentrated and purified with silica-gel chromatography (10% to 20% EtOAc/Heptane) to afford 4a (340 mg).

Step 4-B:

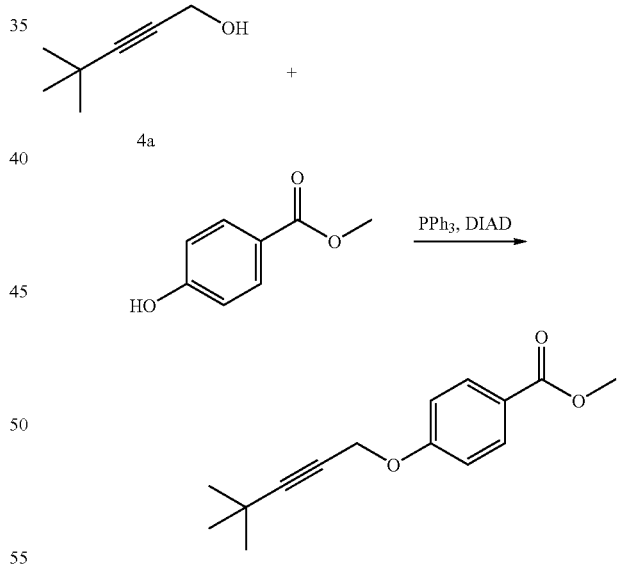

To a mixture of 4a (330 mg, 2.95 mmol), methyl 4-hydroxybenzoate (680 mg, 4.47 mmol), Ph$_3$P (2.36 g, 9.00 mmol) in THF (15 mL) and dichloromethane (15 mL) is added diisopropyl azodicarboxylate (1.92 g, 95%, 9.02 mmol) at 0° C. The mixture is stirred at 0° C. for 3 h. and then at rt overnight. THF and dichloromethane are removed under reduced pressure. The residue is purified with silica-gel chromatography (10% to 20% EtOAc/Heptane) to afford 0.37 g solid as product.

Step 4-C:

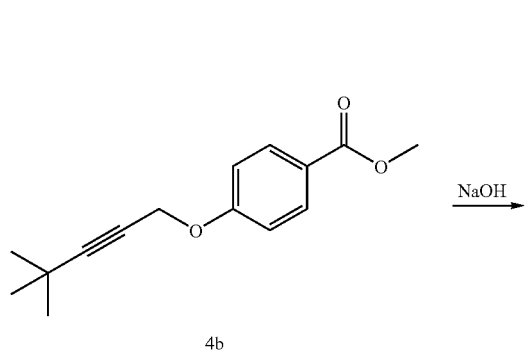

Step 4-D

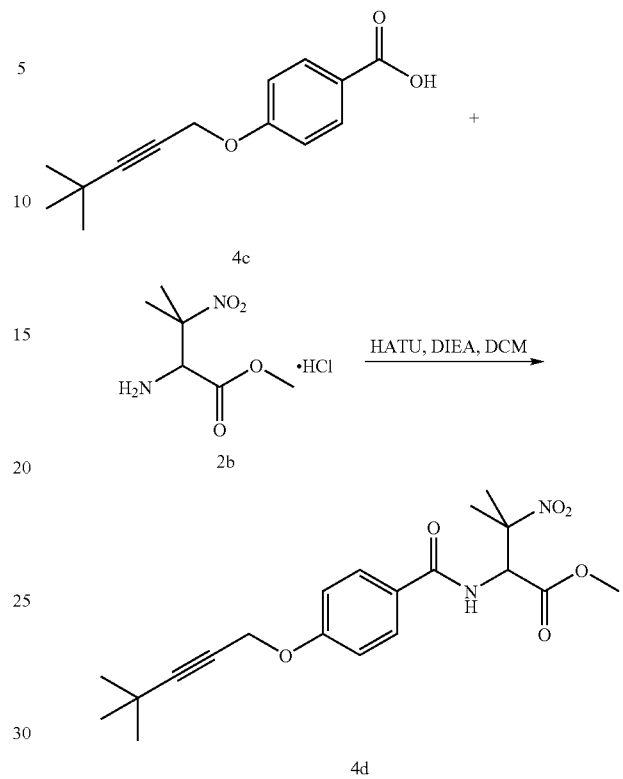

A mixture of 4b (370 mg, 1.50 mmol), NaOH (5 mL, 1 N, aq.), THF (5mL) and MeOH (5 mL) is stirred at rt overnight. THF and MeOH are then removed under vacuum and the residue quenched with HCl (aq. 1N). The solid precipitated out of the solution is filtered, rinsed with water and dried under vacuum to afford 4c (300 mg). Found m/z ES−=231.

Compound 4d is prepared from 4c and 2b by using procedure analogous to the synthesis of 2c in Step 2-C. Found m/z ES+=391 and ES−=389

Step 4-E:

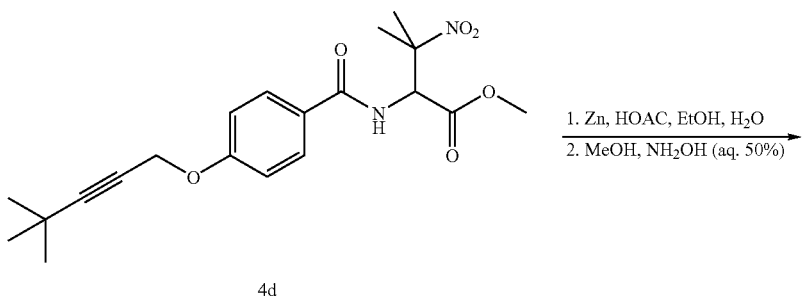

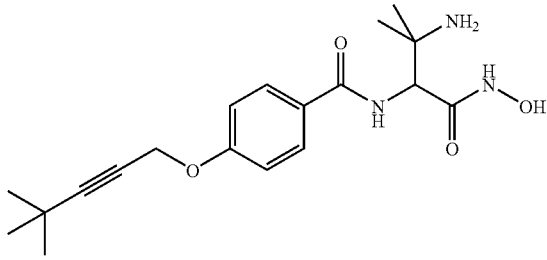

Acetic acid (1.52 g, 25.3 mmol) is added to a mixture of 4d (220 mg, 0.56 mmol), EtOH (10 mL), water (1 mL) and zinc powder (733 mg, 11.3 mmol). The reaction mixture is stirred at rt for 1.5 h. The mixture is filtered and the solid residue is washed with EtOH. The combined filtrate solution is concentrated under partial pressure. To the residue is added MeOH (2 mL) and NH$_2$OH (50%, aq, 1.5 mL), and the mixture is stirred at rt overnight. The reaction mixture is purified using HPLC (HPLC Method A). The fractions containing the TFA salt of 4 are dried by lypholization. The hydrochloride salt of compound 4 is prepared using the conditions of Step 2-G. LC-MS method 2, Rt=0.94 min.; Found m/z ES+=362 and ES−=360. $^1$H NMR (400 MHz, DMSO-c/$_6$, HCl salt) δ=11.2 (s, 1H), 9.20 (s, 1H), 8.35 (d, 1H), 8.05 (bs, 3H), 7.94 (d, 2H), 7.06 (d, 2H), 4.82 (s, 2H), 4.68 (d, 1H), 1.34 (s, 3H), 1.29 (s, 3H), 1.18 (s, 9H)

EXAMPLE 5

N-((1R,2S)-1-amino-1-cyclopropyl-3-(hydroxyamino)-3-oxopropan-2-yl)-4-(but-2-ynyloxy)benzamide (Compound 5)

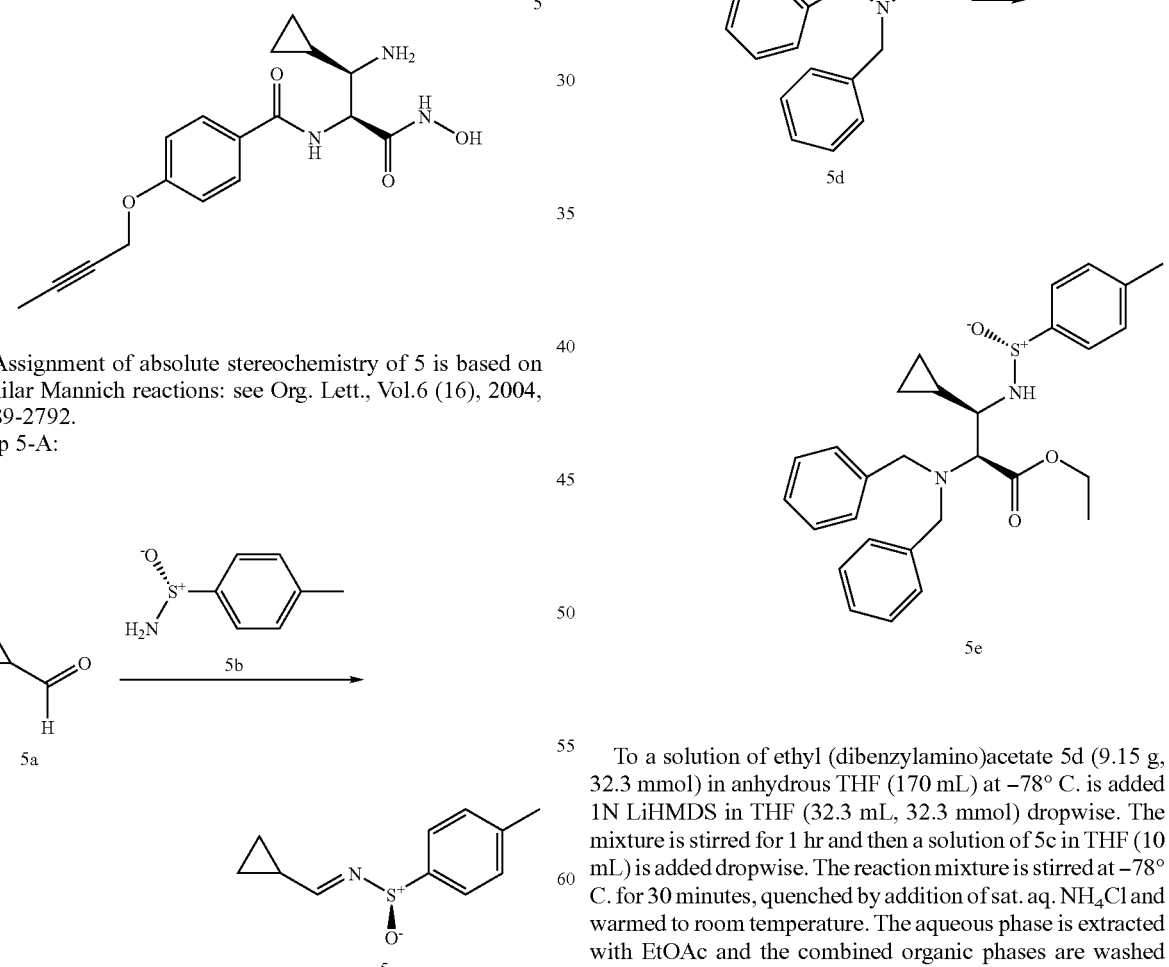

Assignment of absolute stereochemistry of 5 is based on similar Mannich reactions: see Org. Lett., Vol.6 (16), 2004, 2789-2792.

Step 5-A:

A solution of cyclopropane carboxaldehyde 5a (0.902 g, 12.88 mmol), R-(−)-p-toluene sulfonamide 5b (2.0 g, 12.88 mmol) and Titanium (IV) ethoxide (14.7 g, 64.4 mmol) in anhydrous dichloromethane (200 mL) is heated at reflux for 8 hours after which the reaction is cooled to 0° C. and quenched with water (200 mL). The white cake is filtered off, washed with dichloromethane and the combined filtrates concentrated. The crude concentrate is purified by silica gel chromatography (gradient: EtOAc/heptane; 10% to 40%) to give 5c (1.35 g).

Step 5-B:

To a solution of ethyl (dibenzylamino)acetate 5d (9.15 g, 32.3 mmol) in anhydrous THF (170 mL) at −78° C. is added 1N LiHMDS in THF (32.3 mL, 32.3 mmol) dropwise. The mixture is stirred for 1 hr and then a solution of 5c in THF (10 mL) is added dropwise. The reaction mixture is stirred at −78° C. for 30 minutes, quenched by addition of sat. aq. NH$_4$Cl and warmed to room temperature. The aqueous phase is extracted with EtOAc and the combined organic phases are washed with brine, dried over Na$_2$SO$_4$, and concentrated in vacuo. The residue is chromatographed on silica gel (gradient: EtOAc/heptane; 0% to 40%) to afford 5e (3.11 g) as the major isomer. Found m/z ES+=491.

Step 5-C:

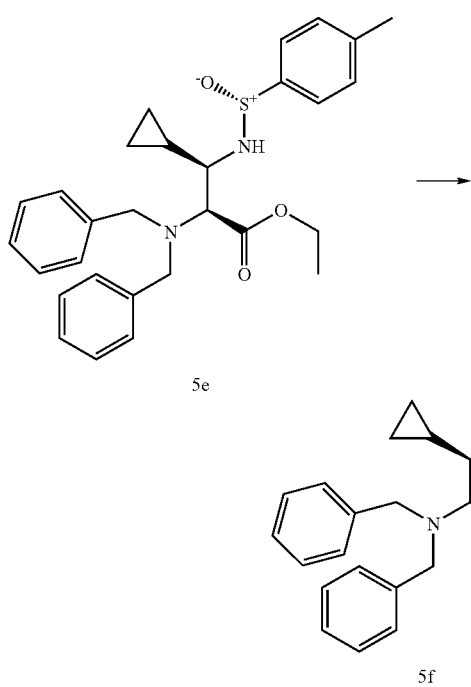

5e

A solution of 5e (2.69 g, 5.49 mmol) in ethanol (130 mL) is cooled to 0° C. and TFA (2.1 mL, 27.45 mmol) is added. The ice bath is removed and the reaction is stirred at room temperature for 2 hours and then concentrated. The residue is chromatographed on silica gel (gradient: EtOAc/heptane; 10% to remove the nonoplar byproduct and then eluted with methanol) to afford 5f (2.5 g) as a TFA salt, which is used in Step 5-D without further purification. Found m/z ES+=353.

Step 5-D:

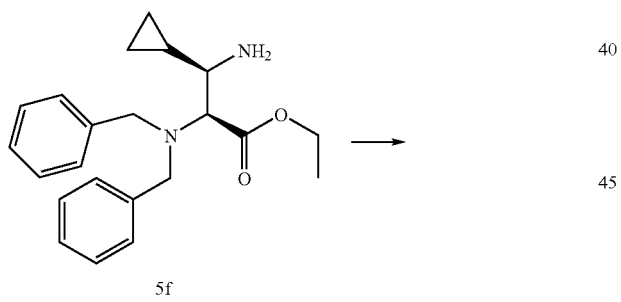

5f

A mixture of 5f (2.5 g, 5.49 mmol) in ethyl acetate (125 mL), Boc₂O (1.44 g, 6.59 mL) and Na₂CO₃ (1.89 g, 17.8 mmol) and water (75 mL) is stirred at room temperature for 24 h, then diluted with water and extracted with ethyl acetate. The organic layer is dried over Na₂SO₄, filtered and concentrated in vacuo to afford 5g (2.53 g), which is used without further purification in Step 5-E. Found m/z ES+=453.

Step 5-E:

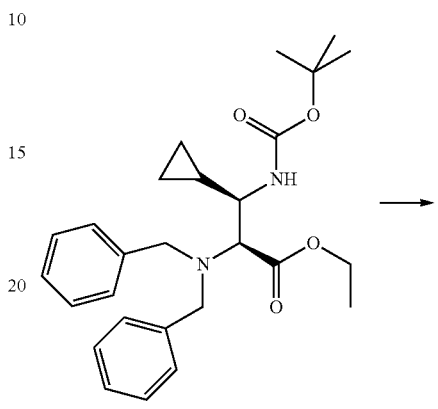

5g

Catalytic amount of Pd(OH)₂ is added to a solution of 5g (2.53 g, 5.59 mmol) in ethanol (75 mL) and hydrogenated under a balloon atmosphere of H₂ for 12 hrs. The mixture is filtered through celite and concentrated to afford 5h (1.54 g), which is used without further purification in Step 5-F. Found m/z ES+=273.

Step 5-F:

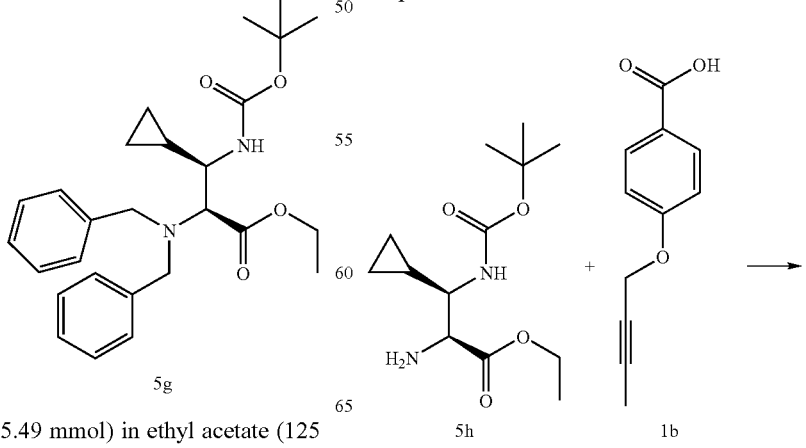

5g     5h     1b

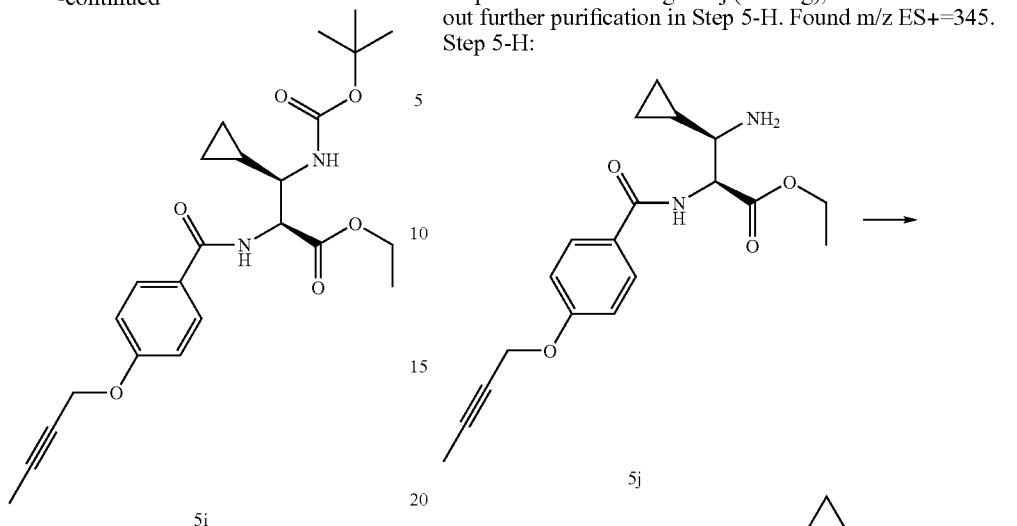

To a solution of 5h (100 mg, 0.37 mmol) and 1b (70.3 mg, 0.37 mmol) in dichloromethane (2.0 mL) is added HATU (169 mg, 0.44 mmol), DIPEA (0.19 mL, 1.11 mmol) and stirred at room temperature for 1 hr. The mixture is directly loaded onto a silica column and eluted with EtOAc/Heptane (5% to 40%) to afford 5i (143 mg). Found m/z ES+=445.

Step 5-G:

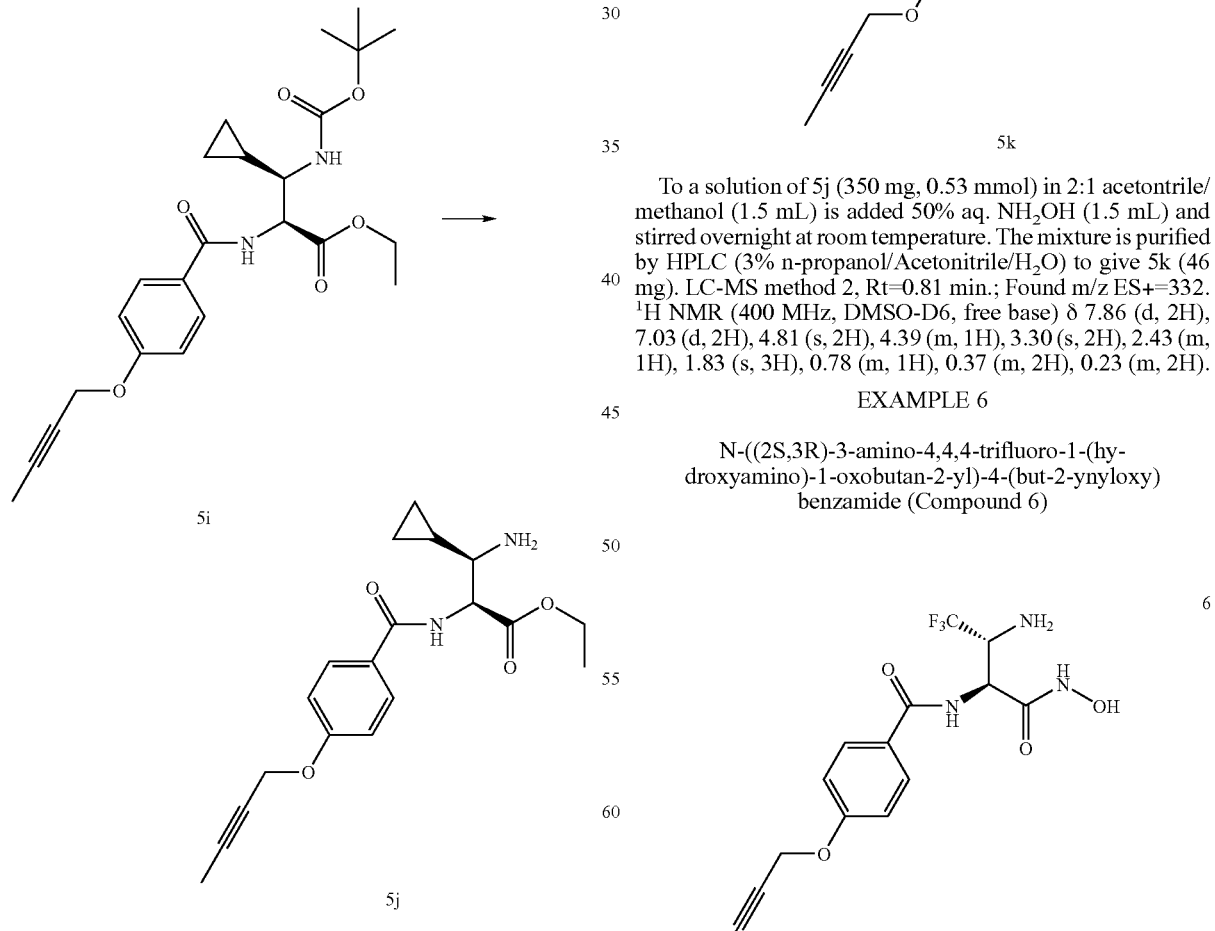

To a solution of 5i (143 mg, 0.322 mmol) in dichloromethane (2 mL) is added TFA (1 mL) at room temperature. The mixture is stirred for 2 hrs after which the solvent is evaporated in vacuo to give 5j (126 mg), which is used without further purification in Step 5-H. Found m/z ES+=345.

Step 5-H:

To a solution of 5j (350 mg, 0.53 mmol) in 2:1 acetontrile/methanol (1.5 mL) is added 50% aq. NH$_2$OH (1.5 mL) and stirred overnight at room temperature. The mixture is purified by HPLC (3% n-propanol/Acetonitrile/H$_2$O) to give 5k (46 mg). LC-MS method 2, Rt=0.81 min.; Found m/z ES+=332. $^1$H NMR (400 MHz, DMSO-D6, free base) δ 7.86 (d, 2H), 7.03 (d, 2H), 4.81 (s, 2H), 4.39 (m, 1H), 3.30 (s, 2H), 2.43 (m, 1H), 1.83 (s, 3H), 0.78 (m, 1H), 0.37 (m, 2H), 0.23 (m, 2H).

EXAMPLE 6

N-((2S,3R)-3-amino-4,4,4-trifluoro-1-(hydroxyamino)-1-oxobutan-2-yl)-4-(but-2-ynyloxy)benzamide (Compound 6)

Assignment of absolute stereochemistry of 6 is based on similar Mannich reactions: see Org. Lett., Vol. 6 (16), 2004, 2789-2792.

Step 6-A:

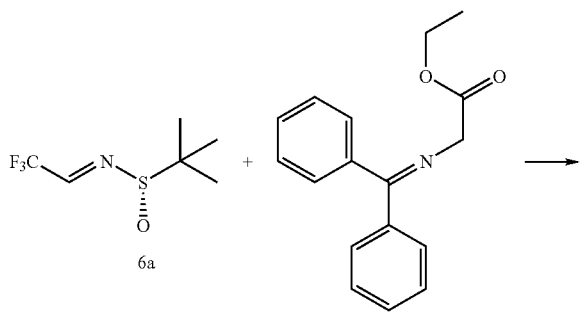

6a + 6b →

Synthesis of sulfinamide 6a is performed as described in Org. Lett., Vol 9, No.4, (2007) 683-685.

To a solution of N-(diphenylmethyleneglycine) ethyl ester 6b (11.68 g, 43.68 mmol) in anhydrous THF (400 mL) at −78° C. is added 1N LiHMDS in THF (43.68 mL, 43.68 mmol) dropwise. The solution is aged for 1 hr and then the reaction mixture of 6a in toluene (27.3 mmol, 53 mL; prepared according to Org. Lett., Vol. 9, No. 4, pp 683-685) is added slowly. The reaction mixture is stirred for 30 minutes at −78° C., quenched by addition of sat. aq. NH₄Cl (150 mL), and warmed to room temperature. The aqueous phase is extracted with EtOAc. The combined organic phases are washed with brine, dried over Na₂SO₄, and concentrated in vacuo. The residue is chromatographed on silica gel (gradient: EtOAc/heptane; 10% to 40%) to afford 6c (2.15 g) as the major isomer. Found m/z ES+=468.

Step 6-B:

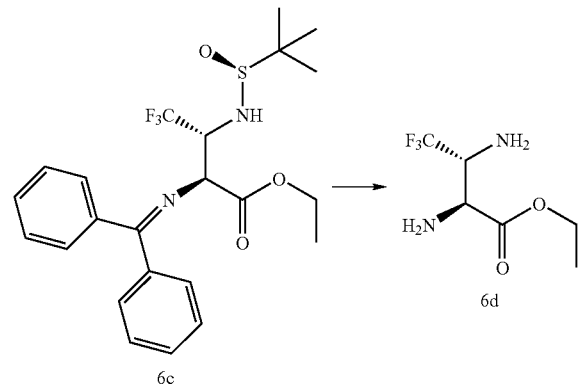

6c → 6d

To a solution of 6c (200 mg, 0.427 mmol) in anhydrous ethanol (1.15 mL) is added 4M HCl in 1,4-dioxane (0.32 mL, 1.28 mmol). The mixture is stirred for 1 hr at room temperature. The volatiles are evaporated under reduced pressure. To the residue is added in sequence THF (2 mL) and aq. 2M HCl (0.43 mL). The reaction is stirred for 2 hrs at room temperature. The reaction mixture is then diluted with aq. 1M HCl (15 mL). The aqueous phase is washed with diethyl ether. The aqueous layer is freeze dried to afford 2d (90 mg; m/z ES+=146).

Step 6-C:

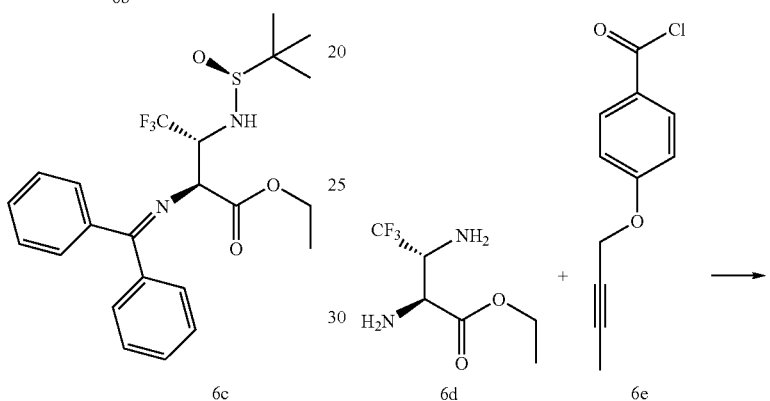

6d + 6e →

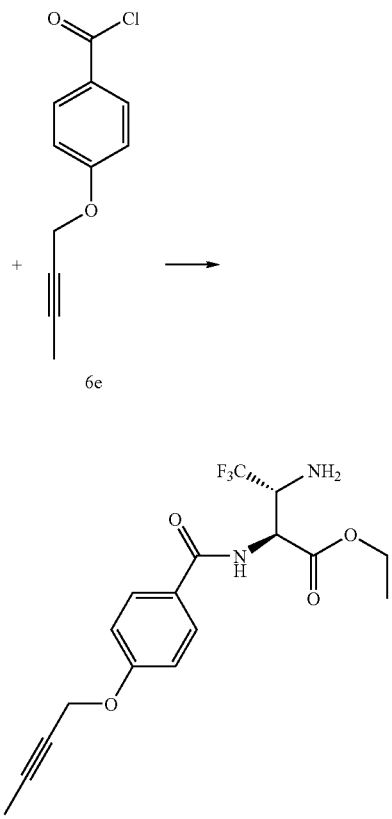

6f

Acid chloride 6e is prepared by refluxing the carboxylic acid 1b (2.0 g, 10.53 mmol), thionyl chloride (10.2 mL) and catalytic amount of DMF in dichloromethane (50 mL) overnight. The volatiles are removed under reduced pressure.

A mixture of 6d (40 mg, 0.147 mmol) in 1,4-dioxane (1.1 mL), 6e (30.65 mg, 0.147 mmol), NaHCO₃ (49.4 mg, 0.588 mmol) and water (1.1 mL) is stirred at room temperature for 36 hrs., then diluted with water and extracted with dichloromethane. The organic layer is dried over Na₂SO₄, filtered and concentrated in vacuo. The crude residue is then purified by HPLC (3% n-propanol/Acetonitrile/H₂O) to give 2f (18 mg). Found m/z ES+=373.

Step 6-D:

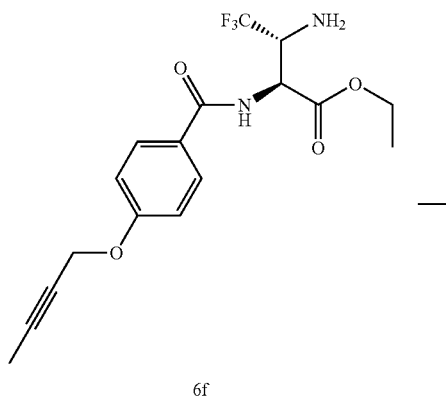

To a solution of 6f (18 mg, 0.05 mmol) in 2:1 acetontrile/methanol (2.25 mL) is added 50% aq. hydroxylamine (2 mL) and stirred overnight at room temperature. The mixture is then purified on HPLC (3% n-propanol/Acetonitrile/H$_2$O) to give 6 (5 mg). LC-MS method 2, Rt=0.96 min.; Found m/z ES+=360. $^1$H NMR (400 MHz, MeOD, free base) δ 7.84 (d, 2H), 7.03 (d, 2H), 5.00 (d, 1H), 4.73 (s, 2H), 3.91 (m, 1H), 1.81 (s, 3H).

EXAMPLE 7

N-((2S,3R)-3-amino-1-(hydroxyamino)-1-oxobutan-2-yl)-4-(but-2-ynyloxy)cyclohexanecarboxamide
(Compound 7)

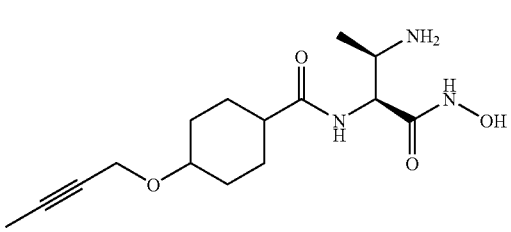

Step 7-A:

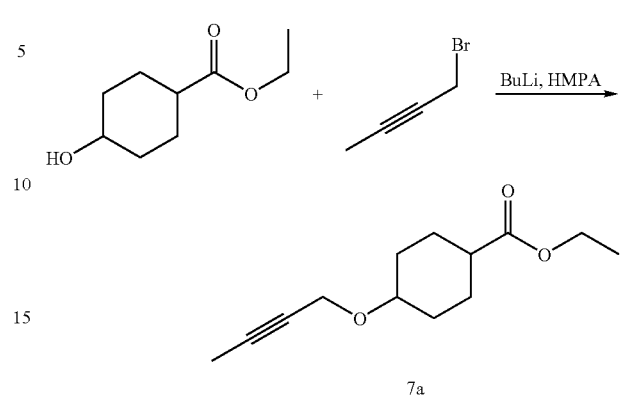

To a solution of 4-hydroxyl-cyclohexanecarboxylic acid methyl ester (cis and trans, 963 mg, 5.60 mmol) is added LiHMDS (1.6 M in hexane, 3.67 mL, 5.87 mmol) slowly at −78° C. Then, HMPA (5.0 g) is added to the mixture and the mixture is stirred at −78° C. for 1 h. To the reaction mixture is added 1-bromo-but-2-yne (1.12 g, 8.42 mmol), and the mixture is stirred at −78° C. for 2 h and rt overnight. Aqueous NH$_4$Cl (10 mL) solution is added to quench the reaction. The mixture is then extracted with DCM three times. The DCM layers are combined, dried over Na$_2$SO$_4$, concentrated followed by silica-gel chromatography (10% EtOAc/Heptane) to afford 7a (442 mg). Found m/z ES+=225.

Step 7-B:

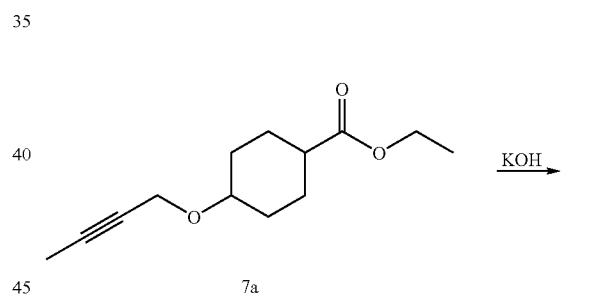

A solution of potassium hydroxide in aqueous 70% methanol (1N, 5 mL) is added to a solution of 7a (0.35g, 1.56 mmol) in THF (5 mL). The reaction is stirred at room temperature for 24 hours. The solvent is then removed under vacuum. The residue is diluted with ethyl acetate (100 mL) and then acidified to pH 2 with a 1N solution of HCl (10 mL). The combined organic layers are washed with brine. The organic layer is dried over MgSO$_4$, filtered and concentrated in vacuo to afford 7b (0.29 g). Found m/z ES−=195

Step 7-C:

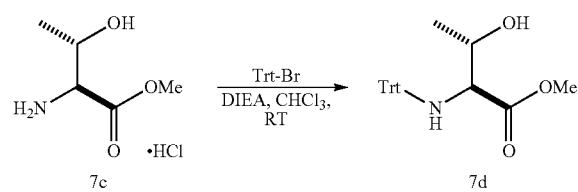

A solution of trityl bromide (41 g, 127 mmol) in CHCl₃ (630 ml) is added dropwise to a stirring solution of 7c (25 g, 147 mmol) and DIEA (55ml, 316 mmol) in CHCl₃ (525 ml) at 0° C., under N₂. After the addition, the reaction is allowed to warm to rt. The reaction could be followed by TLC eluting with EtOAc/Hex (40:60) ($R_f$=0.3). After stirring 12 h, the reaction is concentrated to a brown oil. The crude product is diluted with EtOAc (500 ml) and washed with 0.2 N citric acid (2×100 ml), water (2×100 ml, wash with water until pH=7), brine (100 ml), dried (Na₂SO₄), filtered and concentrated under reduced pressure to yield 44.1 g of 7d. MS(ES+) m/z 376.2.

Step 7-D

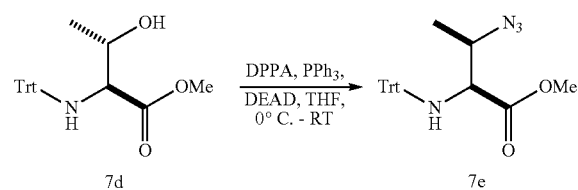

A solution of pure DEAD (50 ml, 304 mmol) in THF (70 ml) is added slowly dropwise over 30 min. to a mechanically stirred solution of PPh₃ (79 g, 301 mmol) in THF (400 ml) at 0° C. under N₂. After 30 min stirring at 0° C. a solid precipitate formed and additional THF (400 ml) is added. Mechanical stirring is adjusted to mix the suspension. A mixture of 7d (75 g, 200 mmol) and DPPA (67 ml, 310 mmol) in THF (460 ml) is added over ~45 min. to the stirred suspension of DEAD and PPh₃. The reaction turns clear during the addition. Stirring continued for 12 h at 0° C. under N₂. The reaction had reached completion by TLC (DCM ($R_f$=0.6), EtOAc/hexanes (1:12) ($R_f$=0.3)) and LCMS. The yellow solution is concentrated to give 307 g of crude material as a red syrup which is purified by column chromatography (4 Kg silica) eluting with DCM/hexanes (1:1) giving 80 g of 7e, which is used without further purification.

Step 7-E

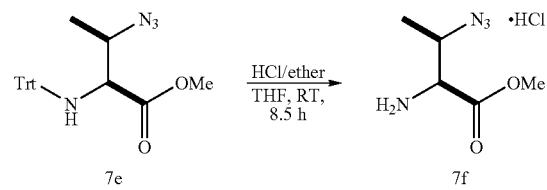

A solution of HCl in ether (60 ml) is added to a solution of 7e (43.2 g, 108 mmol (~65% pure)) dissolved in THF (300 ml) at rt with stirring. A precipitate forms after 5 min. giving a cloudy mixture. The starting material is mostly consumed after 1.5 hours by LCMS, but the reaction seemed to stop over the next 3 h. After 5 h, an additional aliquot of HCl in ether is added to the reaction in one portion. The reaction is complete after 3.5 h. The solids are collected by suction filtration to give 14 g 7f. MS(ES+) m/z 159.3 (C₅H₁₀N₄O₂+H requires 159.08).

Step 7-F

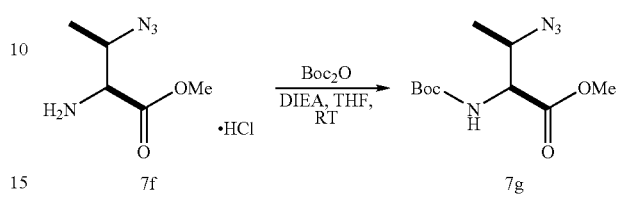

A solution of Boc₂O (22.5 g, 103 mmol) in THF (400 ml) is added to a solution of 7f (13.3 g, 68.4 mmol) and DIEA (36 ml, 205 mmol) in THF (1000 ml) at rt with stirring. Wash in the remaining Boc₂O residue using THF (150 ml). The reaction is complete after 22 h. Enough 2% aqueous NaHSO₄ is added to the reaction to bring the pH to 3, and the THF is removed under reduced pressure at 30-35° C. The aqueous residue is extracted with EtOAc (3×100 ml). The organic layers are combined and washed with water (2×100 ml), brine (1×100 ml), dried over Na₂SO₄, filtered and concentrated. The thick syrup is dissolved in DCM (200 ml) and evaporated to a thick syrup which is dried in vacuo over night to give 20.2 g of 7 g.

Step 7-G

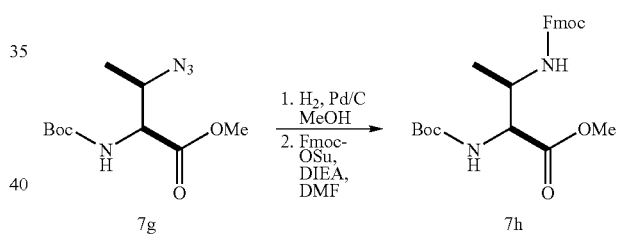

A mixture of 7 g (20.1 g, 68.4 mmol) and 10% Pd on carbon (2 g) in MeOH (350 ml) is deoxygenated and stirred at rt under H₂ at balloon pressure. After 24 h, the reaction had reached completion by TLC. The H₂ atmosphere is exchanged with argon and the Pd/C is removed by filtration. The reaction is concentrated under reduced pressure. The excess Boc₂O caused a small amount of diBoc material to form. This side product is separated from the product by dissolving the residue in EtOAc (100 ml) and extracting the product in 2% aq. NaHSO₄ (2×100 ml). The acidic aqueous layer is basified with solid NaHCO₃ and the product is extracted in EtOAc (7×100 ml). The organic fractions are combined, dried over Na₂SO₄, filtered and concentrated. The thick syrup is dissolved in DCM (200 ml) and evaporated to a thick syrup again. The pure product is dried in vacuo over night to give 9.5 g (~40.9 mmol, ~60% yield) of a sticky glass.

Fmoc-OSu (15.2 g, 45 mmol) is added in portions to a stirred solution of the free amine (9.5 g, ~40.9 mmol) dissolved in THF (200 ml) at 0° C. under argon. A solution of DIEA (8.5 ml, 49 mmol) in THF (50 ml) is added dropwise over 20 min to the stirred reaction at 0° C. under argon. The reaction is complete after 30 min. by TLC. The reaction is concentrated under reduced pressure. The residue is dissolved in EtOAc (200 ml), washed with water (60 ml), 2% aq.

NaHSO$_4$ (2×60 ml), water (2×60 ml), brine (60 ml), dried over Na$_2$SO$_4$, filtered The thick syrup is dissolved in DCM (200 ml) and evaporated to a glass. The glass solidifies overnight in vacuo to give 23 g (~41 mmol, >100% yield) of 7h with some trapped solvent.

Step 7-H

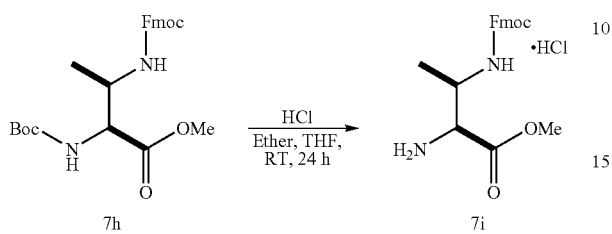

A solution of HCl in ether (600 ml) is added to a solution of 7ll (22.5 g, 41 mmol) dissolved in THF (150 ml) at rt with stirring. A precipitate formed after 5 min. giving a cloudy mixture. The product can be seen on TLC using DCM/MeOH/water (85:10:5 (R$_f$=0.4)) as the eluent. After 12 h, the solids are collected by suction filtration. After drying in vacuo overnight, 7i (13.75 g) is obtained as a white solid HCl salt.

Step 7-I:

To a solution of 7b (290 mg, 1.48 mmol) in methylene chloride (10 mL) and DMF (1 mL) is sequentially added HATU (618 mg, 1.62 mmol) and diisopropylethyl amine (0.54 mL, 3.93 mmol). The reaction is stirred at room temperature for 1 hour and then 7I(633 mg, 1.62 mmol) is added to the reaction. The reaction is stirred at room temperature for 24 hours. The reaction is diluted with ethyl acetate (100 mL) and washed with 10% citric acid, saturated solution of sodium bicarbonate and brine. The organic layer is dried over MgSO$_4$, filtered and concentrated in vacuo. The residue is chromatographed on silica gel (gradient: EtOAc/hexane; 0:1 to 1:1) to afford 7j (359 mg). Found m/z ES+=533.

Step 7-J

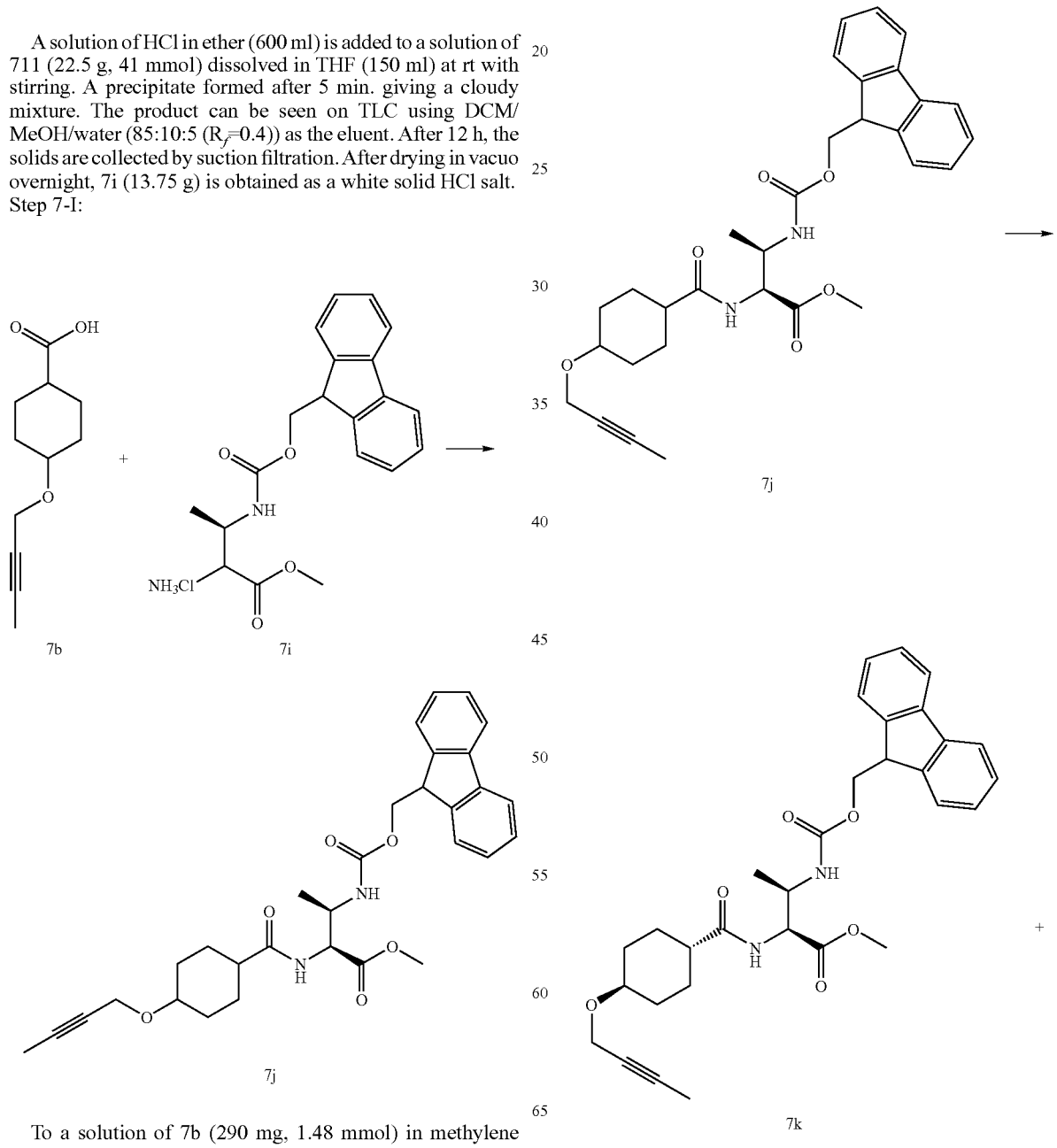

-continued

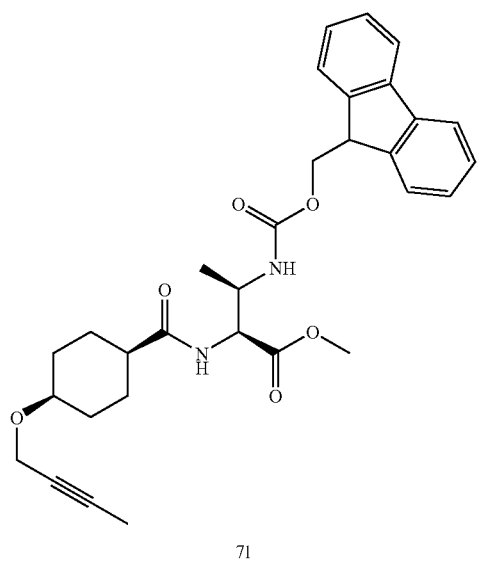

71

Chiral separation (Column: ChiralPak IA-H 21 mm×250 mm; 75% Heptane, 25% IPA; 15 mL/min.; 18 min. run) of 7j affords two diastereomers 7k (first peak on chiral column) and 7l (second peak on chiral column).
Step 7-K:

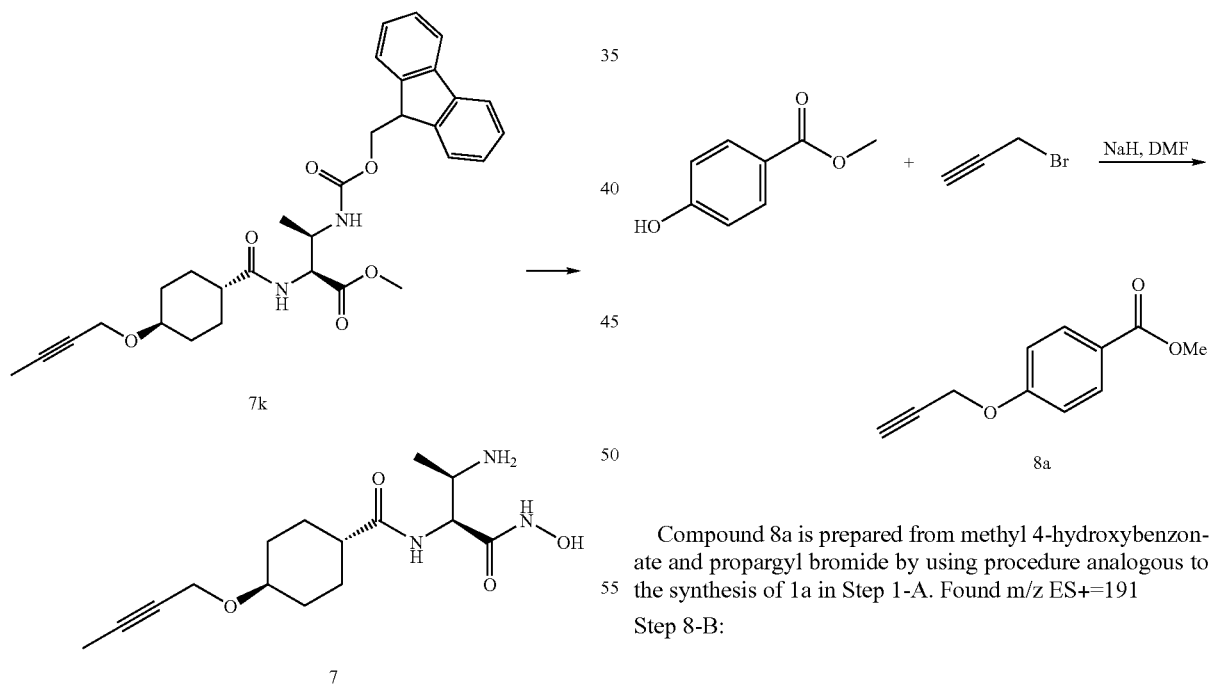

7k

7

To a solution of 7k (67 mg, 0.125 mmol) in methanol (1 mL) and acetonitrile (2 mL) is added a 50% aqueous solution of hydroxylamine (1.25 mL) and piperidine (0.07 mL, 0.625 mmol). After stirring overnight, the crude reaction mixture is directly purified by reverse phase chromatography (Method A). Lyophilization of the product affords title compound 7 (12 mg). LC-MS method 4, Rt=0.69 min.; Found m/z ES+=312 and ES−=310. $^1$H NMR (400 MHz, DMSO-$d_6$, TFA salt): δ=10.0 (s, 1H), 9.12 (s, 1H), 8.15 (d, 1H), 7.85 (s, 2H), 4.28 (t, 1H), 4.09 (s, 2H), 2.05 (t, 1H), 2.02 (d, 2H), 1.91-1.80 (m, 2H), 1.83 (s, 3H), 1.37-1.27 (m, 2H), 1.15-1.03 (m, 5H).

EXAMPLE 8

N-(3-amino-1-(hydroxyamino)-3-methyl-1-oxobutan-2-yl)-4-(4-hydroxy-4-methylpent-2-ynyloxy)benzamide (Compound 8)

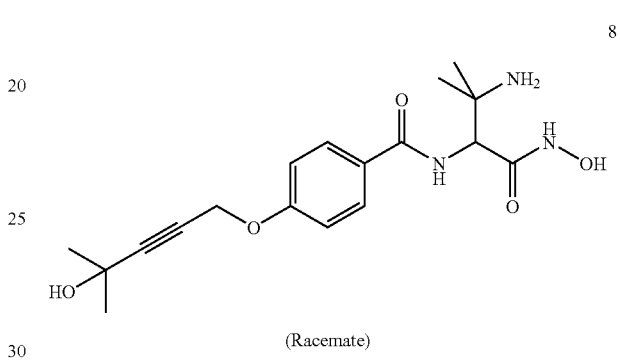

8

(Racemate)

Step 8-A:

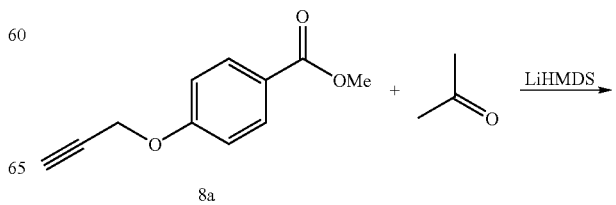

8a

Compound 8a is prepared from methyl 4-hydroxybenzonate and propargyl bromide by using procedure analogous to the synthesis of 1a in Step 1-A. Found m/z ES+=191
Step 8-B:

8a

-continued

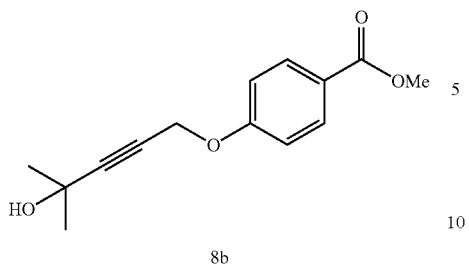
8b

To a solution of 8a (200 mg, 1.05 mmol) in THF (5 mL) is added LiHMDS (1 M in THF, 1.11 mL, 1.11 mmol) and the mixture is stirred at −78° C. for 10 min. Dry acetone (1 mL) is added to the mixture after which the reaction mixture is stirred at rt overnight. More LiHMDS/THF (0.3 mL) is added to the reaction mixture followed by stirring at rt for another 3 h. Water (50 mL) is added to the reaction mixture which is then extraction with DCM three times. The DCM layers are combined, dried over $Na_2SO_4$, concentrated followed by silica-gel chromatography (10% to 30% EtOAc/Heptane) to afford 8 (208 mg).

Step 8-C:

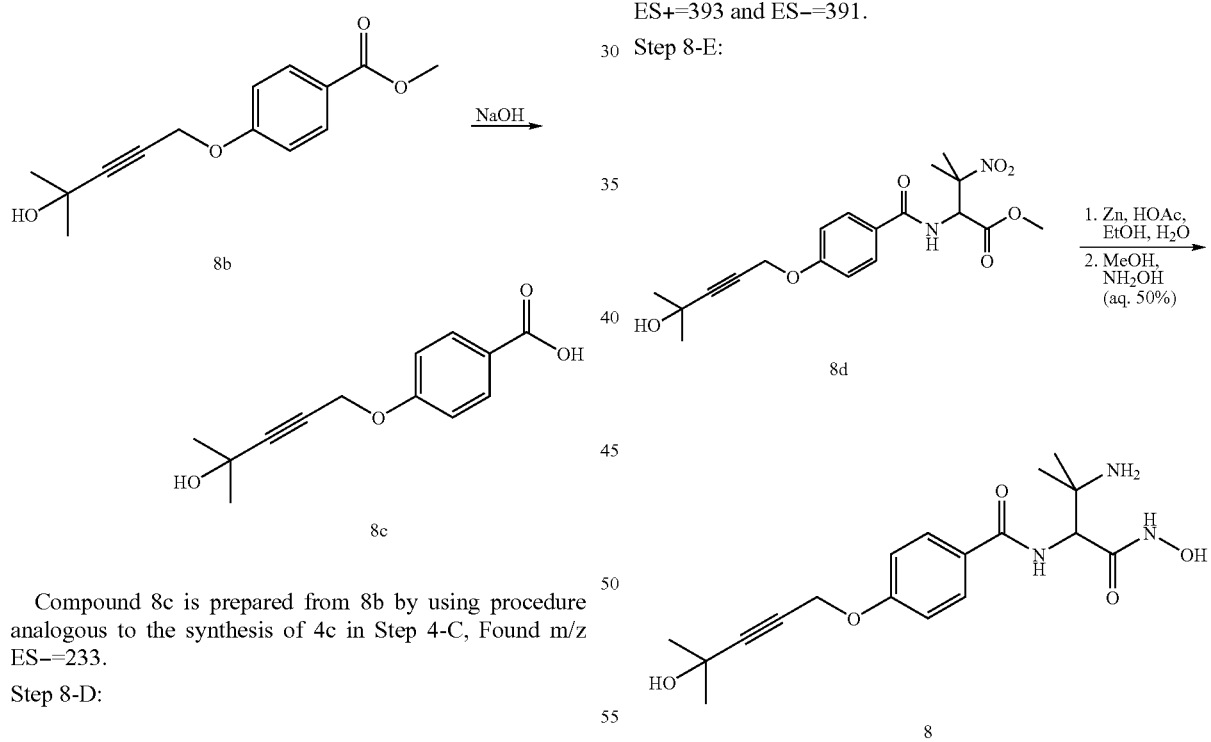

Compound 8c is prepared from 8b by using procedure analogous to the synthesis of 4c in Step 4-C, Found m/z ES−=233.

Step 8-D:

-continued

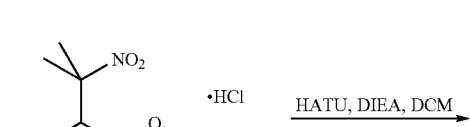

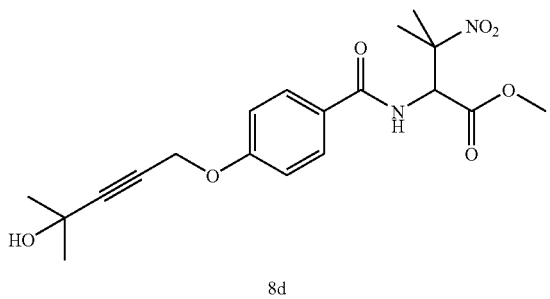
8d

Compound 8d is prepared from 8c by using procedure analogous to the synthesis of 4d in Step 4-D, Found m/z ES+=393 and ES−=391.

Step 8-E:

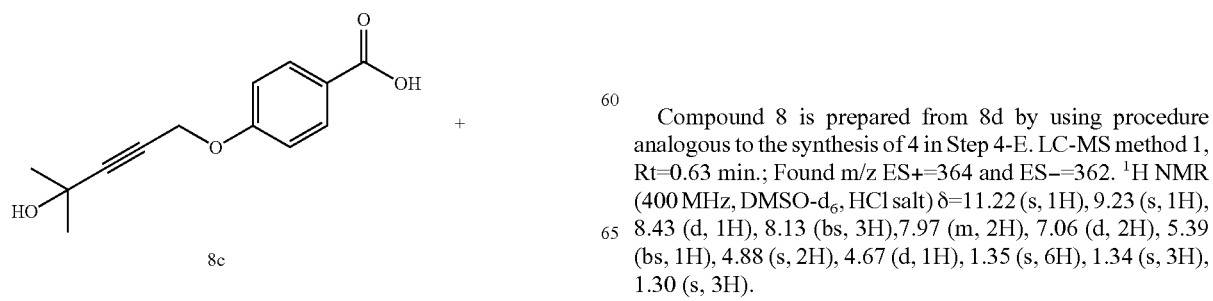
8

Compound 8 is prepared from 8d by using procedure analogous to the synthesis of 4 in Step 4-E. LC-MS method 1, Rt=0.63 min.; Found m/z ES+=364 and ES−=362. $^1$H NMR (400 MHz, DMSO-$d_6$, HCl salt) δ=11.22 (s, 1H), 9.23 (s, 1H), 8.43 (d, 1H), 8.13 (bs, 3H), 7.97 (m, 2H), 7.06 (d, 2H), 5.39 (bs, 1H), 4.88 (s, 2H), 4.67 (d, 1H), 1.35 (s, 6H), 1.34 (s, 3H), 1.30 (s, 3H).

EXAMPLE 9

N-((1S,2R)-2-Amino-1-hydroxycarbamoyl-propyl)-4-but-2-ynyloxy-2-fluoro-benzamide (Compound 9)

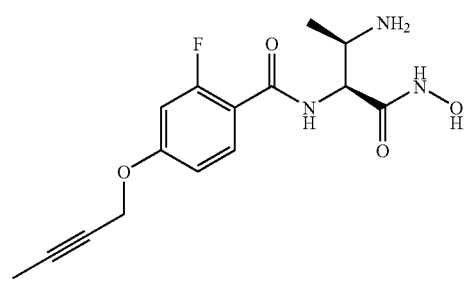

Step 9-A:

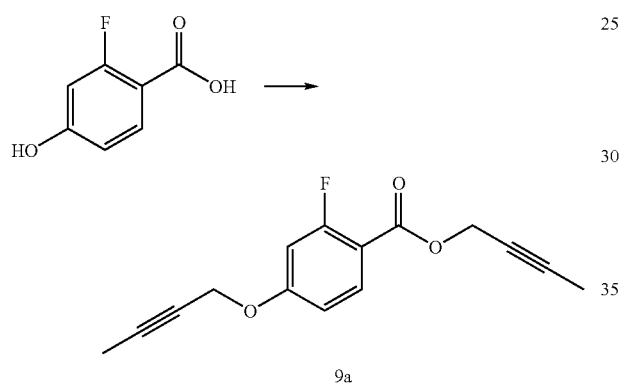

2-Fluoro-4-hydroxy benzoic acid (500 mg, 3.2 mmol) is dissolved in DMF (20 ml), and potassium carbonate (1.79 g, 12.8 mmol) is subsequently added. The mixture is cooled to 0° C., and 1-bromo-2-butyne (1.7 g, 12.8 mmol) is added. The mixture is stirred at RT for 8 hours. The reaction is quenched with a saturated solution of ammonium chloride and extracted with ethyl acetate. The combined organic layers are washed with brine. The organic layer is dried over MgSO$_4$, filtered and concentrated in vacuo, yielding a pale yellow crystalline residue. The residue is resuspended in diethyl ether (10 mL). The suspension is filtered and the resulting ivory crystals dried to afford 9a (0.79 g). Found m/z ES+=261.

Step 9-B:

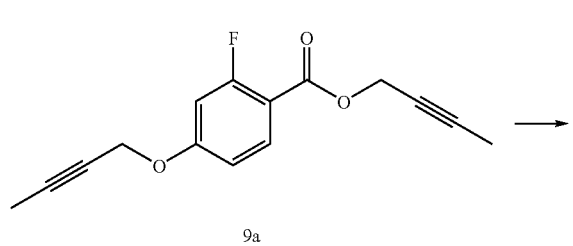

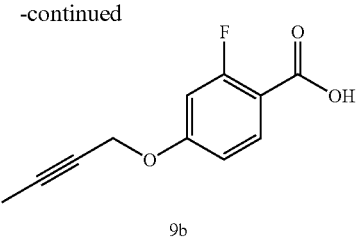

A solution of potassium hydroxide in aqueous 70% methanol (1N, 19 mL) is added to a solution of 9a (0.79 g, 3.0 mmol) in THF (20 mL). The reaction is stirred at room temperature for 24 hours. The solvent is then removed under vacuum and then diluted with ethyl acetate (200 mL) then acidified to pH 2 with a 1N solution of HCl (25 mL). The combined organic layers are washed with brine. The organic layer is dried over MgSO$_4$, filtered and concentrated in vacuo to afford 9b (0.62 g). Found m/z ES−=207.

Step 9-C:

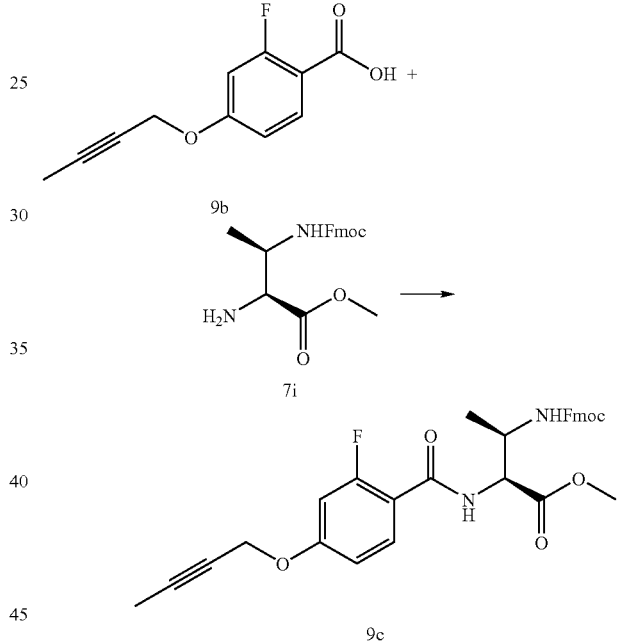

To a solution of 9b (42.57 mg, 0.205 mmol) in DMF (2.0 mL) is added HATU (93.56 mg, 0.246 mmol) and diisopropylethyl amine (0.11 mL, 0.615 mmol). The reaction is stirred at room temperature for 5 minutes and then 7i (80 mg, 0.205 mmol) is added to the reaction. The mixture is stirred at room temperature for 1 hour. The crude residue is purified on HPLC (3% n-propanol/CH$_3$CN/H$_2$O) to afford 9c (0.087 g). Found m/z ES+=545.

Step 9-D:

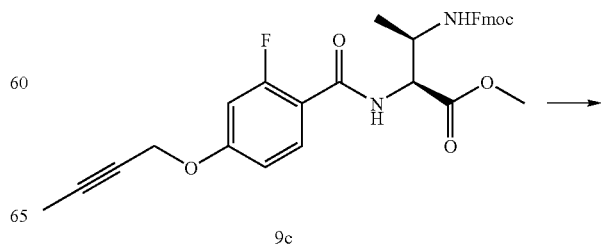

63

-continued

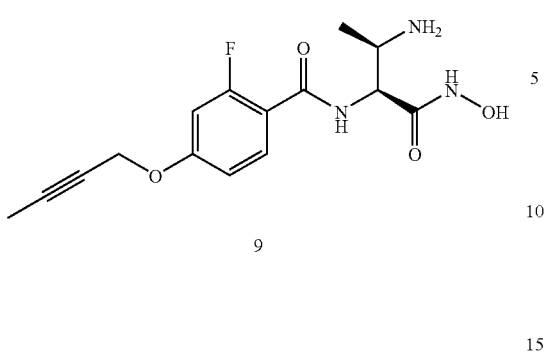

9

To a solution of 9c (87 mg, 0.16 mmol) in methanol (1 mL) and DMF (2 mL) is added 50% NH₂OH (aq) (1.1 mL, 17.5 mmol) followed by piperidine (0.08 mL, 0.799 mmol). The reaction is stirred at room temperature for 2 hours. The reaction mixture is directly loaded and purified on HPLC (3% n-propanol/CH₃CN/H₂O) to afford 9 (29 mg). LC-MS method 2, Rt=0.80 min.; Found m/z ES+=324. ¹H NMR (400 MHz, DMSO-D6, free base) δ 11.14 (s, 1H), 9.15 (s, 1H), 8.23 (m, 1H), 7.98 (s, br, 2H), 7.77 (m, 1H), 6.94 (m, 2H), 4.84 (s, 2H), 4.53 (t, 1H), 3.54 (m, 1H), 1.83 (s, 3H), 1.20 (d, 3H).

EXAMPLE 10

N-((S)-4-Amino-1-hydroxycarbamoyl-butyl)-4-but-2-ynyloxy-benzamide (Compound 10)

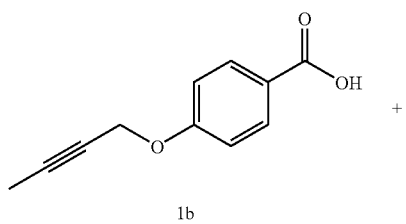

10

Step 10-A:

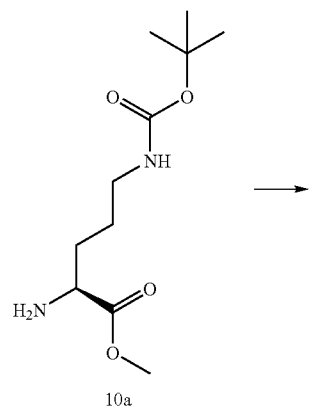

10a

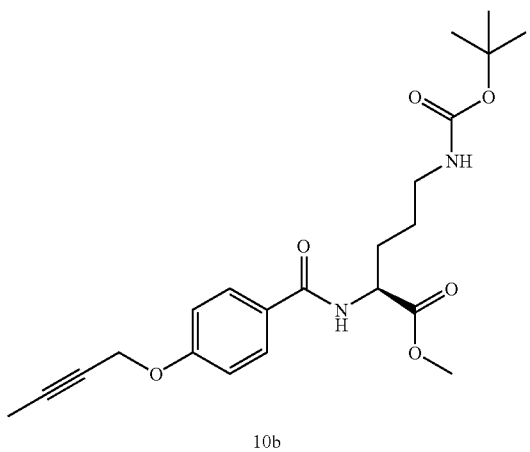

10b

A mixture of 1b (100 mg, 0.526 mmol), 10-a (155 mg, 0.631 mmol), HATU (220 mg, 0.578 mmol) and DIPEA (204 mg, 1.58 mmol) in DCM (5 mL) is stirred at it overnight. Volatiles are removed under reduced pressure and the residue is purified with silica-gel chromatography (10 to 30% EtOAc/Heptane) to afford 10-b (180 mg). Found m/z ES+=419 and ES−=417.

Step 10-B:

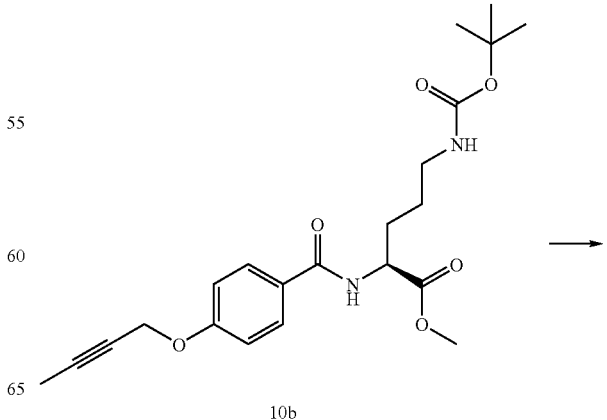

10b

64

-continued

1b

-continued

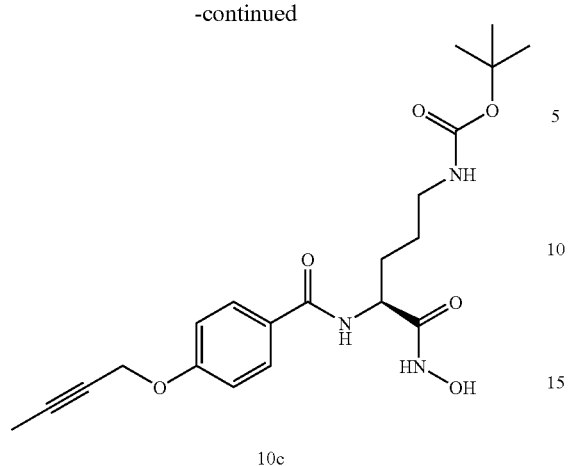

10c

A mixture of 10b (180 mg, 0.43 mmol), NH₂OH (aq. 50%, 1 mL) in MeOH (2 mL) is stirred at rt for 2 days. The reaction mixture is purified with HPLC (Shimadzu system, 10% to 70% ACN/water +0.1% TFA in 12 min.; 40 mL/min.; Phenomex hydro-RP 4u 100×30 mm column) to afford product 10c (70 mg). Found m/z ES+=420 and ES−=418.

Step 10-C:

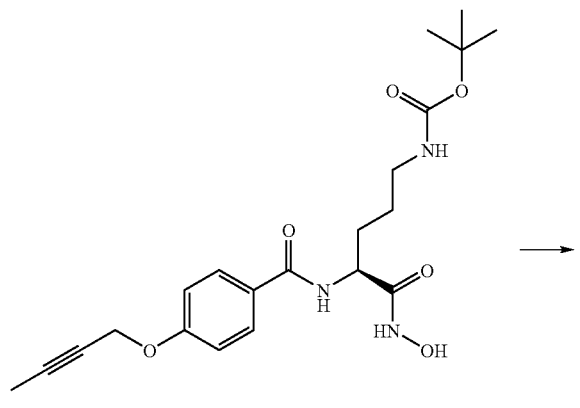

10c

10

A mixture of 10-c (50 mg, 0.119 mmol), TFA (0.2 mL) in DCM (1 mL) is stirred at rt for 1 h. Volatiles are removed under reduced pressure and the residue is purified with HPLC (Gilson system; Sunfire™ Pre C8 OBD 5 um 30×50 mm column; 10% to 60% ACN/water+0.1% TFA in 10 min.; 20 mL/min.) to afford TFA salt of the product 10 (10 mg). LC-MS method 1, Rt=0.56 min. Found m/z ES+=320 and ES−=318. ¹H NMR (400 MHz, MeOD): δ=7.84 (d, 2H), 7.03 (d, 2H), 4.74 (m, 2H), 4.53 (m, 1H), 2.96 (m, 2H), 1.69-1.99 (m, 7H).

EXAMPLE 11

N-((S)-2-Amino-1-hydroxycarbamoyl-2-methyl-propyl)-4-(3-cyclopent-1-enyl-prop-2-ynyloxy)-benzamide (Compound 11)

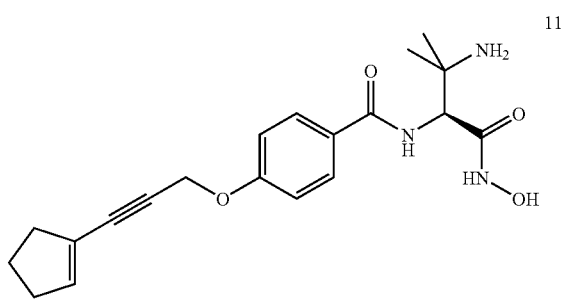 [SMILES: CC(C)(N)[C@H](NC(=O)c1ccc(OCC#CC2=CCCC2)cc1)C(=O)NO]

11

Step 11-A:

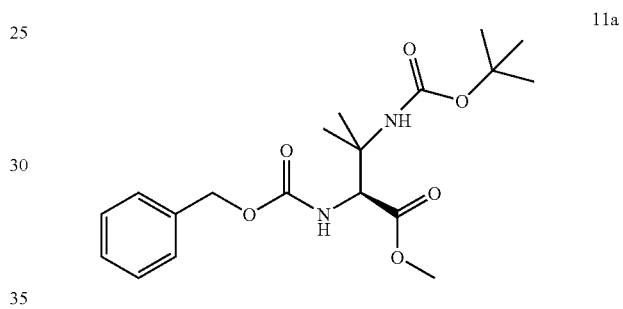

11a

Enantiomerically pure compound 11a is prepared from compound 2a through resolution of the CBZ adduct by using procedures analogous to preparation of compound 2e.2 (Step 2-B to Step 2-E). Found m/z ES−=379.

Step 11-B:

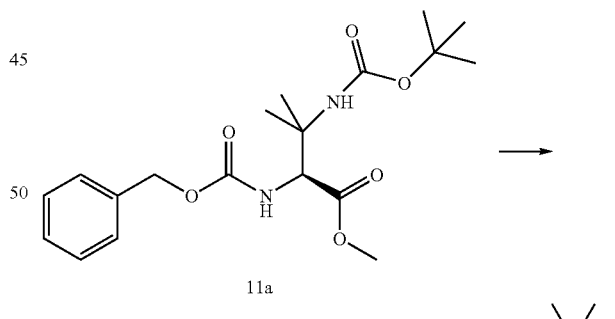

11a

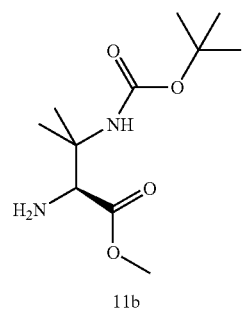

11b

A solution of compound 11a (1.49 g, 3.92 mmol) in MeOH (50 mL) is mixed with Pd/C (10%, 1.67 g) in a round bottom flask which is then connected to a H₂ balloon. The mixture is stirred at rt overnight. Then Pd/C is filtered out through a celite bed, and volatiles in the filtrate are removed under reduced pressure to afford sticky oil as product 11b (0.96 g). Found m/z ES+=247.

Step 11-C:

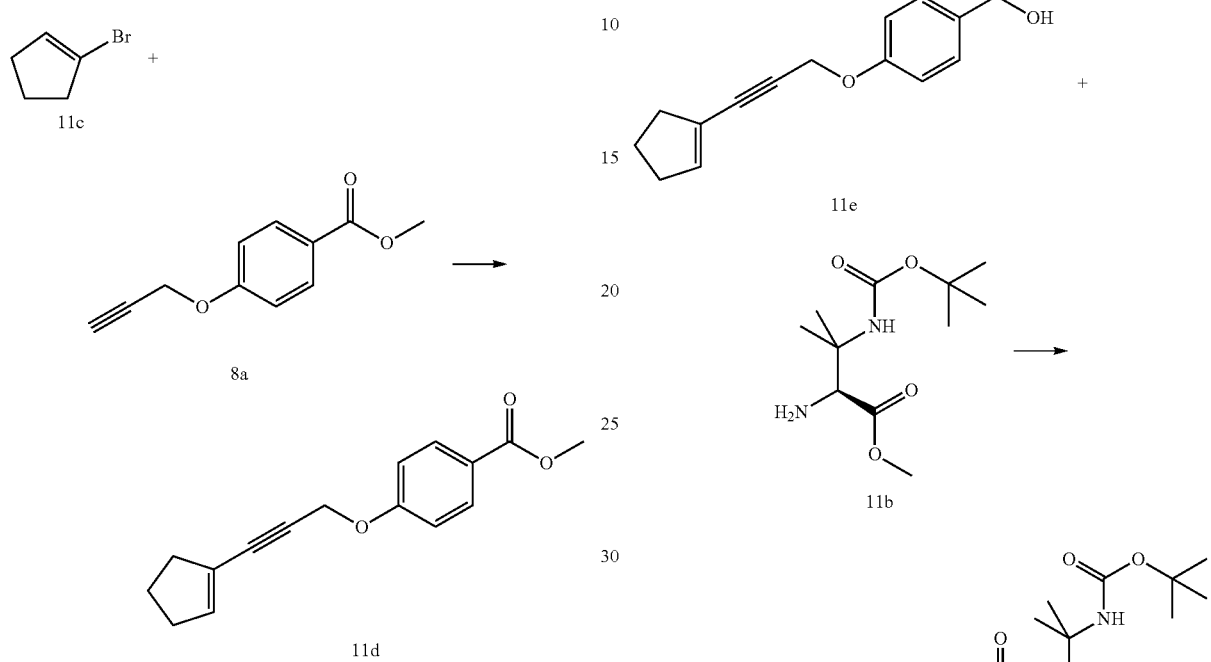

A mixture of 11c (348 mg, 2.37 mmol), 8a (300 mg, 1.58 mmol), Pd(PPh₃)₄ (182 mg, 0.158 mmol) and CuI (60 mg, 0.315 mmol) in TEA (pre-bubbled with N₂ for 1 h) is stirred at rt under N₂ protection for 6 days. Volatiles are then removed under reduced pressure and the residue is purified with silica-gel chromatography (10 to 30% EtOAc/Heptane) to afford 11d (72 mg). Found m/z ES+=257.

Step 11-D:

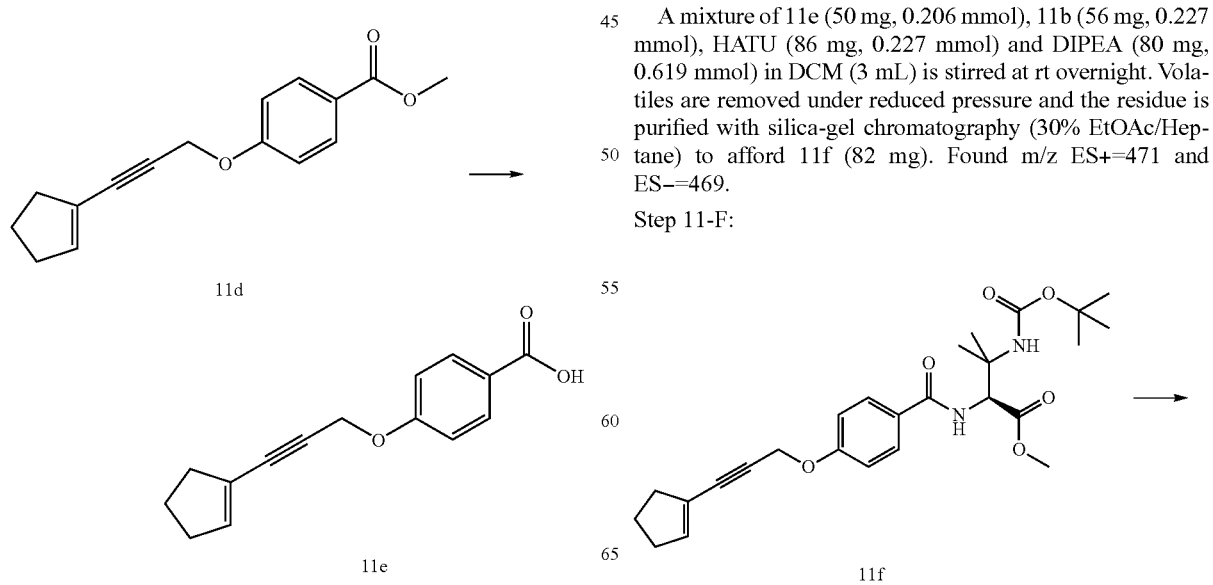

Compound 11e is prepared from 11d by using procedure analogous to the synthesis of 4c in Step 4-C. Found m/z ES+=243 and ES−=241.

Step 11-E:

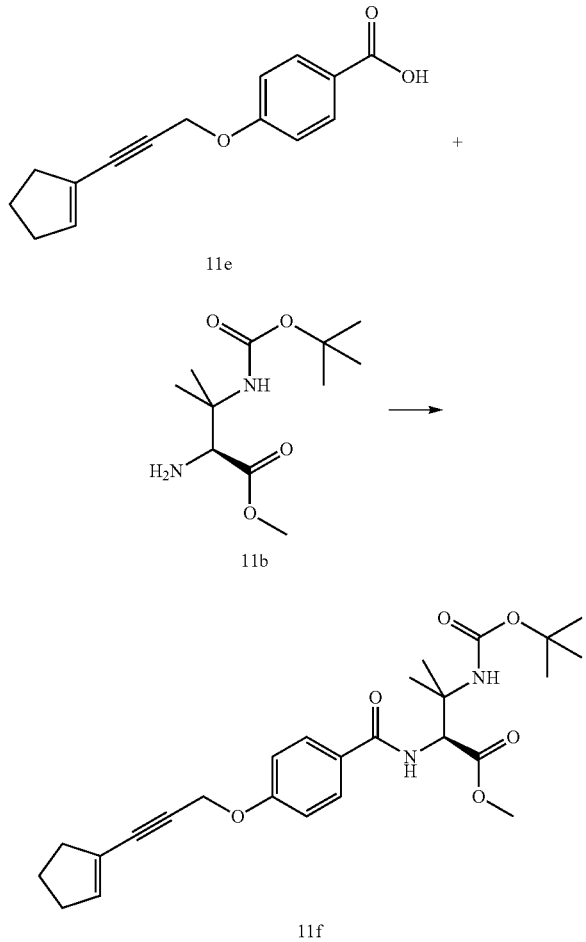 [SMILES: O=C(O)c1ccc(OCC#CC2=CCCC2)cc1 ; COC(=O)[C@@H](N)C(C)(C)NC(=O)OC(C)(C)C ; COC(=O)[C@@H](NC(=O)c1ccc(OCC#CC2=CCCC2)cc1)C(C)(C)NC(=O)OC(C)(C)C]

A mixture of 11e (50 mg, 0.206 mmol), 11b (56 mg, 0.227 mmol), HATU (86 mg, 0.227 mmol) and DIPEA (80 mg, 0.619 mmol) in DCM (3 mL) is stirred at rt overnight. Volatiles are removed under reduced pressure and the residue is purified with silica-gel chromatography (30% EtOAc/Heptane) to afford 11f (82 mg). Found m/z ES+=471 and ES−=469.

Step 11-F:

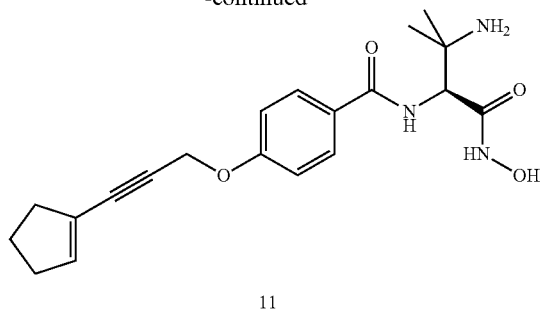

11

The TFA salt of compound 11 is obtained from 11f by using procedure analogous to the synthesis of 2 in Step 2-F. LC-MS method 1, Rt=0.98 min. Found m/z ES+=372 and ES−=370. $^1$H NMR (400 MHz, DMSO-d$_6$, TFA salt) δ=11.2 (s, 1H), 9.24 (s, 1H), 8.30 (d, 1H), 7.98 (s, 3H), 7.91 (d, 2H), 7.09 (d, 2H), 6.11 (m, 1H), 5.04 (s, 2H), 4.69 (d, 1H), 2.36 (m, 4H), 1.84 (m, 2H), 1.33 (s, 3H), 1.28 (s, 3H).

EXAMPLE 12

N-((S)-2-Amino-1-hydroxycarbamoyl-2-methyl-propyl)-4-[3-(3,6-dihydro-2H-pyran-4-yl)-prop-2-ynyloxy]-benzamide (Compound 12)

12

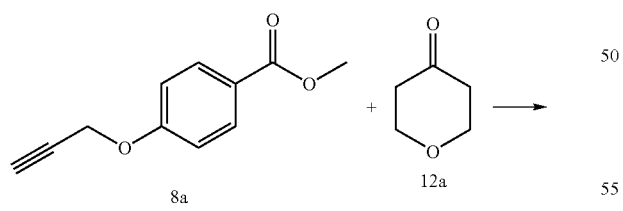

Step 12-A:

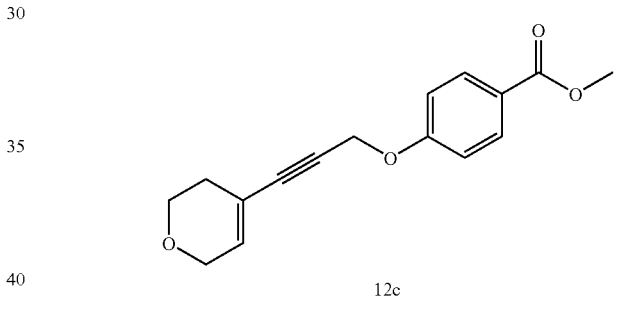

To a solution of 8a (250 mg, 1.31 mmol) in THF (10 mL) is added LiHMDS (1M in THF, 1.71 mL, 1.71 mmol) at −78° C. and the mixture is then stirred at −78° C. (acetone/dry ice bath) for half an hour. 12a (166 mg, 1.97 mmol) added to the mixture after which the reaction mixture is stirred overnight while the temperature raises to rt slowly. NH4Cl (aq. sat) solution is added to quench the reaction mixture. Then THF in the mixture is removed under reduced pressure and the rest solution is extracted with DCM three times. The DCM layers are combined, concentrated and purified with silica-gel chromatography (10 to 30% EtOAc/Heptane) to afford 12-b (356 mg).

Step 12-B:

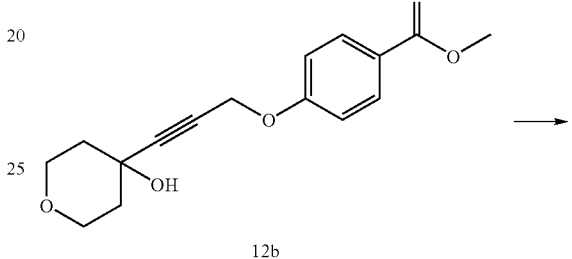

12b

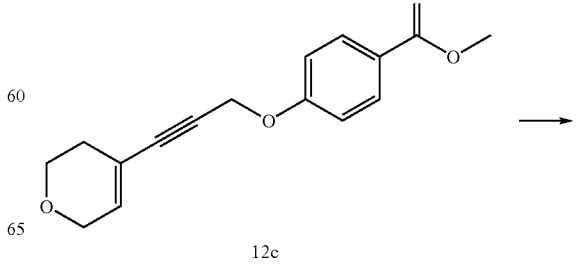

12c

To a mixture of 12b (200 mg, 0.689 mmol) and TEA (209 mg, 2.07 mmol) in DCM (5 mL) is added Methanesulfonyl Chloride (MsCl, 95 mg, 0.827 mmol) at 0° C., The mixture is then stirred at rt for 3 days. Water is added to the mixture after which the reaction mixture is extracted with DCM three times. The DCM layers are combined, concentrated and purified with silica-gel chromatography (10 to 30% EtOAC/Heptane) to afford 12c (180 mg). Found m/z ES+=273.

Step 12-C:

Step 12-E:

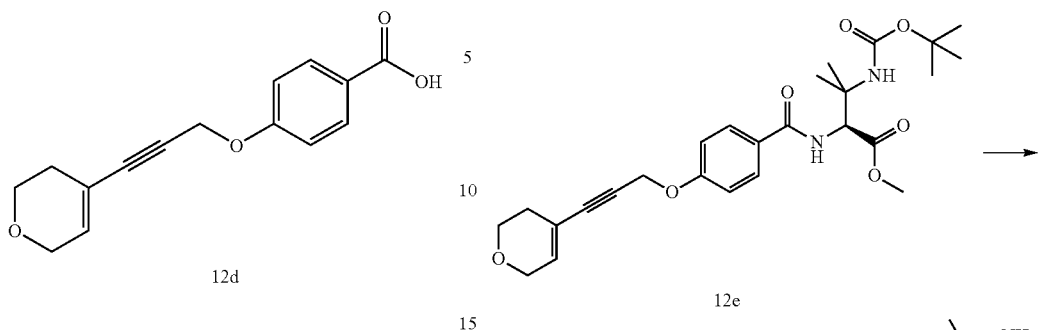

The TFA salt of compound 12 is obtained from 12e by using procedure analogous to the synthesis of 2 in Step 2-F. LC-MS method 1, Rt=0.70 min. Found m/z ES+=388 and ES−=386. ¹H NMR (400 MHz, DMSO-d₆, TFA salt) δ=11.2 (s, 1H), 9.21 (s, 1H), 8.27 (d, 1H), 7.96 (s, 3H), 7.91 (d, 2H), 7.09 (d, 2H), 6.15 (s, 1H), 5.02 (s, 2H), 4.69 (d, 1H), 4.09 (m, 2H), 3.67 (t, 2H), 2.10 (m, 2H), 1.33 (s, 3H), 1.28 (s, 3H).

EXAMPLE 13

N-((S)-2-Amino-1-hydroxycarbamoyl-2-methyl-propyl)-4-(3-d3-methylprop-2-ynyloxy-benzamide (Compound 13)

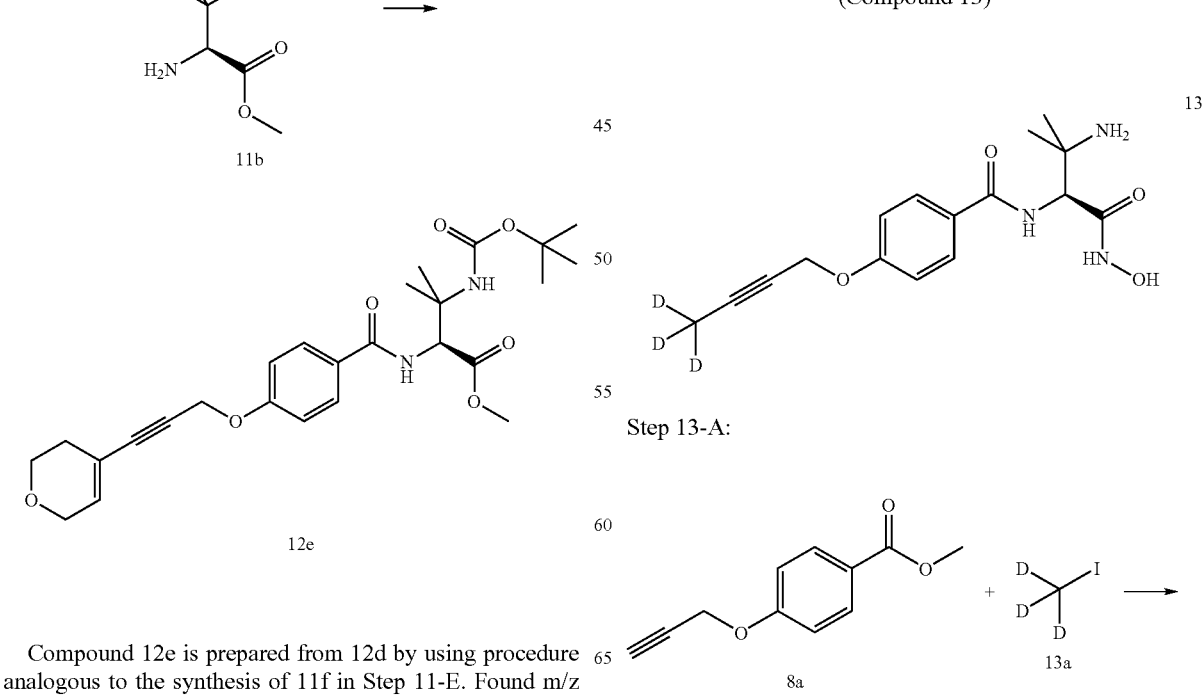

Step 13-A:

-continued

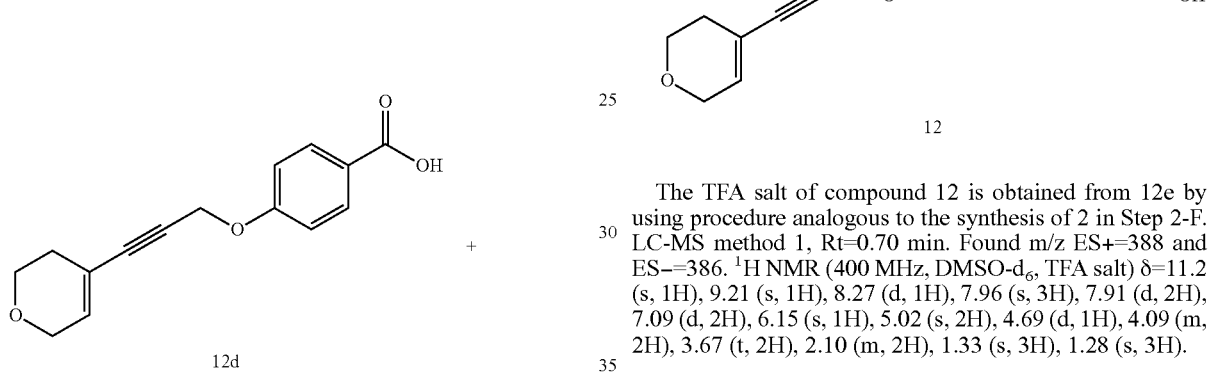

Compound 12d is prepared from 12c by using procedure analogous to the synthesis of 4c in Step 4-C. Found m/z ES−=257.

Step 12-D:

Compound 12e is prepared from 12d by using procedure analogous to the synthesis of 11f in Step 11-E. Found m/z ES+=487 and ES−=485.

-continued

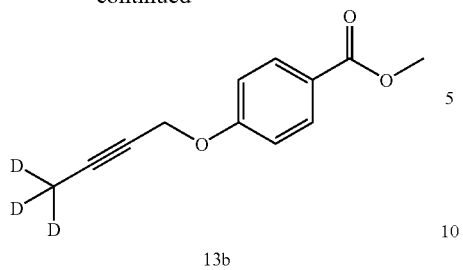
13b

To a solution of 8a (400 mg, 2.10 mmol) in THF (10 mL) is sodium hexamethyldisilazide (NaHMDS, 0.6 M in toluene, 3.86 mL, 2.31 mmol) at −78° C., then the solution is stirred at −78° C. for half an hour. 13a (CD$_3$I, 1.52 g, 10.5 mmol) is added after which the reaction mixture is stirred at rt for 3 days. Water is added to quench the reaction mixture and then THF is removed under reduced pressure. The remaining mixture is extracted with DCM three times. The DCM layers are combined, concentrated and then purified with silica-gel chromatography (5% EtOAc/Heptane) to afford 13b (267 mg). Found m/z ES+=208.

Step 13-B:

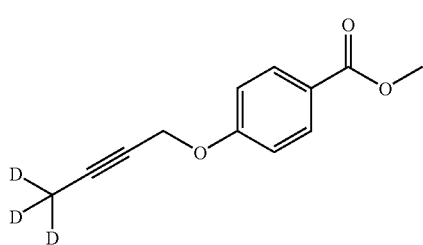
13b

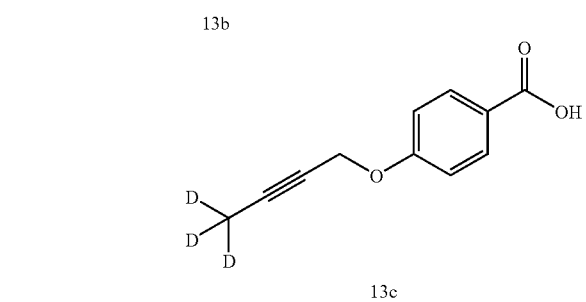
13c

Compound 13c is prepared from 13b by using procedure analogous to the synthesis of 4c in Step 4-C. Found m/z ES+=194 and ES−=192.

Step 13-C:

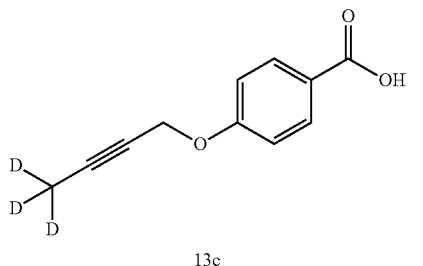
13c

+

-continued

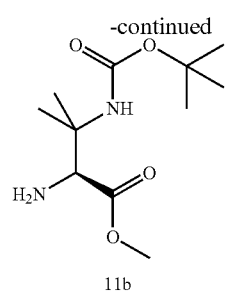
11b

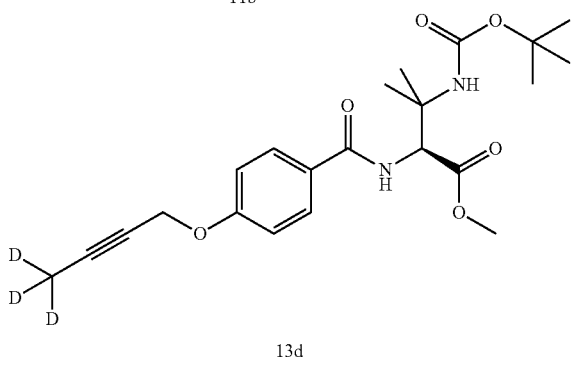
13d

Compound 13d is prepared from 13c by using procedure analogous to the synthesis of 11f in Step 11-E.

Step 13-D:

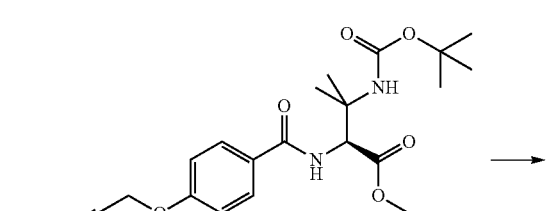
13d

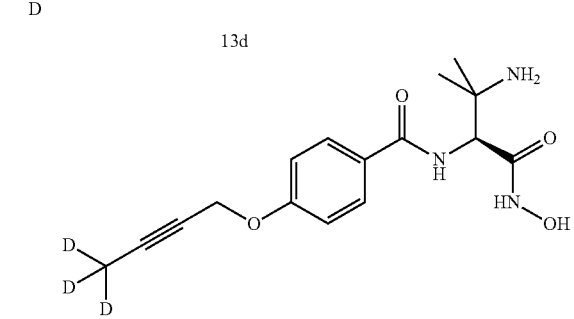
13

The TFA salt of compound 13 is prepared from 13d by using procedure analogous to the synthesis of 2 in Step 2-F. Then the MeOH solution of TFA goes though a polymer supported hydrogen carbonate cartridge (SratoSpheres™ SPE PL-HCO$_3$ NIP-Resin cartridge, with MeOH as eluent solvent) followed by removing solvents under reduced pressure to afford the neutral form of 13. The HCl salt of 13 is obtained from its neutral form by using analogous procedure to Step 2-G except using only 1.05 eq. of HCl (aq. 1N) and do freeze-dry lypholization once. LC-MS method 1, Rt=0.65 min. Found m/z ES+=323 and ES−=321. $^1$H NMR (400 MHz, DMSO-d$_6$, HCl salt) δ=11.2 (s, 1H), 9.20 (s, 1H), 8.38 (d, 1H), 8.10 (bs, 3H), 7.96 (d, 2H), 7.05 (d, 2H), 4.83 (s, 2H), 4.68 (d, 1H), 1.34 (s, 3H), 1.30 (s, 3H).

EXAMPLE 14

N-((S)-2-Amino-1-hydroxycarbamoyl-2-methyl-propyl)-4-but-1-d2-methylene-2-ynyloxy-benzamide (Compound 14)

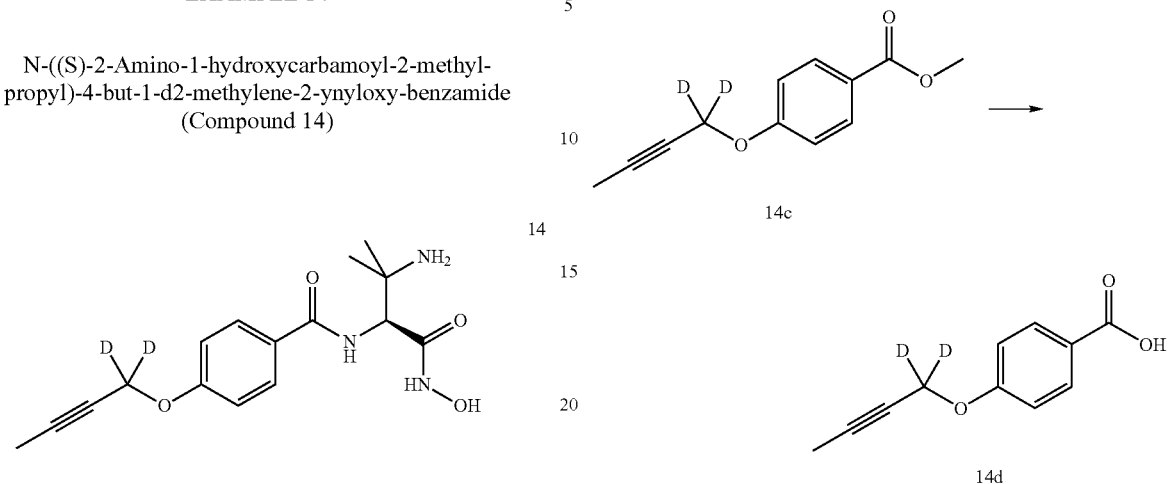

Step 14-A:

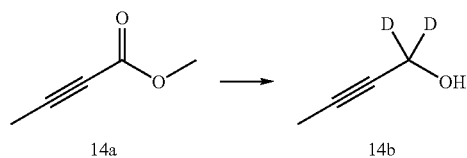

To a suspension of LiAlD4 (160 mg, 3.82 mmol) in anhydrous diethyl ether (Et$_2$O, 20 mL, pre-bubbled with N$_2$ for 10 min) is added 14a (500 mg, 5.10 mmol) at −78° C. under N$_2$ protection. Then the reaction is put in a −45° C. ACN/dry ice bath and stirred at −45° C. for 2 h after which the reaction is quenched by adding NaOH (aq. 0.3 N, 6 mL) dropwisely at −45° C. The reaction mixture is kept under N$_2$ protection during reaction and quenching. The resulted white slurry is filtered out and rinsed with Et$_2$O (40 mL). The filtrate is dried over Na$_2$SO$_4$, filtered followed by removing solvents under reduced pressure to afford 14b which is used directly in the next step without further purification.

Step 14-B:

Compound 14c is prepared from 14b by using procedure analogous to the synthesis of 4b in Step 4-B.

Step 14-C:

Compound 14d is prepared from 14c by using procedure analogous to the synthesis of 4c in Step 4-C. Found ES+=193 and ES−=191.

Step 14-D:

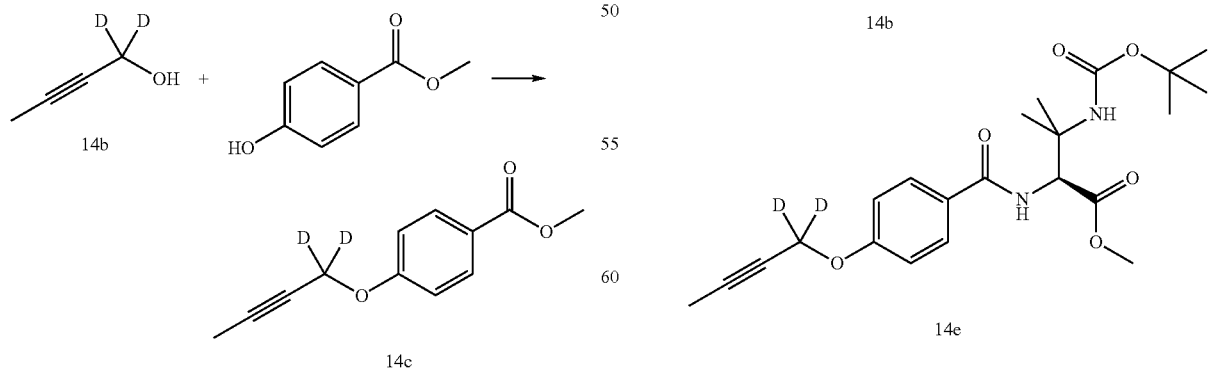

Compound 14e is prepared from 14d by using procedure analogous to the synthesis of 11f in Step 11-E. Found ES+=421 and ES−=419.

Step 14-E:

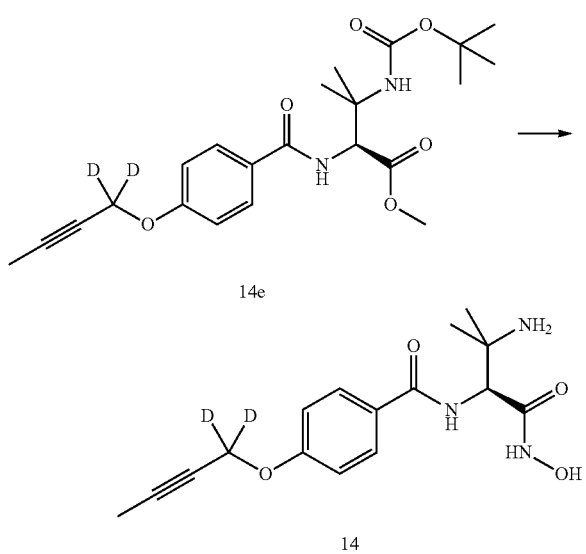

The HCl salt of 14 is prepared from 14e by using procedure analogous to the synthesis of 13 in Step 13-D. LC-MS method 1, Rt=0.64 min. Found m/z ES+=322 and ES−=320. $^1$H NMR (400 MHz, DMSO-$d_6$, HCl salt) δ=11.2 (s, 1H), 9.21 (s, 1H), 8.33 (bs, 1H), 8.01 (bs, 3H), 7.92 (d, 2H), 7.06 (d, 2H), 4.68 (d, 1H), 1.83 (s, 3H), 1.33 (s, 3H), 1.28 (s, 3H).

EXAMPLE 15

N-((S)-2-Amino-1-hydroxycarbamoyl-2-methyl-propyl)-4-((E)-7-hydroxy-hept-2-en-4-ynyloxy)-benzamide (Compound 15)

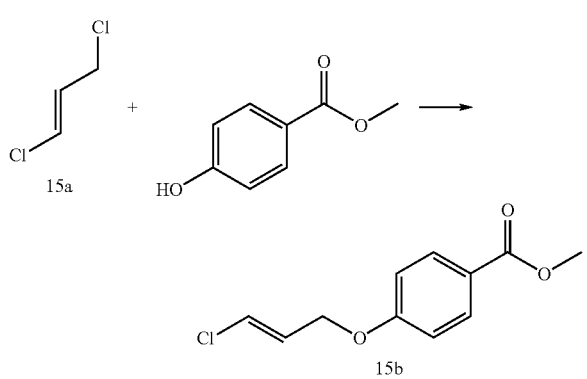

Step 15-A:

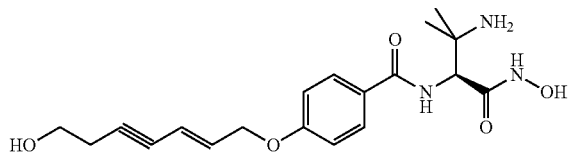

To a solution of trans-1,3-dichloropropene (2.19 g, 19.7 mmol), potassium carbonate (3.63 g, 26.3 mmol), and potassium iodide (0.109 g, 0.657 mmol) in acetonitrile (200 mL) was added methyl-4-hydroxybenzoate (2.0 g, 13.2 mmol). The reaction was stirred at 80° C. for 4 hr after which it is quenched with brine, extracted with ethyl acetate, and washed with water. Organic phase dried with anhydrous magnesium sulfate, filtered, concentrated followed by purification with silica-gel chromatography (0-50% Ethyl Acetate/Heptane) to afford 15b (2.77 g). Found m/z ES+=227.

Step 15-B:

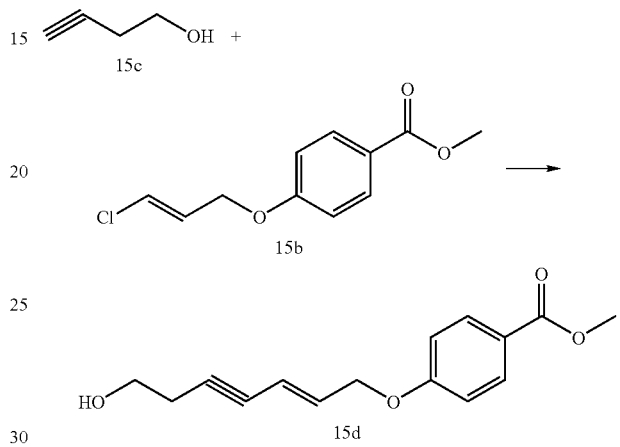

Nitrogen is bubbled through a solution of 15b (400 mg, 1.765 mmol) in piperidine (8.8 mL) before PdCl$_2$(PhCN)$_2$ catalyst (67.7 mg, 0.176 mmol), copper(I) iodide (16.8 mg, 0.088 mmol), and 3-butyn-1-ol (15c, 247 mg, 3.53 mmol) are added in that order. The reaction mixture is then stirred at 50° C. under nitrogen protection for about 10 minutes. The reaction mixture turns light green color, then light yellow, followed by a darker opaque yellow. The reaction is mixture is quenched with saturated ammonium chloride (aq.) immediately (must be quenched while it is still a dark, opaque yellow to achieve product). Then the reaction mixture is extracted with ethyl acetate, washed with sodium bicarbonate and water. Organic phase is dried with anhydrous magnesium sulfate, concentrated followed by purification with silica-gel chromatography (0-70% Ethyl Acetate/Heptane) to afford 15d (200 mg). Found m/z ES+=261.

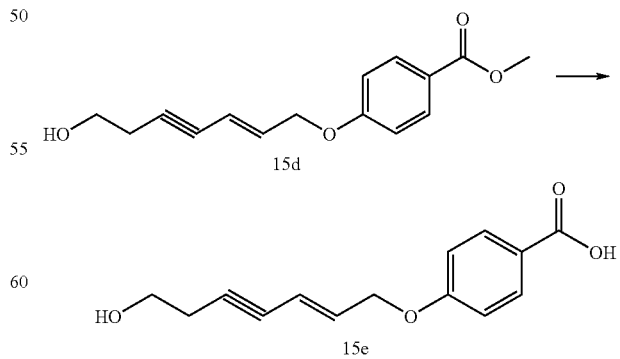

Compound 15e is prepared from 15d by using analogous procedure to the synthesis of compound 1b in Step 1-B. Found m/z ES+=247 and ES−=245.

Step 15-D:

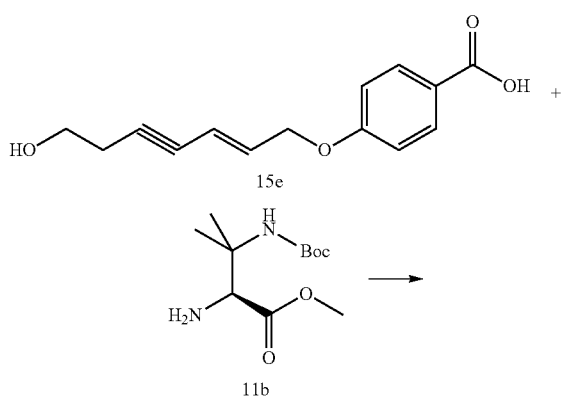

Compound 15f is prepared from 15e by using analogous procedure to the synthesis of 11f in Step 11-e. Found m/z ES+=475 and ES−=473.

Step 15-E:

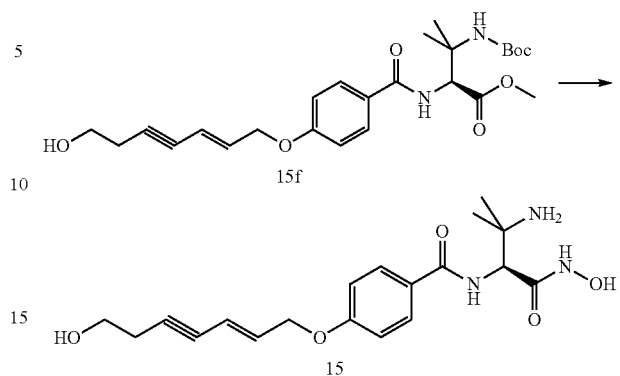

The HCl salt of compound 15 is prepared from 15f by using analogous procedure to the synthesis of compound 2 in Step 2-F and Step 2-G. LC-MS method 2, Rt=0.81 min. Found m/z ES+=376 and ES−=374. $^1$H NMR (400 MHz, DMSO-d$_6$, HCl salt) δ=11.2 (s, 1H), 9.0 (bs, 1H), 8.17 (s, 3H), 7.97 (d, 2H), 7.03 (d, 2H), 6.19 (m, 1H), 5.91 (d, 1H), 4.68 (m, 3H), 3.45 (t, 2H), 2.43 (m, 2H), 1.30 (s, 3H), 1.28 (s, 3H).

Table A provides additional compounds of the invention, e.g., Examples 16-83 (including pharmaceutically acceptable salts thereof, as well as enantiomers, stereoisomers, rotamers, tautomers, diastereomers, or racemates thereof). Compounds of Examples 16-83 are isolated in either free base or as acid addition salts.

TABLE A

| Example | Structure | Characterization |
|---|---|---|
| 16 | 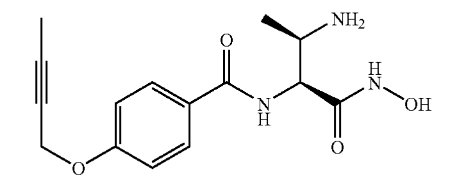 [SMILES: CC#CCOc1ccc(C(=O)N[C@H](C(=O)NO)[C@@H](C)N)cc1] | LC-MS method 4, Rt = 0.73 min.; Found m/z ES+ = 306 and ES− = 304. |
| 17 | 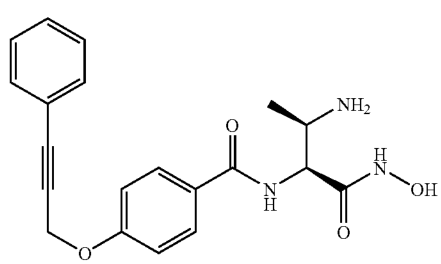 [SMILES: C[C@@H](N)[C@H](NC(=O)c1ccc(OCC#Cc2ccccc2)cc1)C(=O)NO] | LC-MS method 4, Rt = 1.1 min.; Found m/z ES+ = 368 and ES− = 366. |
| 18 | 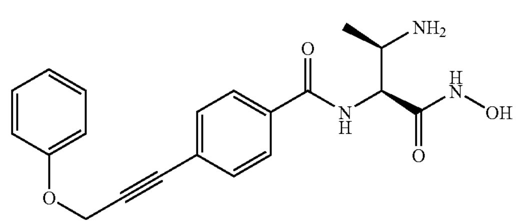 [SMILES: C[C@@H](N)[C@H](NC(=O)c1ccc(C#CCOc2ccccc2)cc1)C(=O)NO] | LC-MS method 2, Rt = 0.9 min.; Found m/z ES+ = 368 and ES− = 366. |

TABLE A-continued

| Example | Structure | Characterization |
|---------|-----------|------------------|
| 19 | 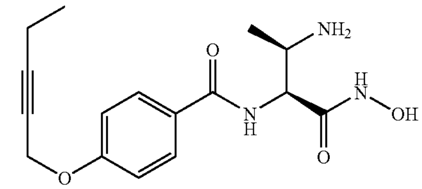 [SMILES: CCC#CCOc1ccc(C(=O)N[C@H](C(=O)NO)[C@@H](C)N)cc1] | LC-MS method 4, Rt = 1.1 min.; Found m/z ES+ = 320 and ES− = 318. |
| 20 | 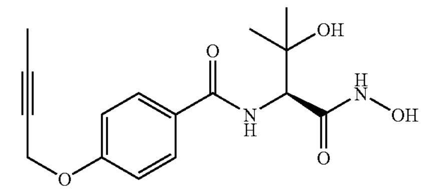 [SMILES: CC#CCOc1ccc(C(=O)N[C@H](C(=O)NO)C(C)(C)O)cc1] | LC-MS method 2, Rt = 0.95 min.; Found m/z ES+ = 321 and ES− = 319. |
| 21 | 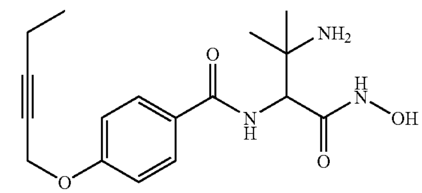 [SMILES: CCC#CCOc1ccc(C(=O)NC(C(=O)NO)C(C)(C)N)cc1] | LC-MS method 2, Rt = 0.96 min.; Found m/z ES+ = 334 and ES− = 332. |
| 22 | 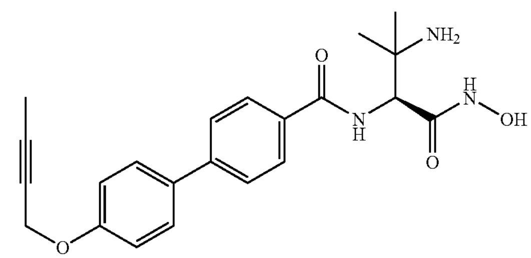 [SMILES: CC#CCOc1ccc(-c2ccc(C(=O)N[C@H](C(=O)NO)C(C)(C)N)cc2)cc1] | LC-MS method 2, Rt = 1.08 min.; Found m/z ES+ = 396 and ES− = 394. |
| 23 | 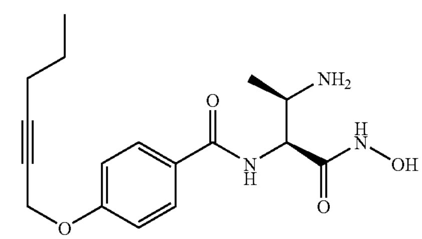 [SMILES: CCCC#CCOc1ccc(C(=O)N[C@H](C(=O)NO)[C@@H](C)N)cc1] | LC-MS method 4, Rt = 1.1 min.; Found m/z ES+ = 334 and ES− = 332. |
| 24 | 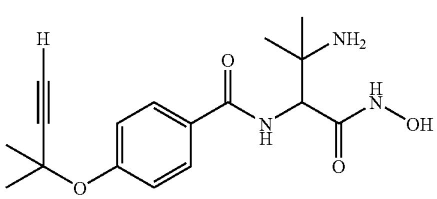 [SMILES: C#CC(C)(C)Oc1ccc(C(=O)NC(C(=O)NO)C(C)(C)N)cc1] | LC-MS method 4, Rt = 1.2 min.; Found m/z ES+ = 334 and ES− = 332. |
| 25 | 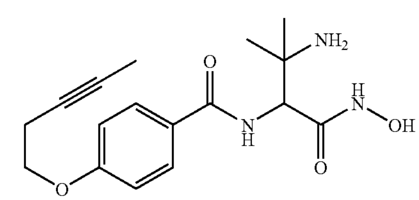 [SMILES: CC#CCCOc1ccc(C(=O)NC(C(=O)NO)C(C)(C)N)cc1] | LC-MS method 2, Rt = 0.86 min.; Found m/z ES+ = 334 and ES− = 332. |

TABLE A-continued

| Example | Structure | Characterization |
|---|---|---|
| 26 | 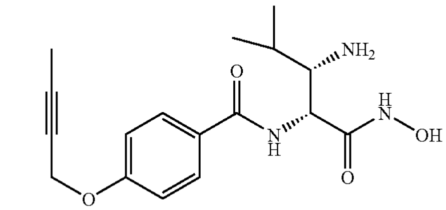 [SMILES: CC#CCOc1ccc(C(=O)N[C@@H](C(=O)NO)[C@@H](N)C(C)C)cc1] | LC-MS method 2, Rt = 0.92 min.; Found m/z ES+ = 334 and ES− = 332. |
| 27 | 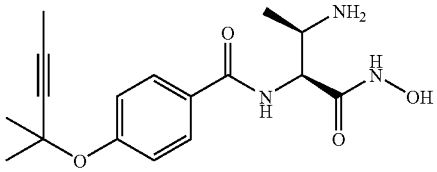 [SMILES: CC#CC(C)(C)Oc1ccc(C(=O)N[C@H](C(=O)NO)[C@@H](C)N)cc1] | LC-MS method 4, Rt = 1.0 min.; Found m/z ES+ = 334 and ES− = 332. |
| 28 | 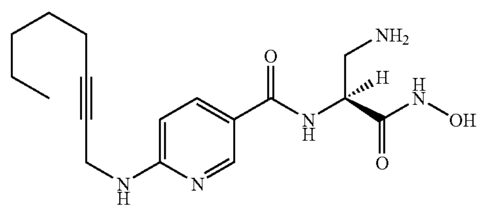 [SMILES: CCCCCC#CCNc1ccc(C(=O)N[C@@H](CN)C(=O)NO)cn1] | LC-MS method 1, Rt = 0.93 min.; Found m/z ES+ = 349 and ES− = 347. |
| 29 | 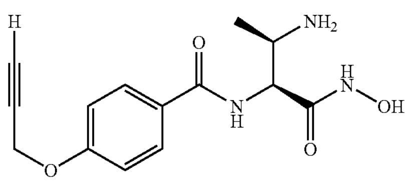 | LC-MS method 2, Rt = 0.47 min.; Found m/z ES+ = 292 and ES− = 290. |
| 30 | 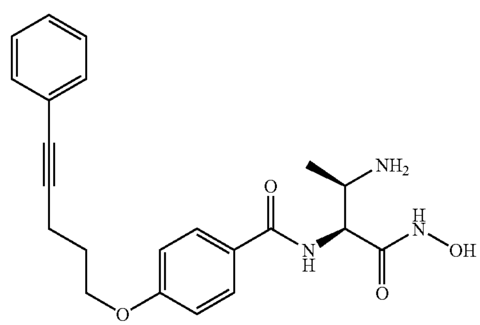 [SMILES: C[C@@H](N)[C@H](NC(=O)c1ccc(OCCCC#Cc2ccccc2)cc1)C(=O)NO] | LC-MS method 2, Rt = 1.08 min.; Found m/z ES+ = 396 and ES− = 394. |
| 31 | 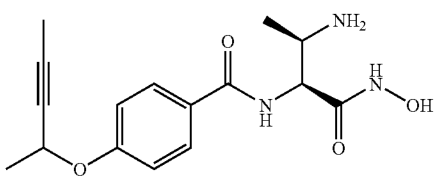 [SMILES: CC#CC(C)Oc1ccc(C(=O)N[C@H](C(=O)NO)[C@@H](C)N)cc1] | LC-MS method 4, Rt = 0.84 min.; Found m/z ES+ = 320 and ES− = 318. |
| 32 | 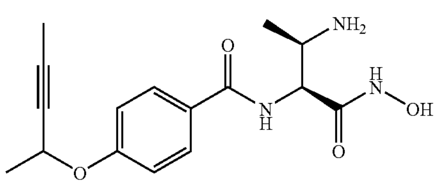 [SMILES: CC#CC(C)Oc1ccc(C(=O)N[C@H](C(=O)NO)[C@@H](C)N)cc1] | Diastereoisomer or Example 27 LC-MS method 4, Rt = 0.85 min.; Found m/z ES+ = 320 and ES− = 318. |

TABLE A-continued

| Example | Structure | Characterization |
|---|---|---|
| 33 | 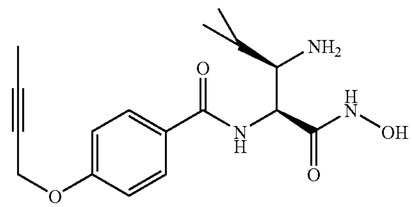 [SMILES: CC#CCOc1ccc(C(=O)N[C@H](C(=O)NO)[C@H](N)C(C)C)cc1] | LC-MS method 2, Rt = 0.88 min.;<br>Found m/z ES+ = 334 and ES− = 332. |
| 34 | 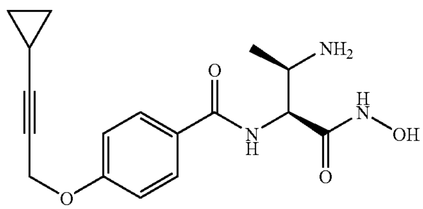 [SMILES: C[C@@H](N)[C@H](NC(=O)c1ccc(OCC#CC2CC2)cc1)C(=O)NO] | LC-MS method 4, Rt = 1.0 min.;<br>Found m/z ES+ = 332 and ES− = 330. |
| 35 | 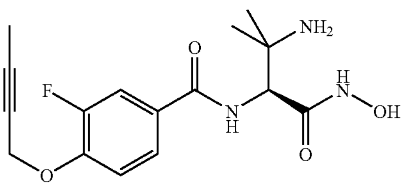 [SMILES: CC#CCOc1ccc(C(=O)N[C@H](C(=O)NO)C(C)(C)N)cc1F] | LC-MS method 1, Rt = 0.53 min.;<br>Found m/z ES+ = 338 and ES− = 336. |
| 36 | 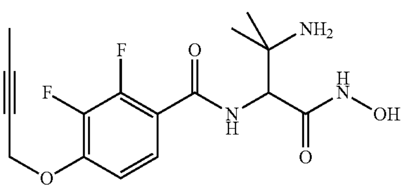 [SMILES: CC#CCOc1ccc(C(=O)NC(C(=O)NO)C(C)(C)N)c(F)c1F] | LC-MS method 1, Rt = 0.63 min.;<br>Found m/z ES+ = 356 and ES− = 354. |
| 37 | 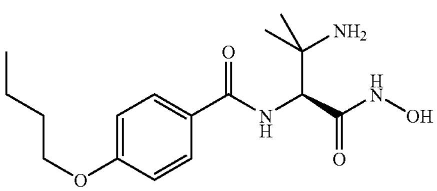 [SMILES: CCCCOc1ccc(C(=O)N[C@H](C(=O)NO)C(C)(C)N)cc1] | LC-MS method 4, Rt = 1.1 min.;<br>Found m/z ES+ = 324 and ES− = 322. |
| 38 | 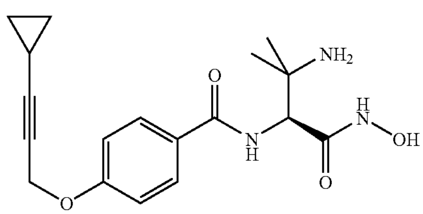 [SMILES: CC(C)(N)[C@H](NC(=O)c1ccc(OCC#CC2CC2)cc1)C(=O)NO] | LC-MS method 4, Rt = 1.1 min.;<br>Found m/z ES+ = 346 and ES− = 344. |
| 39 | 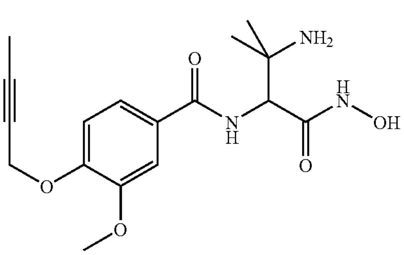 [SMILES: CC#CCOc1ccc(C(=O)NC(C(=O)NO)C(C)(C)N)cc1OC] | LC-MS method 1, Rt = 0.55 min.;<br>Found m/z ES+ = 350 and ES− = 348. |

TABLE A-continued

| Example | Structure | Characterization |
|---------|-----------|------------------|
| 40 | 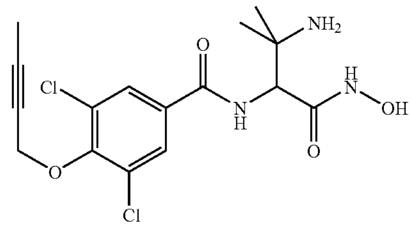 [SMILES: CC#CCOc1c(Cl)cc(C(=O)NC(C(=O)NO)C(C)(C)N)cc1Cl] | LC-MS method 1, Rt = 0.73 min.; Found m/z ES+ = 388 and ES− = 386. |
| 41 | 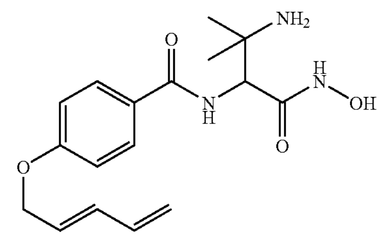 [SMILES: C=C/C=C/COc1ccc(C(=O)NC(C(=O)NO)C(C)(C)N)cc1] | LC-MS method 4, Rt = 1.13 min.; Found m/z ES+ = 334 and ES− = 332. |
| 42 | 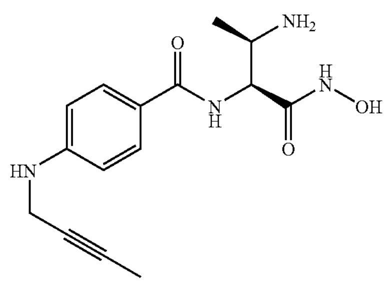 [SMILES: CC#CCNc1ccc(C(=O)N[C@H](C(=O)NO)[C@@H](C)N)cc1] | LC-MS method 4, Rt = 0.67 min.; Found m/z ES+ = 305 and ES− = 303. |
| 43 | 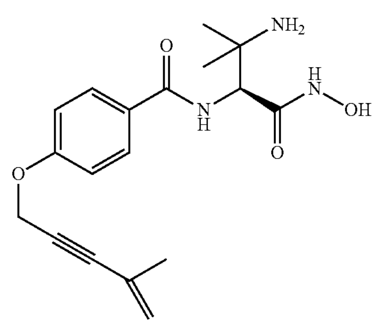 [SMILES: C=C(C)C#CCOc1ccc(C(=O)N[C@H](C(=O)NO)C(C)(C)N)cc1] | LC-MS method 1, Rt = 0.78 min.; Found m/z ES+ = 346 and ES− = 344. |
| 44 | 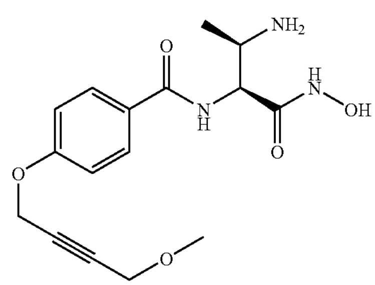 [SMILES: COCC#CCOc1ccc(C(=O)N[C@H](C(=O)NO)[C@@H](C)N)cc1] | LC-MS method 4, Rt = 0.78 min.; Found m/z ES+ = 336 and ES− = 334. |

| Example | Structure | Characterization |
|---|---|---|
| 45 | 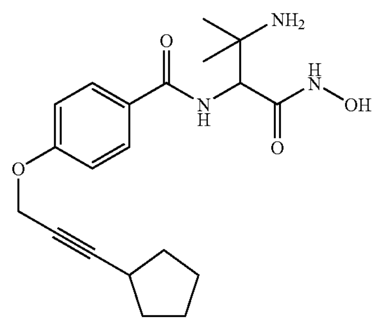 [SMILES: CC(C)(N)C(NC(=O)c1ccc(OCC#CC2CCCC2)cc1)C(=O)NO] | LC-MS method 1, Rt = 0.86 min.;<br>Found m/z ES+ = 374 and ES− = 372. |
| 46 | 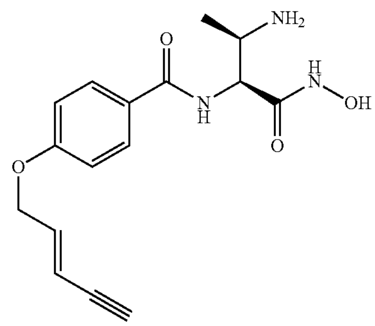 [SMILES: C#C/C=C/COc1ccc(C(=O)N[C@H](C(=O)NO)[C@@H](C)N)cc1] | LC-MS method 4, Rt = 0.93 min.;<br>Found m/z ES+ = 318 and ES− = 316. |
| 47 | 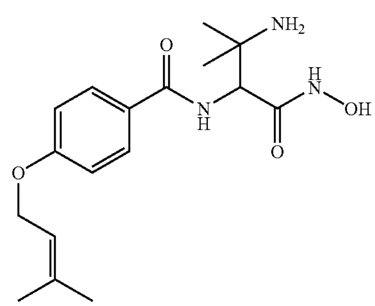 [SMILES: CC(C)=CCOc1ccc(C(=O)NC(C(=O)NO)C(C)(C)N)cc1] | LC-MS method 4, Rt = 1.16 min.;<br>Found m/z ES+ = 336 and ES− = 334. |
| 48 | 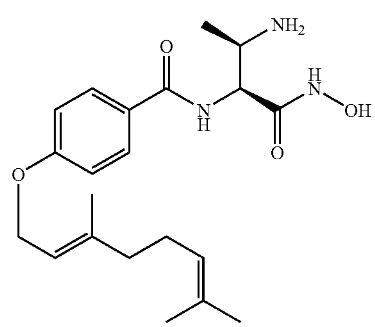 [SMILES: CC(C)=CCC/C(C)=C/COc1ccc(C(=O)N[C@H](C(=O)NO)[C@@H](C)N)cc1] | LC-MS method 4, Rt = 1.6 min.;<br>Found m/z ES+ = 390 and ES− = 388. |
| 49 | 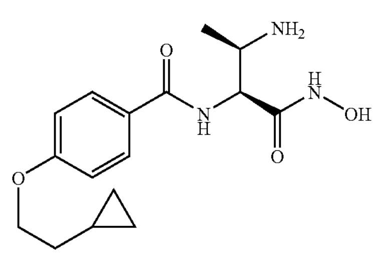 [SMILES: C[C@@H](N)[C@H](NC(=O)c1ccc(OCCC2CC2)cc1)C(=O)NO] | LC-MS method 4, Rt = 1.13 min.;<br>Found m/z ES+ = 322 and ES− = 320. |

TABLE A-continued

| Example | Structure | Characterization |
|---|---|---|
| 50 | 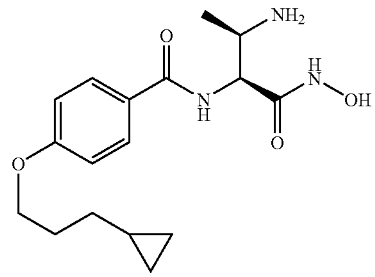 [SMILES: C[C@@H](N)[C@H](NC(=O)c1ccc(OCCCC2CC2)cc1)C(=O)NO] | LC-MS method 4, Rt = 1.27 min.; Found m/z ES+ = 336 and ES− = 334. |
| 51 | 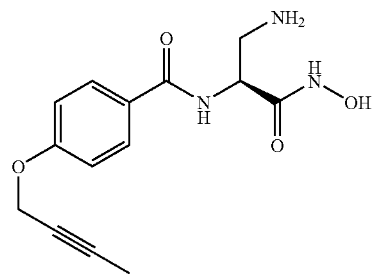 [SMILES: CC#CCOc1ccc(C(=O)N[C@@H](CN)C(=O)NO)cc1] | LC-MS method 1, Rt = 0.56 min.; Found m/z ES+ = 292 and ES− = 290. |
| 52 | 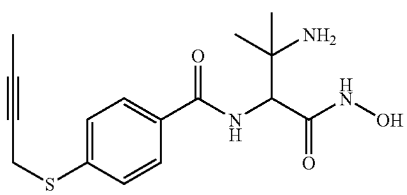 [SMILES: CC#CCSc1ccc(C(=O)NC(C(=O)NO)C(C)(C)N)cc1] | LC-MS method 4, Rt = 1.05 min.; Found m/z ES+ = 336 and ES− = 334. |
| 53 | 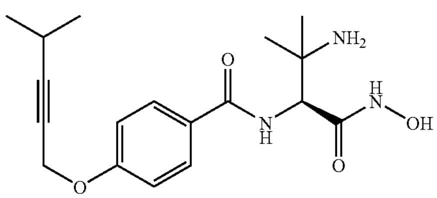 [SMILES: CC(C)C#CCOc1ccc(C(=O)N[C@H](C(=O)NO)C(C)(C)N)cc1] | LC-MS method 1, Rt = 0.77 min.; Found m/z ES+ = 348 and ES− = 346. |
| 54 | 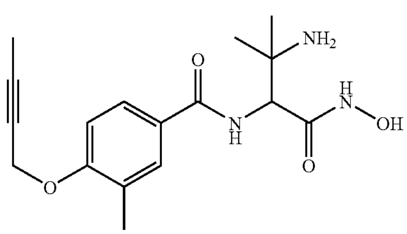 [SMILES: CC#CCOc1ccc(C(=O)NC(C(=O)NO)C(C)(C)N)cc1C] | LC-MS method 2, Rt = 0.80 min.; Found m/z ES+ = 334 and ES− = 332. |
| 55 | 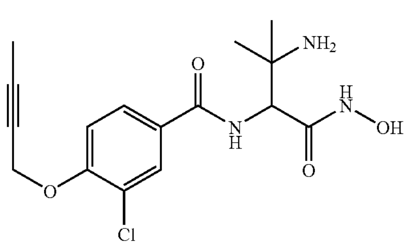 [SMILES: CC#CCOc1ccc(C(=O)NC(C(=O)NO)C(C)(C)N)cc1Cl] | LC-MS method 2, Rt = 0.81 min.; Found m/z ES+ = 354 and ES− = 352. |

TABLE A-continued

| Example | Structure | Characterization |
|---|---|---|
| 56 | 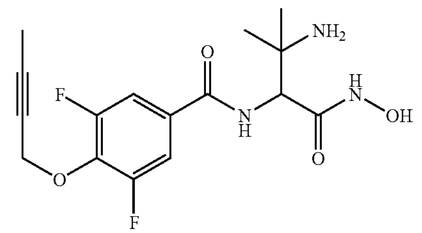 [SMILES: CC#CCOc1c(F)cc(C(=O)NC(C(=O)NO)C(C)(C)N)cc1F] | LC-MS method 1, Rt = 0.69 min.; Found m/z ES+ = 356 and ES− = 354. |
| 57 | 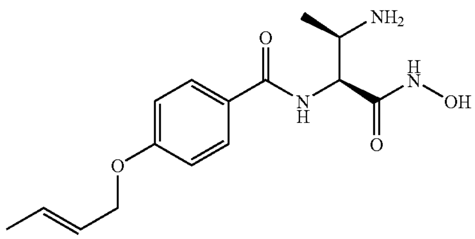 [SMILES: C/C=C/COc1ccc(C(=O)N[C@H](C(=O)NO)[C@@H](C)N)cc1] | LC-MS method 4, Rt = 1.03 min.; Found m/z ES+ = 308 and ES− = 306. |
| 58 | 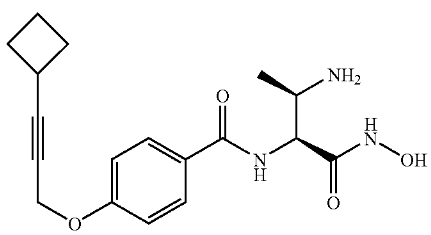 [SMILES: C[C@@H](N)[C@H](NC(=O)c1ccc(OCC#CC2CCC2)cc1)C(=O)NO] | LC-MS method 4, Rt = 1.22 min.; Found m/z ES+ = 346 and ES− = 344. |
| 59 | 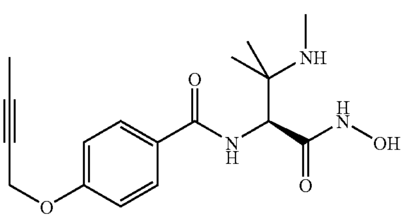 [SMILES: CC#CCOc1ccc(C(=O)N[C@H](C(=O)NO)C(C)(C)NC)cc1] | LC-MS method 1, Rt = 0.61 min.; Found m/z ES+ = 334 and ES− = 332. |
| 60 | 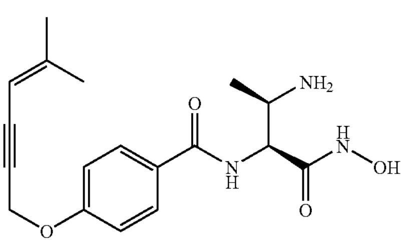 [SMILES: CC(C)=CC#CCOc1ccc(C(=O)N[C@H](C(=O)NO)[C@@H](C)N)cc1] | LC-MS method 1, Rt = 0.8 min.; Found m/z ES+ = 346 and ES− = 344. |
| 61 | 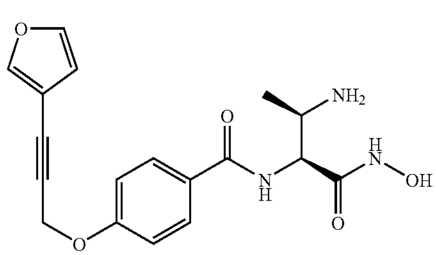 [SMILES: C[C@@H](N)[C@H](NC(=O)c1ccc(OCC#Cc2ccoc2)cc1)C(=O)NO] | LC-MS method 1, Rt = 0.76 min.; Found m/z ES+ = 358 and ES− = 356. |

TABLE A-continued

| Example | Structure | Characterization |
|---|---|---|
| 62 | 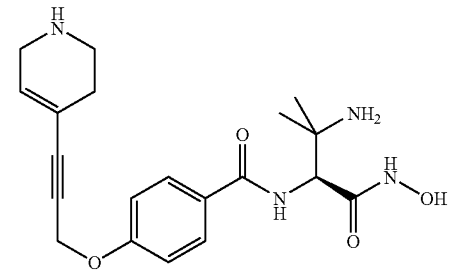 [SMILES: CC(C)(N)[C@H](NC(=O)c1ccc(OCC#CC2=CCNCC2)cc1)C(=O)NO] | LC-MS method 5, Rt = 0.65 min.; Found m/z ES+ = 387 and ES− = 385. |
| 63 | 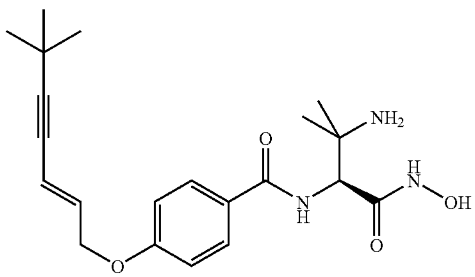 [SMILES: CC(C)(C)C#C/C=C/COc1ccc(C(=O)N[C@H](C(=O)NO)C(C)(C)N)cc1] | LC-MS method 3, Rt = 0.9 min.; Found m/z ES+ = 388 and ES− = 386. |
| 64 | 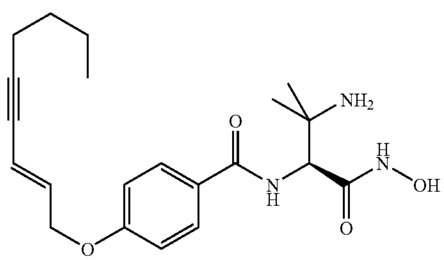 [SMILES: CCCCC#C/C=C/COc1ccc(C(=O)N[C@H](C(=O)NO)C(C)(C)N)cc1] | LC-MS method 3, Rt = 0.66 min.; Found m/z ES+ = 388 and ES− = 386. |
| 65 | 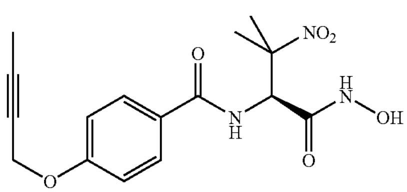 | LC-MS method 4, Rt = 0.85 min.; Found m/z ES+ = 317 and ES− = 315. |
| 66 | 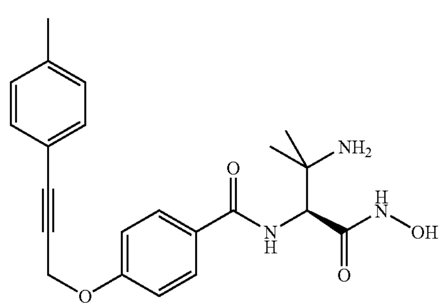 [SMILES: Cc1ccc(C#CCOc2ccc(C(=O)N[C@H](C(=O)NO)C(C)(C)N)cc2)cc1] | LC-MS method 4, Rt = 1.6 min.; Found m/z ES+ = 395 and ES− = 393. |

TABLE A-continued

| Example | Structure | Characterization |
|---|---|---|
| 67 | 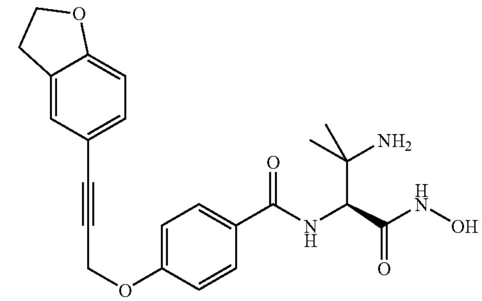 [SMILES: CC(C)(N)[C@H](NC(=O)c1ccc(OCC#Cc2ccc3c(c2)CCO3)cc1)C(=O)NO] | LC-MS method 3, Rt = 0.4 min.; Found m/z ES+ = 424 and ES− = 422. |
| 68 | 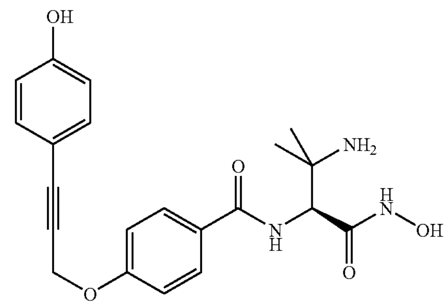 [SMILES: CC(C)(N)[C@H](NC(=O)c1ccc(OCC#Cc2ccc(O)cc2)cc1)C(=O)NO] | LC-MS method 4, Rt = 1.1 min.; Found m/z ES+ = 398 and ES− = 396. |
| 69 | 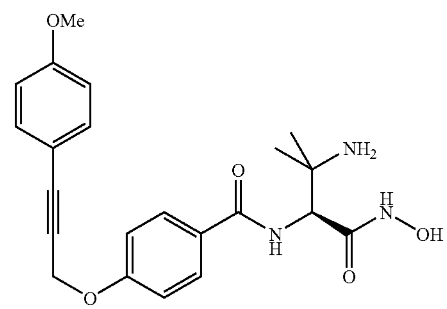 [SMILES: COc1ccc(C#CCOc2ccc(C(=O)N[C@H](C(=O)NO)C(C)(C)N)cc2)cc1] | LC-MS method 4, Rt = 1.28 min.; Found m/z ES+ = 412 and ES− = 410. |
| 70 | 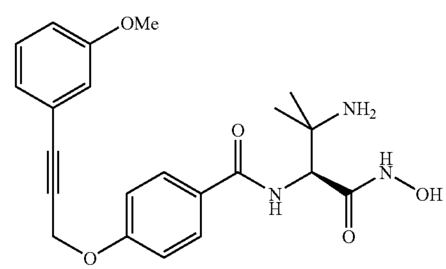 [SMILES: COc1cccc(C#CCOc2ccc(C(=O)N[C@H](C(=O)NO)C(C)(C)N)cc2)c1] | LC-MS method 4, Rt = 1.38 min.; Found m/z ES+ = 412 and ES− = 410. |
| 71 | 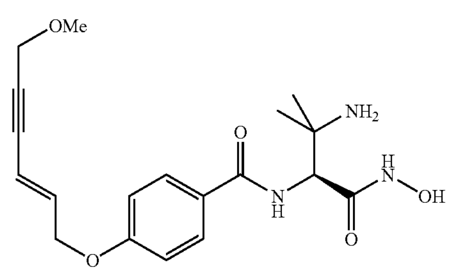 [SMILES: COCC#C/C=C/COc1ccc(C(=O)N[C@H](C(=O)NO)C(C)(C)N)cc1] | LC-MS method 4, Rt = 1.08 min.; Found m/z ES+ = 376 and ES− = 374. |

TABLE A-continued

| Example | Structure | Characterization |
|---|---|---|
| 72 | 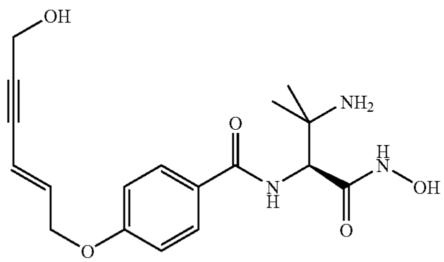 [SMILES: CC(C)(N)[C@H](NC(=O)c1ccc(OC/C=C/C#CCO)cc1)C(=O)NO] | LC-MS method 4, Rt = 0.95 min.; Found m/z ES+ = 362 and ES− = 360. |
| 73 | 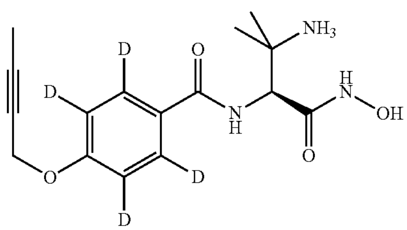 [SMILES: [2H]c1c([2H])c(C(=O)N[C@H](C(=O)NO)C(C)(C)N)c([2H])c([2H])c1OCC#CC] | LC-MS method 1, Rt = 0.68 min.; Found m/z ES+ = 324 and ES− = 322. |
| 74 | 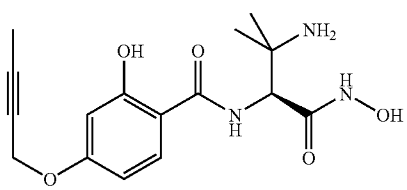 [SMILES: CC#CCOc1ccc(C(=O)N[C@H](C(=O)NO)C(C)(C)N)c(O)c1] | LC-MS method 1, Rt = 0.61 min.; Found m/z ES+ = 336 and ES− = 334. |
| 75 | 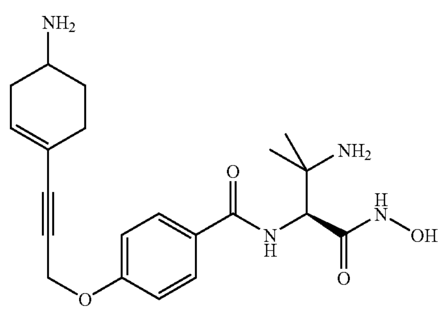 [SMILES: CC(C)(N)[C@H](NC(=O)c1ccc(OCC#CC2=CCC(N)CC2)cc1)C(=O)NO] | LC-MS method 1, Rt = 0.53 min.; Found m/z ES+ = 401 and ES− = 399. |
| 76 | 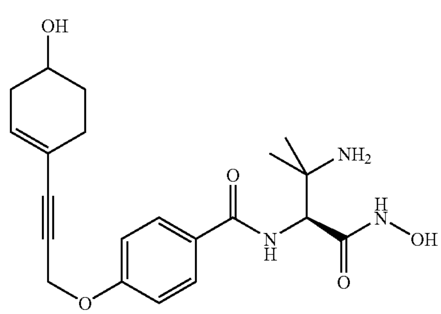 [SMILES: CC(C)(N)[C@H](NC(=O)c1ccc(OCC#CC2=CCC(O)CC2)cc1)C(=O)NO] | LC-MS method 2, Rt = 1.03 min.; Found m/z ES+ = 402 and ES− = 400. |
| 77 | 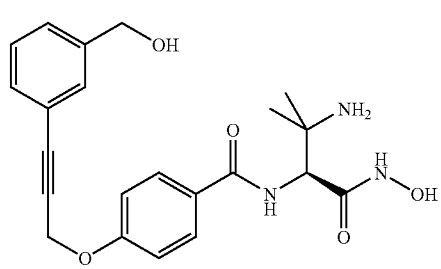 [SMILES: CC(C)(N)[C@H](NC(=O)c1ccc(OCC#Cc2cccc(CO)c2)cc1)C(=O)NO] | LC-MS method 2, Rt = 1.17 min.; Found m/z ES+ = 412 and ES− = 410. |

TABLE A-continued

| Example | Structure | Characterization |
|---|---|---|
| 78 | 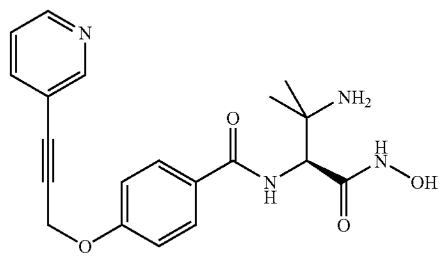 [SMILES: CC(C)(N)[C@H](NC(=O)c1ccc(OCC#Cc2cccnc2)cc1)C(=O)NO] | LC-MS method 4, Rt = 0.96 min.; Found m/z ES+ = 383 and ES− = 381. |
| 79 | 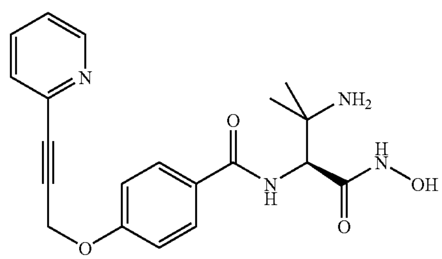 [SMILES: CC(C)(N)[C@H](NC(=O)c1ccc(OCC#Cc2ccccn2)cc1)C(=O)NO] | LC-MS method 4, Rt = 0.95 min.; Found m/z ES+ = 383 and ES− = 381. |
| 80 | 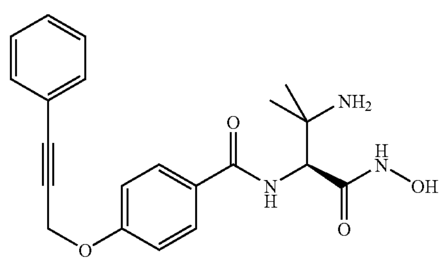 [SMILES: CC(C)(N)[C@H](NC(=O)c1ccc(OCC#Cc2ccccc2)cc1)C(=O)NO] | LC-MS method 4, Rt = 1.37 min.; Found m/z ES+ = 382 and ES− = 380. |
| 81 | 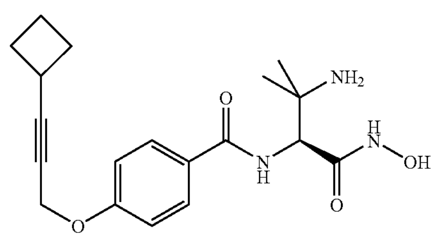 [SMILES: CC(C)(N)[C@H](NC(=O)c1ccc(OCC#CC2CCC2)cc1)C(=O)NO] | LC-MS method 4, Rt = 1.3 min.; Found m/z ES+ = 360 and ES− = 358. |
| 82 | 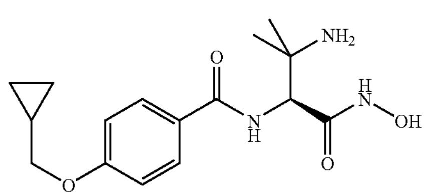 [SMILES: CC(C)(N)[C@H](NC(=O)c1ccc(OCC2CC2)cc1)C(=O)NO] | LC-MS method 2, Rt = 0.61 min.; Found m/z ES+ = 322 and ES− = 320. |
| 83 | 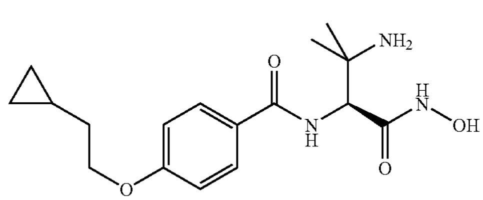 [SMILES: CC(C)(N)[C@H](NC(=O)c1ccc(OCCC2CC2)cc1)C(=O)NO] | LC-MS method 2, Rt = 0.95 min.; Found m/z ES+ = 336 and ES− = 334. |

Table B provides additional compounds of the invention which are contemplated for use in the methods and formulations of the invention.

TABLE B

B-1
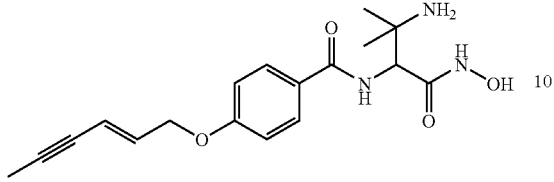

B-2
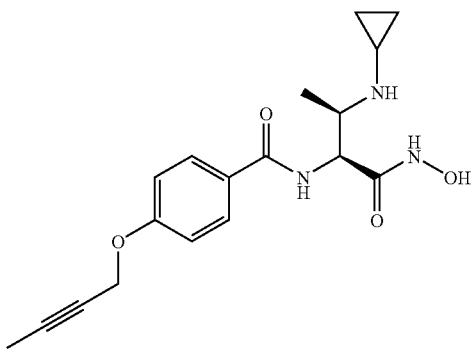 [SMILES: CC#CCOc1ccc(C(=O)N[C@H](C(=O)NO)[C@@H](C)NC2CC2)cc1]

B-3
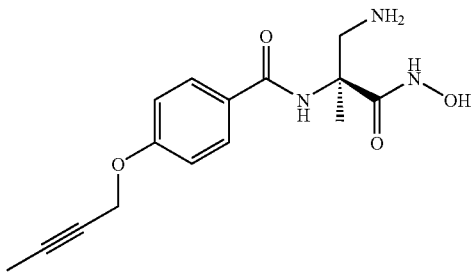 [SMILES: CC#CCOc1ccc(C(=O)N[C@@](C)(CN)C(=O)NO)cc1]

B-4
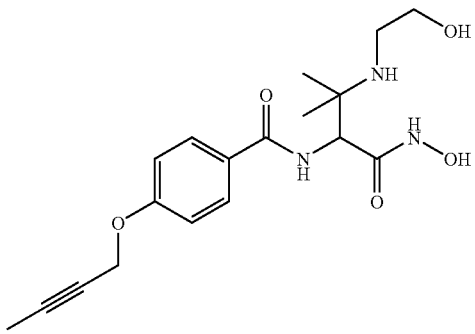 [SMILES: CC#CCOc1ccc(C(=O)NC(C(=O)NO)C(C)(C)NCCO)cc1]

B-5
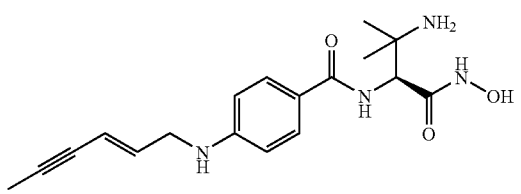 [SMILES: CC#C/C=C/CNc1ccc(C(=O)N[C@H](C(=O)NO)C(C)(C)N)cc1]

TABLE B-continued

B-6
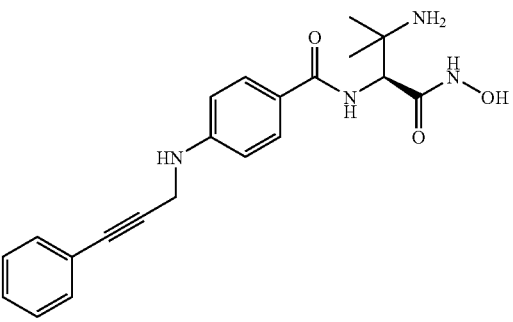 [SMILES: CC(C)(N)[C@H](NC(=O)c1ccc(NCC#Cc2ccccc2)cc1)C(=O)NO]

EXAMPLE 54

*P. aeruginosa* LpxC Inhibition Assay

The *P. aeruginosa* LpxC protein is produced according to the general method of Hyland et al (Journal of Bacteriology 1997 179, 2029-2037: Cloning, expression and purification of UDP-3-O-acyl-GlcNAc deacetylase from *Pseudomonas aeruginosa*: a metalloamidase of the lipid A biosynthesis pathway). The LC-MS/MS method for quantitation of LpxC product was developed using an Agilent 1200 Capillary HPLC system coupled to an Applied Biosystems MDS Sciex 4000QTRAP mass spectrometer. Both instruments are controlled using the Applied Biosystems MDS Sciex Analyst software. LpxC reaction product (UDP-3-O—(R-3-hydroxyacyl)-glucosamine) was produced by hydrolysis of LpxC substrate catalyzed by P. a. LpxC and purified using reversed phase chromatography on a Phenomenex Luna C18 (2) 4.6×50 mm column. An LpxC product calibration curve was generated to evaluate the sensitivity and dynamic range of the LC-MS/MS method. Briefly, compounds are pre-incubated with 1 nM *P. aeruginosa* LpxC for 30 min. at room temperature. Reactions are initiated by the addition of 2 μM UDP-3-O—(R-3-hydroxydecanoyl)-GlcNAc. Reactions are conducted in a 96-well plate with a total volume of 100 μL in each well containing 50 mM Sodium phosphate pH 7.5, 0.005% Trition X-100 for 20 min at room temperature. After quenching with 1.8% HOAc (10 μL of a 20% HOAc added to each well), reaction mixtures are analyzed using the LC-MS/MS method and peak areas are transformed into product concentration using a LpxC product calibration curve. Total activity (0% inhibition control) is obtained from reactions with no inhibitors and 100% inhibition control is the background using quenched samples before reaction starts. For $IC_{50}$ determinations, peak areas are converted to percent inhibition in Microsoft Excel. Percent inhibition values are plotted vs. log compound concentration using XLfit. Data is fit to the four-parameter logistic equation using the non-linear regression algorithm in XLfit to return the $IC_{50}$ and hill slope values. The LpxC inhibitory activity for the compounds of Examples 1-84 is reported in Table C

TABLE C

| Example | $IC_{50}$ (nM) |
|---|---|
| 1 | 13.7 |
| 2 | 1.5 |
| 3 | 65 |
| 4 | 23 |
| 5 | 123.8 |
| 6 | 13.5 |
| 7 | 380.3 |

TABLE C-continued

| Example | IC$_{50}$ (nM) |
|---|---|
| 8 | 183.5 |
| 9 | 74.5 |
| 10 | 2700 |
| 11 | 1 |
| 12 | 2 |
| 13 | 1 |
| 14 | 1 |
| 15 | 2 |
| 16 | 8.7 |
| 17 | 1 |
| 18 | 7.6 |
| 19 | 7.6 |
| 20 | 6.5 |
| 21 | 1 |
| 22 | 0.7 |
| 23 | 1.5 |
| 24 | 1.4 |
| 25 | 35.1 |
| 26 | 70 |
| 27 | 73.3 |
| 28 | 55.7 |
| 29 | 38.9 |
| 30 | 35.6 |
| 31 | 141 |
| 32 | 231 |
| 33 | 268 |
| 34 | 6 |
| 35 | 2.6 |
| 36 | 15.9 |
| 37 | 4 |
| 38 | 0.4 |
| 39 | 150.6 |
| 40 | 34.6 |
| 41 | 2.1 |
| 42 | 27.3 |
| 43 | 1 |
| 44 | 56.9 |
| 45 | 2.2 |
| 46 | 5.5 |
| 47 | 3.7 |
| 48 | 10.2 |
| 49 | 24.6 |
| 50 | 13.1 |
| 51 | 128 |
| 52 | 4.4 |
| 53 | 5.5 |
| 54 | 16.7 |
| 55 | 9.9 |
| 56 | 4.1 |
| 57 | 30 |
| 58 | 6.5 |
| 59 | 3.2 |
| 60 | 8 |
| 61 | 3 |
| 62 | 14 |
| 63 | 0.05 |
| 64 | 0.2 |
| 65 | 9 |
| 66 | 1236 |
| 67 | 540 |
| 68 | 1900 |
| 69 | 413 |
| 70 | 2 |
| 71 | 1 |
| 72 | 1 |
| 73 | 1 |
| 74 | 3 |
| 75 | 6 |
| 76 | 0.03 |
| 77 | 0.2 |
| 78 | 10 |
| 79 | 1 |
| 80 | 1 |
| 81 | 0.03 |
| 82 | 18 |
| 83 | 8 |

EXAMPLE 84

Bacterial Screens and Cultures

Bacterial isolates are cultivated from −70° C. frozen stocks by two consecutive overnight passages at 35° C. in ambient air on 5% blood agar (Remel, Lenexa, Kans.). Clinical isolates tested are from a collection composed of isolates collected during clinical trials and recent clinical isolates obtained from various geographically diverse hospitals in the US and other countries. Quality control and primary panel strains are from the American Type Culture Collection (ATCC; Rockville, Md.), with the exception of *P. aeruginosa* K119, a strain with a deletion of the mexABoprM genes (PAO1 background) that is received from Dr. K. Poole. This strain does not express the principal multidrug efflux pump and is hypersusceptible to many antibacterials. Strain Z61 (ATCC 35151) is also hypersusceptible to antibacterials. It is thought that the hypersusceptibility of this strain is the result of increased permeability of its outer membrane (Angus B L et al, Antimicrobial Agents and Chemotherapy 1982 21, 299-309: Outer membrane permeability in *Pseudomonas aeruginosa*: Comparison of a wild-type with an antibacterial-super-susceptible mutant).

EXAMPLE 85

Susceptibility Testing

Minimum Inhibitory Concentrations (MICs) are determined by the broth microdilution method in accordance with the CLSI (Clinical and Laboratories Institute; formerly National Committee for Clinical Laboratory Standards (NC-CLS)) guidelines. In brief, bacterial suspensions were adjusted in sterile saline to a 0.5 McFarland turbidity standard, and then diluted 10-fold in cation adjusted MEM (Mueller-Hinton Broth; Remel) to yield a final inoculum of approximately $5 \times 10^5$ colony-forming units (CFU)/mL. Two-fold serial dilutions of drugs are made in sterile dimethyl sulfoxide at 100-fold the highest final assay concentration. One μl of the drug dilution series is added to microtiter wells containing 100 μl of MHB broth, after which 1.5 μl of bacterial suspension was inoculated into the wells. All inoculated microdilution trays were incubated in ambient air at 35° C. for 18-24 hours. Following incubation, the lowest concentration of the drug that prevented visible growth is recorded as the MIC. Performance of the assay is monitored by the use of laboratory quality-control strains against tobramycin, that has a defined MIC spectrum, in accordance with CLSI guidelines. Compounds of Examples 1-6, 8-19, 21, 23-26 and 28-53 exhibit an MIC of 64 μg/mL against at least one *P. aerugnosa* strain selected from PAO1 and ATCC27853.

EXAMPLE 86

Efficacy in Mouse Model of Systemic *Pseudomonas aeruginosa* Infection

Female CD1 mice (20-25 g) are injected intraperitoneally with 0.3 ml of a bacterial suspension containing approximately 100 times the dose that would kill 50% of animals (LD$_{50}$) of *P. aeruginosa* strain NB52019. At one and five hours post infection, the test compound is injected intravenously in doses ranging from <0.1 mg/kg to 100 mg/kg, typically 5-6 mice per group. Mice are observed for 5 clays, and the dose of compound resulting in survival of 50% of mice ($ED_{50}$) is calculated by Probit analysis.

EXAMPLE 87

Efficacy in a Mouse Pulmonary Infection Model Caused by *Pseudomonas aeruginosa*

Female BALB/c mice (17-20 g) are rendered neutropenic by 2 injections of cyclophosphamide (150 mg/kg at day—4, i.p. and 100 mg/kg at day—1). Mice are then infected intranasally while under anesthesia with approximately $5 \times 10^5$ CFU/mouse of a strain of *P. aeruginosa*. Mice are then treated at various intervals over a period of 24 hours with test compounds or comparator drugs via i.v, p.o or s.c routes of administration in doses ranging from >0.1 mg/kg to 200 mg/kg, with typically 5 mice used per group. Mice are sacrificed at 24 hours post-infection and the lungs removed for bacterial enumeration. The dose required for a 2 or 3-log reduction compared to vehicle treated animals is then calculated.

EXAMPLE 88

Drug Combination (Synergy) Studies

I. Principle

Checkerboard experiments can be performed to assess potential interactions between primary drug of interest (#1) and other related antibacterials (#2). *P. aeruginosa* ATCC 27853, *S. aureus* ATCC 29213 and other organisms can be used as challenge strains as well as selected clinical isolates. Broth microdilution format can be used to assess the activity of drug #1 and test compound alone and in combination. Two-fold dilutions of the two compounds to be tested (each bracketing the expected MIC value) are used. The fractional inhibitory concentration (FIC) is calculated as the MIC of compound #1 in combination with a second compound, divided by the MEC of compound #1 alone. A summation FIC (ΣFIC) is computed for each drug combination as the sum of the individual FICs of compound #1 and #2. Synergy is defined as an ΣFIC≧0.5, indifference as an ΣFIC between 1 and 2, and antagonism as ΣFIC>2. The lowest ΣFIC is used for the final interpretation of drug combination studies.

Interpretation of Summation (ΣFIC)
a) Synergism, x≦0.5
b) Additive, x>0.5-1
b) Indifference, x>1-2
c) Antagonism, x>2

Those skilled in the art will recognize, or be able to ascertain using no more than routine experimentation, many equivalents to the specific embodiments and methods described herein. Such equivalents are intended to be encompassed by the scope of the following claims.

What is claimed is:
1. A compound represented by Formula II:

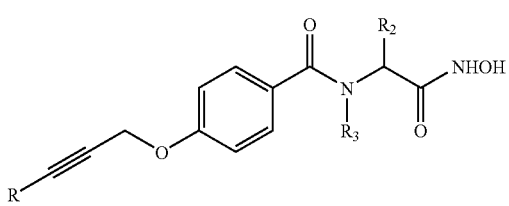

II and salts, and isomers thereof, wherein
R is $C_1$-$C_6$alkyl or $C_3$-$C_6$cycloalkyl;
$R_2$ is $CR_{2a}R_{2b}NR_6R_7$;
$R_{2a}$ is hydrogen, $C_1$-$C_4$alkyl, $C_1$-$C_4$haloalkyl, or $C_3$-$C_6$cycloalkyl;
$R_{2b}$ is hydrogen or $C_1$-$C_4$alkyl;
$R_3$ is selected from hydrogen or $C_1$-$C_4$alkyl; and
$R_6$ and $R_7$ are independently selected from the group consisting of hydrogen, $C_1$-$C_4$alkyl, and $C_1$-$C_4$alkanoyl.

2. The compound according to claim 1, represented by

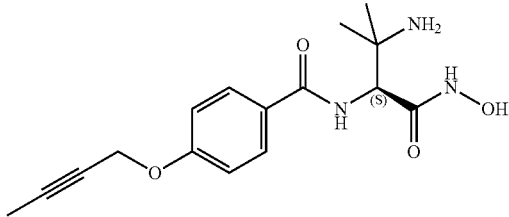

or a pharmaceutically acceptable salt thereof.

3. A compound selected from the group consisting of:
N-(1-(1-aminocyclopropyl)-2-(hydroxyamino)-2-oxoethyl)-4-(but-2-ynyloxy)benzamide;
N-(3-amino-1-(hydroxyamino)-3-methyl-1-oxobutan-2-yl)-4-(but-2-ynyloxy)benzamide;
N-(3-amino-1-(hydroxyamino)-3-methyl-1-oxobutan-2-yl)-4-(4,4-dimethylpent-2-ynyloxy)benzamide;
N-((1R,2S)-1-amino-1-cyclopropyl-3-(hydroxyamino)-3-oxopropan-2-yl)-4-(but-2-ynyloxy)benzamide;
N-((2S,3R)-3-amino-4,4,4-trifluoro-1-(hydroxyamino)-1-oxobutan-2-yl)-4-(but-2-ynyloxy)benzamide;
N-((2S,3R)-3-amino-1-(hydroxyamino)-1-oxobutan-2-yl)-4-(but-2-ynyloxy)cyclohexanecarboxamide;
N-(3-amino-1-(hydroxyamino)-3-methyl-1-oxobutan-2-yl)-4-(4-hydroxy-4-methylpent-2-ynyloxy)benzamide;
N-((1S,2R)-2-Amino-1-hydroxycarbamoyl-propyl)-4-but-2-ynyloxy-2-fluoro-benzamide; and
racemates, diasteriomers, and enantiomers thereof; and salts thereof.

4. A method of inhibiting a deacetylase enzyme in a gram-negative bacterium, the method comprising the step of contacting the gram-negative bacteria with a compound of claim 1.

5. A method for treating a subject with a gram-negative bacterial infection, the method comprising the step of administering to the subject in need thereof an antibacterially effective amount of a compound of claim 1 with a pharmaceutically acceptable carrier.

6. The method of claim 5, wherein the gram negative bacterial infection is an infection comprising at least one bacterium selected from the group consisting of *Pseudomonas, Stenotrophomonas maltophila, Burkholderia, Alcaligenes xylosoxidans, Acinetobacter, Enterobacteriaceae, Haemophilus, Moraxella, Bacteroids, Fransicella, Shigella, Proteus, Vibrio, Salmonella, Bordetella, Helicobactor, Legionella, Citrobactor, Serratia, Campylobactor, Yersinia* and *Neisseria*.

7. The method of claim 6, wherein the bacterium is a *Enterobacteriaceae* which is selected from the group consisting of *Serratia, Proteus, Klebsiella, Enterobacter, Citrobacter, Salmonella, Providencia, Morganella, Cedecea, Yersinia*, and *Edwardsiella* species and *Escherichia coli*.

8. The method of claim 5, wherein the subject is administered an antibacterially effective amount of a compound of claim 1 in combination with a second therapeutic agent.

9. The method of claim 8, wherein the second therapeutic agent is an efflux pump inhibitor.

10. The method of claim 8, wherein the second therapeutic agent is selected from the group consisting of Ampicillin, Piperacillin, Penicillin G, Ticarcillin, Imipenem, Meropenem, Azithromycin, erythromycin, Aztreonam, Cefepime, Cefotaxime, Ceftriaxone, Cefatazidime, Ciprofloxacin, Levofloxacin, Clindamycin, Doxycycline, Gentamycin, Amikacin, Tobramycin, Tetracycline, Tegacyclin, Rifampicin, and Polymyxin.

* * * * *